(12) United States Patent
Koh

(10) Patent No.: US 10,897,923 B2
(45) Date of Patent: Jan. 26, 2021

(54) METHOD USING SLIT-ROBO SYSTEM TO TREAT SARCOPENIA

(71) Applicant: DAEWOONG PHARMACEUTICAL CO., LTD., Gyeonggi-do (KR)

(72) Inventor: Jung Min Koh, Seoul (KR)

(73) Assignee: DAEWOONG PHARMACEUTICAL CO., LTD., Hwaseong-si (KR)

( * ) Notice: Subject to any disclaimer, the term of this patent is extended or adjusted under 35 U.S.C. 154(b) by 34 days.

(21) Appl. No.: 16/308,435

(22) PCT Filed: Jun. 8, 2017

(86) PCT No.: PCT/KR2017/005959
§ 371 (c)(1),
(2) Date: Dec. 7, 2018

(87) PCT Pub. No.: WO2017/213435
PCT Pub. Date: Dec. 14, 2017

(65) Prior Publication Data
US 2019/0133173 A1 May 9, 2019

(30) Foreign Application Priority Data

Jun. 8, 2016 (KR) .................. 10-2016-0071252
Jan. 31, 2017 (KR) .................. 10-2017-0013799

(51) Int. Cl.

| | | |
|---|---|---|
| A61P 21/00 | (2006.01) | |
| A23L 33/18 | (2016.01) | |
| A61K 38/17 | (2006.01) | |
| A61K 8/64 | (2006.01) | |
| A23L 33/13 | (2016.01) | |
| C07K 14/705 | (2006.01) | |
| C07K 14/47 | (2006.01) | |
| A61Q 19/00 | (2006.01) | |
| A23K 20/147 | (2016.01) | |
| A23K 20/153 | (2016.01) | |
| A23K 20/142 | (2016.01) | |
| G01N 33/68 | (2006.01) | |
| A61P 25/14 | (2006.01) | |
| A61Q 19/08 | (2006.01) | |
| A61Q 19/10 | (2006.01) | |

(52) U.S. Cl.
CPC ............ *A23L 33/18* (2016.08); *A23K 20/142* (2016.05); *A23K 20/147* (2016.05); *A23K 20/153* (2016.05); *A23L 33/13* (2016.08); *A61K 8/64* (2013.01); *A61K 38/17* (2013.01); *A61P 21/00* (2018.01); *A61P 25/14* (2018.01); *A61Q 19/00* (2013.01); *C07K 14/47* (2013.01); *C07K 14/70503* (2013.01); *G01N 33/6887* (2013.01); *A61Q 19/08* (2013.01); *A61Q 19/10* (2013.01)

(58) Field of Classification Search
CPC ....... A23L 33/18; A23L 33/13; A23K 20/142; A23K 20/147; A23K 20/153; A61P 25/14; A61P 21/00; A61K 8/64; A61K 38/17; A61Q 19/00; A61Q 19/08; A61Q 19/10; C07K 14/47; C07K 14/70503; G01N 33/6887

See application file for complete search history.

(56) References Cited

U.S. PATENT DOCUMENTS

2016/0120940 A1 5/2016 Robinson et al.

FOREIGN PATENT DOCUMENTS

| KR | 20130141395 A | 12/2013 |
|---|---|---|
| KR | 20140123516 A | 10/2014 |
| KR | 101617497 B1 | 5/2016 |
| WO | WO2012/042289 A1 | 4/2012 |

OTHER PUBLICATIONS

Zhang et al. "Heparan sulfate deficiency disrupts developmental angiogenesis and causes congenital diaphragmatic hernia." 2014. The Journal of Clinical Investigation. vol. 124 No. 1 pp. 209-221. (Year: 2014).*
Yuan et al. "A genetic model for a central (septum transversum) congenital diaphragmatic hernia in mice lacking Slit3." 2003. PNAS. vol. 100, No. 9, pp. 5217-5222. (Year: 2003).*
Yang et al. "Extracellular vesicles as a platform for membrane-associated therapeutic protein delivery". 2018, Journal of Extracellular Vesicles, vol. 7, 1440131, pp. 1-15 (Year: 2018).*
"Facts About Myopathies" published by Muscular Dystrophy Foundation Australia [online reference][Apr. 2015 archived version downloaded from: https://web.archive.org/web/20150413083837/http://mdaustralia.org.au/wp-content/uploads/2012/07/012_myopathies-2012.pdf] (Year: 2015).*
Kramer et al. "Switching Repulsion to Attraction: Changing Responses to Slit During Transition in Mesoderm Migration". 2001. Science. vol. 292, pp. 737-740. (Year: 2001).*
WIPO, Korean International Search Authority, International Search Report and Written Opinion dated Oct. 18, 2017 in International Patent Application No. PCT/KR2017/005959, 13 pagDec. 7, 2018.
Wu, Haitao et al., "Slit2 as a β-catenin/Ctnnb1-dependent retrograde signal for presynaptic differentiation," *eLife*, 4:e07266, Jul. 10, 2015, 20 pages.

(Continued)

Primary Examiner — Joanne Hama
Assistant Examiner — Scott T. Humbarger
(74) Attorney, Agent, or Firm — Masuvalley & Partners

(57) ABSTRACT

The present invention relates to a method using a SLIT-ROBO system to treat sarcopenia and, more specifically, to a method comprising administration of a gene selected from among slit1, slit2, slit3, robo1, robo2, and fragments thereof, or a protein expressed from the gene as an effective method for treating a muscle disease or for improving muscular function.

4 Claims, 25 Drawing Sheets
Specification includes a Sequence Listing.

(56) References Cited

OTHER PUBLICATIONS

Vargesson, Neil et al., "Expression patterns of Slit and Robo family members during vertebrate limb development", Mechanism of Development, 106 (2001) pp. 175-180, www.Elsevier.com.

* cited by examiner

NORMAL CONTROL GROUP | Slit3-DEFICIENT MOUSE

NORMAL CONTROL GROUP | Slit3-DEFICIENT MOUSE

■ Slit3 UNTREATED CONTROL GROUP

□ Slit3 TREATED EXPERIMENTAL GROUP

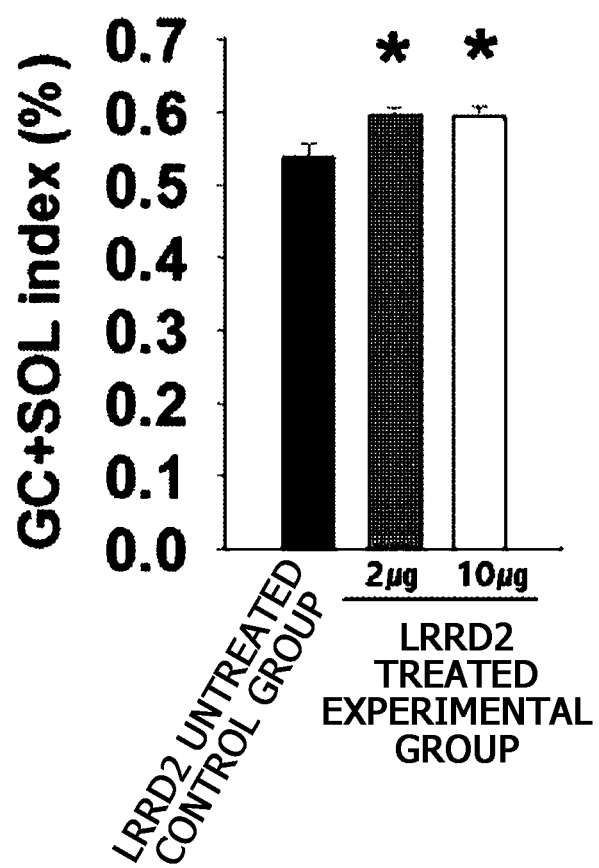

SEQUENCE LISTING

<160> NUMBER OF SEQ ID NOS: 8

<210> SEQ ID NO 1
<211> LENGTH: 1523
<212> TYPE: PRT
<213> ORGANISM: Artificial
<220> FEATURE:
<223> OTHER INFORMATION: Human Slit3 amino acid(AAQ89243)

<400> SEQUENCE: 1

Met Ala Pro Gly Trp Ala Gly Val Gly Ala Ala Val Arg Ala Arg Leu
1               5                   10                  15

Ala Leu Ala Leu Ala Leu Ala Ser Val Leu Ser Gly Pro Pro Ala Val
            20                  25                  30

Ala Cys Pro Thr Lys Cys Thr Cys Ser Ala Ala Ser Val Asp Cys His
        35                  40                  45

Gly Leu Gly Leu Arg Ala Val Pro Arg Gly Ile Pro Arg Asn Ala Glu
    50                  55                  60

Arg Leu Asp Leu Asp Arg Asn Asn Ile Thr Arg Ile Thr Lys Met Asp
65                  70                  75                  80

Phe Ala Gly Leu Lys Asn Leu Arg Val Leu His Leu Glu Asp Asn Gln
                85                  90                  95

```
Val Ser Val Ile Glu Arg Gly Ala Phe Gln Asp Leu Lys Gln Leu Glu
            100                 105                 110

Arg Leu Arg Leu Asn Lys Asn Lys Leu Gln Val Leu Pro Glu Leu Leu
        115                 120                 125

Phe Gln Ser Thr Pro Lys Leu Thr Arg Leu Asp Leu Ser Glu Asn Gln
    130                 135                 140

Ile Gln Gly Ile Pro Arg Lys Ala Phe Arg Gly Ile Thr Asp Val Lys
145                 150                 155                 160

Asn Leu Gln Leu Asp Asn Asn His Ile Ser Cys Ile Glu Asp Gly Ala
                165                 170                 175

Phe Arg Ala Leu Arg Asp Leu Glu Ile Leu Thr Leu Asn Asn Asn Asn
            180                 185                 190

Ile Ser Arg Ile Leu Val Thr Ser Phe Asn His Met Pro Lys Ile Arg
        195                 200                 205

Thr Leu Arg Leu His Ser Asn His Leu Tyr Cys Asp Cys His Leu Ala
    210                 215                 220

Trp Leu Ser Asp Trp Leu Arg Gln Arg Arg Thr Val Gly Gln Phe Thr
225                 230                 235                 240

Leu Cys Met Ala Pro Val His Leu Arg Gly Phe Asn Val Ala Asp Val
                245                 250                 255

Gln Lys Lys Glu Tyr Val Cys Pro Ala Pro His Ser Glu Pro Pro Ser
            260                 265                 270

Cys Asn Ala Asn Ser Ile Ser Cys Pro Ser Pro Cys Thr Cys Ser Asn
        275                 280                 285

Asn Ile Val Asp Cys Arg Gly Lys Gly Leu Met Glu Ile Pro Ala Asn
290                 295                 300

Leu Pro Glu Gly Ile Val Glu Ile Arg Leu Glu Gln Asn Ser Ile Lys
305                 310                 315                 320

Ala Ile Pro Ala Gly Ala Phe Thr Gln Tyr Lys Lys Leu Lys Arg Ile
                325                 330                 335

Asp Ile Ser Lys Asn Gln Ile Ser Asp Ile Ala Pro Asp Ala Phe Gln
            340                 345                 350

Gly Leu Lys Ser Leu Thr Ser Leu Val Leu Tyr Gly Asn Lys Ile Thr
        355                 360                 365

Glu Ile Ala Lys Gly Leu Phe Asp Gly Leu Val Ser Leu Gln Leu Leu
    370                 375                 380

Leu Leu Asn Ala Asn Lys Ile Asn Cys Leu Arg Val Asn Thr Phe Gln
385                 390                 395                 400

Asp Leu Gln Asn Leu Asn Leu Leu Ser Leu Tyr Asp Asn Lys Leu Gln
                405                 410                 415

Thr Ile Ser Lys Gly Leu Phe Ala Pro Leu Gln Ser Ile Gln Thr Leu
            420                 425                 430

His Leu Ala Gln Asn Pro Phe Val Cys Asp Cys His Leu Lys Trp Leu
        435                 440                 445

Ala Asp Tyr Leu Gln Asp Asn Pro Ile Glu Thr Ser Gly Ala Arg Cys
    450                 455                 460

Ser Ser Pro Arg Arg Leu Ala Asn Lys Arg Ile Ser Gln Ile Lys Ser
465                 470                 475                 480

Lys Lys Phe Arg Cys Ser Gly Ser Glu Asp Tyr Arg Ser Arg Phe Ser
                485                 490                 495

Ser Glu Cys Phe Met Asp Leu Val Cys Pro Glu Lys Cys Arg Cys Glu
            500                 505                 510

Gly Thr Ile Val Asp Cys Ser Asn Gln Lys Leu Val Arg Ile Pro Ser
```

```
            515                 520                 525
His Leu Pro Glu Tyr Val Thr Asp Leu Arg Leu Asn Asp Asn Glu Val
    530                 535                 540

Ser Val Leu Glu Ala Thr Gly Ile Phe Lys Lys Leu Pro Asn Leu Arg
545                 550                 555                 560

Lys Ile Asn Leu Ser Asn Asn Lys Ile Lys Glu Val Arg Glu Gly Ala
                565                 570                 575

Phe Asp Gly Ala Ala Ser Val Gln Glu Leu Met Leu Thr Gly Asn Gln
                580                 585                 590

Leu Glu Thr Val His Gly Arg Val Phe Arg Gly Leu Ser Gly Leu Lys
            595                 600                 605

Thr Leu Met Leu Arg Ser Asn Leu Ile Ser Cys Val Ser Asn Asp Thr
    610                 615                 620

Phe Ala Gly Leu Ser Ser Val Arg Leu Leu Ser Leu Tyr Asp Asn Arg
625                 630                 635                 640

Ile Thr Thr Ile Thr Pro Gly Ala Phe Thr Thr Leu Val Ser Leu Ser
                645                 650                 655

Thr Ile Asn Leu Leu Ser Asn Pro Phe Asn Cys Asn Cys His Leu Ala
                660                 665                 670

Trp Leu Gly Lys Trp Leu Arg Lys Arg Ile Val Ser Gly Asn Pro
                675                 680                 685

Arg Cys Gln Lys Pro Phe Phe Leu Lys Glu Ile Pro Ile Gln Asp Val
690                 695                 700

Ala Ile Gln Asp Phe Thr Cys Asp Gly Asn Glu Glu Ser Ser Cys Gln
705                 710                 715                 720

Leu Ser Pro Arg Cys Pro Glu Gln Cys Thr Cys Met Glu Thr Val Val
                725                 730                 735

Arg Cys Ser Asn Lys Gly Leu Arg Ala Leu Pro Arg Gly Met Pro Lys
                740                 745                 750

Asp Val Thr Glu Leu Tyr Leu Glu Gly Asn His Leu Thr Ala Val Pro
            755                 760                 765

Arg Glu Leu Ser Ala Leu Arg His Leu Thr Leu Ile Asp Leu Ser Asn
    770                 775                 780

Asn Ser Ile Ser Met Leu Thr Asn Tyr Thr Phe Ser Asn Met Ser His
785                 790                 795                 800

Leu Ser Thr Leu Ile Leu Ser Tyr Asn Arg Leu Arg Cys Ile Pro Val
                805                 810                 815

His Ala Phe Asn Gly Leu Arg Ser Leu Arg Val Leu Thr Leu His Gly
                820                 825                 830

Asn Asp Ile Ser Ser Val Pro Glu Gly Ser Phe Asn Asp Leu Thr Ser
            835                 840                 845

Leu Ser His Leu Ala Leu Gly Thr Asn Pro Leu His Cys Asp Cys Ser
    850                 855                 860

Leu Arg Trp Leu Ser Glu Trp Val Lys Ala Gly Tyr Lys Glu Pro Gly
865                 870                 875                 880

Ile Ala Arg Cys Ser Ser Pro Glu Pro Met Ala Asp Arg Leu Leu Leu
                885                 890                 895

Thr Thr Pro Thr His Arg Phe Gln Cys Lys Gly Pro Val Asp Ile Asn
                900                 905                 910

Ile Val Ala Lys Cys Asn Ala Cys Leu Ser Ser Pro Cys Lys Asn Asn
            915                 920                 925

Gly Thr Cys Thr Gln Asp Pro Val Glu Leu Tyr Arg Cys Ala Cys Pro
    930                 935                 940
```

```
Tyr Ser Tyr Lys Gly Lys Asp Cys Thr Val Pro Ile Asn Thr Cys Ile
945                 950                 955                 960

Gln Asn Pro Cys Gln His Gly Gly Thr Cys His Leu Ser Asp Ser His
                965                 970                 975

Lys Asp Gly Phe Ser Cys Ser Cys Pro Leu Gly Phe Glu Gly Gln Arg
            980                 985                 990

Cys Glu Ile Asn Pro Asp Asp Cys Glu Asp Asn Asp Cys Glu Asn Asn
        995                 1000                1005

Ala Thr Cys Val Asp Gly Ile Asn Asn Tyr Val Cys Ile Cys Pro
    1010                1015                1020

Pro Asn Tyr Thr Gly Glu Leu Cys Asp Glu Val Ile Asp His Cys
    1025                1030                1035

Val Pro Glu Leu Asn Leu Cys Gln His Glu Ala Lys Cys Ile Pro
    1040                1045                1050

Leu Asp Lys Gly Phe Ser Cys Glu Cys Val Pro Gly Tyr Ser Gly
    1055                1060                1065

Lys Leu Cys Glu Thr Asp Asn Asp Asp Cys Val Ala His Lys Cys
    1070                1075                1080

Arg His Gly Ala Gln Cys Val Asp Thr Ile Asn Gly Tyr Thr Cys
    1085                1090                1095

Thr Cys Pro Gln Gly Phe Ser Gly Pro Phe Cys Glu His Pro Pro
    1100                1105                1110

Pro Met Val Leu Leu Gln Thr Ser Pro Cys Asp Gln Tyr Glu Cys
    1115                1120                1125

Gln Asn Gly Ala Gln Cys Ile Val Val Gln Gln Glu Pro Thr Cys
    1130                1135                1140

Arg Cys Pro Pro Gly Phe Ala Gly Pro Arg Cys Glu Lys Leu Ile
    1145                1150                1155

Thr Val Asn Phe Val Gly Lys Asp Ser Tyr Val Glu Leu Ala Ser
    1160                1165                1170

Ala Lys Val Arg Pro Gln Ala Asn Ile Ser Leu Gln Val Ala Thr
    1175                1180                1185

Asp Lys Asp Asn Gly Ile Leu Leu Tyr Lys Gly Asp Asn Asp Pro
    1190                1195                1200

Leu Ala Leu Glu Leu Tyr Gln Gly His Val Arg Leu Val Tyr Asp
    1205                1210                1215

Ser Leu Ser Ser Pro Pro Thr Thr Val Tyr Ser Val Glu Thr Val
    1220                1225                1230

Asn Asp Gly Gln Phe His Ser Val Glu Leu Val Thr Leu Asn Gln
    1235                1240                1245

Thr Leu Asn Leu Val Val Asp Lys Gly Thr Pro Lys Ser Leu Gly
    1250                1255                1260

Lys Leu Gln Lys Gln Pro Ala Val Gly Ile Asn Ser Pro Leu Tyr
    1265                1270                1275

Leu Gly Gly Ile Pro Thr Ser Thr Gly Leu Ser Ala Leu Arg Gln
    1280                1285                1290

Gly Thr Asp Arg Pro Leu Gly Gly Phe His Gly Cys Ile His Glu
    1295                1300                1305

Val Arg Ile Asn Asn Glu Leu Gln Asp Phe Lys Ala Leu Pro Pro
    1310                1315                1320

Gln Ser Leu Gly Val Ser Pro Gly Cys Lys Ser Cys Thr Val Cys
    1325                1330                1335
```

-continued

```
Lys His Gly Leu Cys Arg Ser Val Glu Lys Asp Ser Val Val Cys
    1340                1345                1350

Glu Cys Arg Pro Gly Trp Thr Gly Pro Leu Cys Asp Gln Glu Ala
    1355                1360                1365

Arg Asp Pro Cys Leu Gly His Arg Cys His His Gly Lys Cys Val
    1370                1375                1380

Ala Thr Gly Thr Ser Tyr Met Cys Lys Cys Ala Glu Gly Tyr Gly
    1385                1390                1395

Gly Asp Leu Cys Asp Asn Lys Asn Asp Ser Ala Asn Ala Cys Ser
    1400                1405                1410

Ala Phe Lys Cys His His Gly Gln Cys His Ile Ser Asp Gln Gly
    1415                1420                1425

Glu Pro Tyr Cys Leu Cys Gln Pro Gly Phe Ser Gly Glu His Cys
    1430                1435                1440

Gln Gln Glu Asn Pro Cys Leu Gly Gln Val Val Arg Glu Val Ile
    1445                1450                1455

Arg Arg Gln Lys Gly Tyr Ala Ser Cys Ala Thr Ala Ser Lys Val
    1460                1465                1470

Pro Ile Met Glu Cys Arg Gly Gly Cys Gly Pro Gln Cys Cys Gln
    1475                1480                1485

Pro Thr Arg Ser Lys Arg Arg Lys Tyr Val Phe Gln Cys Thr Asp
    1490                1495                1500

Gly Ser Ser Phe Val Glu Glu Val Glu Arg His Leu Glu Cys Gly
    1505                1510                1515

Cys Leu Ala Cys Ser
    1520
```

<210> SEQ ID NO 2
<211> LENGTH: 1651
<212> TYPE: PRT
<213> ORGANISM: Artificial
<220> FEATURE:
<223> OTHER INFORMATION: Robo1 amino acid (AAC39575)

<400> SEQUENCE: 2

```
Met Lys Trp Lys His Val Pro Phe Leu Val Met Ile Ser Leu Leu Ser
1               5                   10                  15

Leu Ser Pro Asn His Leu Phe Leu Ala Gln Leu Ile Pro Asp Pro Glu
            20                  25                  30

Asp Val Glu Arg Gly Asn Asp His Gly Thr Pro Ile Pro Thr Ser Asp
        35                  40                  45

Asn Asp Asp Asn Ser Leu Gly Tyr Thr Gly Ser Arg Leu Arg Gln Glu
    50                  55                  60

Asp Phe Pro Pro Arg Ile Val Glu His Pro Ser Asp Leu Ile Val Ser
65                  70                  75                  80

Lys Gly Glu Pro Ala Thr Leu Asn Cys Lys Ala Glu Gly Arg Pro Thr
                85                  90                  95

Pro Thr Ile Glu Trp Tyr Lys Gly Gly Glu Arg Val Glu Thr Asp Lys
            100                 105                 110

Asp Asp Pro Arg Ser His Arg Met Leu Leu Pro Ser Gly Ser Leu Phe
        115                 120                 125

Phe Leu Arg Ile Val His Gly Arg Lys Ser Arg Pro Asp Glu Gly Val
    130                 135                 140

Tyr Val Cys Val Ala Arg Asn Tyr Leu Gly Glu Ala Val Ser His Asn
145                 150                 155                 160
```

```
Ala Ser Leu Glu Val Ala Ile Leu Arg Asp Asp Phe Arg Gln Asn Pro
                165                 170                 175
Ser Asp Val Met Val Ala Val Gly Glu Pro Ala Val Met Glu Cys Gln
            180                 185                 190
Pro Pro Arg Gly His Pro Glu Pro Thr Ile Ser Trp Lys Lys Asp Gly
        195                 200                 205
Ser Pro Leu Asp Asp Lys Asp Glu Arg Ile Thr Ile Arg Gly Gly Lys
    210                 215                 220
Leu Met Ile Thr Tyr Thr Arg Lys Ser Asp Ala Gly Lys Tyr Val Cys
225                 230                 235                 240
Val Gly Thr Asn Met Val Gly Glu Arg Glu Ser Glu Val Ala Glu Leu
                245                 250                 255
Thr Val Leu Glu Arg Pro Ser Phe Val Lys Arg Pro Ser Asn Leu Ala
            260                 265                 270
Val Thr Val Asp Asp Ser Ala Glu Phe Lys Cys Glu Ala Arg Gly Asp
        275                 280                 285
Pro Val Pro Thr Val Arg Trp Arg Lys Asp Asp Gly Glu Leu Pro Lys
    290                 295                 300
Ser Arg Tyr Glu Ile Arg Asp Asp His Thr Leu Lys Ile Arg Lys Val
305                 310                 315                 320
Thr Ala Gly Asp Met Gly Ser Tyr Thr Cys Val Ala Glu Asn Met Val
                325                 330                 335
Gly Lys Ala Glu Ala Ser Ala Thr Leu Thr Val Gln Glu Pro Pro His
            340                 345                 350
Phe Val Val Lys Pro Arg Asp Gln Val Val Ala Leu Gly Arg Thr Val
        355                 360                 365
Thr Phe Gln Cys Glu Ala Thr Gly Asn Pro Gln Pro Ala Ile Phe Trp
    370                 375                 380
Arg Arg Glu Gly Ser Gln Asn Leu Leu Phe Ser Tyr Gln Pro Pro Gln
385                 390                 395                 400
Ser Ser Ser Arg Phe Ser Val Ser Gln Thr Gly Asp Leu Thr Ile Thr
                405                 410                 415
Asn Val Gln Arg Ser Asp Val Gly Tyr Tyr Ile Cys Gln Thr Leu Asn
            420                 425                 430
Val Ala Gly Ser Ile Ile Thr Lys Ala Tyr Leu Glu Val Thr Asp Val
        435                 440                 445
Ile Ala Asp Arg Pro Pro Val Ile Arg Gln Gly Pro Val Asn Gln
    450                 455                 460
Thr Val Ala Val Asp Gly Thr Phe Val Leu Ser Cys Val Ala Thr Gly
465                 470                 475                 480
Ser Pro Val Pro Thr Ile Leu Trp Arg Lys Asp Gly Val Leu Val Ser
                485                 490                 495
Thr Gln Asp Ser Arg Ile Lys Gln Leu Glu Asn Gly Val Leu Gln Ile
            500                 505                 510
Arg Tyr Ala Lys Leu Gly Asp Thr Gly Arg Tyr Thr Cys Ile Ala Ser
        515                 520                 525
Thr Pro Ser Gly Glu Ala Thr Trp Ser Ala Tyr Ile Glu Val Gln Glu
    530                 535                 540
Phe Gly Val Pro Val Gln Pro Pro Arg Pro Thr Asp Pro Asn Leu Ile
545                 550                 555                 560
Pro Ser Ala Pro Ser Lys Pro Glu Val Thr Asp Val Ser Arg Asn Thr
                565                 570                 575
Val Thr Leu Ser Trp Gln Pro Asn Leu Asn Ser Gly Ala Thr Pro Thr
```

```
                    580                 585                 590
Ser Tyr Ile Ile Glu Ala Phe Ser His Ala Ser Gly Ser Ser Trp Gln
                595                 600                 605

Thr Val Ala Glu Asn Val Lys Thr Glu Thr Ser Ala Ile Lys Gly Leu
            610                 615                 620

Lys Pro Asn Ala Ile Tyr Leu Phe Leu Val Arg Ala Ala Asn Ala Tyr
625                 630                 635                 640

Gly Ile Ser Asp Pro Ser Gln Ile Ser Asp Pro Val Lys Thr Gln Asp
                645                 650                 655

Val Leu Pro Thr Ser Gln Gly Val Asp His Lys Gln Val Gln Arg Glu
            660                 665                 670

Leu Gly Asn Ala Val Leu His Leu His Asn Pro Thr Val Leu Ser Ser
            675                 680                 685

Ser Ser Ile Glu Val His Trp Thr Val Asp Gln Gln Ser Gln Tyr Ile
            690                 695                 700

Gln Gly Tyr Lys Ile Leu Tyr Arg Pro Ser Gly Ala Asn His Gly Glu
705                 710                 715                 720

Ser Asp Trp Leu Val Phe Glu Val Arg Thr Pro Ala Lys Asn Ser Val
                725                 730                 735

Val Ile Pro Asp Leu Arg Lys Gly Val Asn Tyr Glu Ile Lys Ala Arg
                740                 745                 750

Pro Phe Phe Asn Glu Phe Gln Gly Ala Asp Ser Glu Ile Lys Phe Ala
                755                 760                 765

Lys Thr Leu Glu Glu Ala Pro Ser Ala Pro Pro Gln Gly Val Thr Val
    770                 775                 780

Ser Lys Asn Asp Gly Asn Gly Thr Ala Ile Leu Val Ser Trp Gln Pro
785                 790                 795                 800

Pro Pro Glu Asp Thr Gln Asn Gly Met Val Gln Glu Tyr Lys Val Trp
                805                 810                 815

Cys Leu Gly Asn Glu Thr Arg Tyr His Ile Asn Lys Thr Val Asp Gly
                820                 825                 830

Ser Thr Phe Ser Val Val Ile Pro Phe Leu Val Pro Gly Ile Arg Tyr
            835                 840                 845

Ser Val Glu Val Ala Ala Ser Thr Gly Ala Gly Ser Gly Val Lys Ser
850                 855                 860

Glu Pro Gln Phe Ile Gln Leu Asp Ala His Gly Asn Pro Val Ser Pro
865                 870                 875                 880

Glu Asp Gln Val Ser Leu Ala Gln Gln Ile Ser Asp Val Val Lys Gln
                885                 890                 895

Pro Ala Phe Ile Ala Gly Ile Gly Ala Ala Cys Trp Ile Ile Leu Met
                900                 905                 910

Val Phe Ser Ile Trp Leu Tyr Arg His Arg Lys Lys Arg Asn Gly Leu
            915                 920                 925

Thr Ser Thr Tyr Ala Gly Ile Arg Lys Val Pro Ser Phe Thr Phe Thr
            930                 935                 940

Pro Thr Val Thr Tyr Gln Arg Gly Gly Glu Ala Val Ser Ser Gly Gly
945                 950                 955                 960

Arg Pro Gly Leu Leu Asn Ile Ser Glu Pro Ala Ala Gln Pro Trp Leu
                965                 970                 975

Ala Asp Thr Trp Pro Asn Thr Gly Asn Asn His Asn Asp Cys Ser Ile
                980                 985                 990

Ser Cys Cys Thr Ala Gly Asn Gly  Asn Ser Asp Ser Asn  Leu Thr Thr
            995                1000               1005
```

-continued

Tyr Ser Arg Pro Ala Asp Cys Ile Ala Asn Tyr Asn Asn Gln Leu
1010              1015              1020

Asp Asn Lys Gln Thr Asn Leu Met Leu Pro Glu Ser Thr Val Tyr
1025              1030              1035

Gly Asp Val Asp Leu Ser Asn Lys Ile Asn Glu Met Lys Thr Phe
1040              1045              1050

Asn Ser Pro Asn Leu Lys Asp Gly Arg Phe Val Asn Pro Ser Gly
1055              1060              1065

Gln Pro Thr Pro Tyr Ala Thr Thr Gln Leu Ile Gln Ser Asn Leu
1070              1075              1080

Ser Asn Asn Met Asn Asn Gly Ser Gly Asp Ser Gly Glu Lys His
1085              1090              1095

Trp Lys Pro Leu Gly Gln Gln Lys Gln Glu Val Ala Pro Val Gln
1100              1105              1110

Tyr Asn Ile Val Glu Gln Asn Lys Leu Asn Lys Asp Tyr Arg Ala
1115              1120              1125

Asn Asp Thr Val Pro Pro Thr Ile Pro Tyr Asn Gln Ser Tyr Asp
1130              1135              1140

Gln Asn Thr Gly Gly Ser Tyr Asn Ser Ser Asp Arg Gly Ser Ser
1145              1150              1155

Thr Ser Gly Ser Gln Gly His Lys Lys Gly Ala Arg Thr Pro Lys
1160              1165              1170

Val Pro Lys Gln Gly Gly Met Asn Trp Ala Asp Leu Leu Pro Pro
1175              1180              1185

Pro Pro Ala His Pro Pro Pro His Ser Asn Ser Glu Glu Tyr Asn
1190              1195              1200

Ile Ser Val Asp Glu Ser Tyr Asp Gln Glu Met Pro Cys Pro Val
1205              1210              1215

Pro Pro Ala Arg Met Tyr Leu Gln Gln Asp Glu Leu Glu Glu Glu
1220              1225              1230

Glu Asp Glu Arg Gly Pro Thr Pro Pro Val Arg Gly Ala Ala Ser
1235              1240              1245

Ser Pro Ala Ala Val Ser Tyr Ser His Gln Ser Thr Ala Thr Leu
1250              1255              1260

Thr Pro Ser Pro Gln Glu Glu Leu Gln Pro Met Leu Gln Asp Cys
1265              1270              1275

Pro Glu Glu Thr Gly His Met Gln His Gln Pro Asp Arg Arg Arg
1280              1285              1290

Gln Pro Val Ser Pro Pro Pro Pro Arg Pro Ile Ser Pro Pro
1295              1300              1305

His Thr Tyr Gly Tyr Ile Ser Gly Pro Leu Val Ser Asp Met Asp
1310              1315              1320

Thr Asp Ala Pro Glu Glu Glu Asp Glu Ala Asp Met Glu Val
1325              1330              1335

Ala Lys Met Gln Thr Arg Arg Leu Leu Leu Arg Gly Leu Glu Gln
1340              1345              1350

Thr Pro Ala Ser Ser Val Gly Asp Leu Glu Ser Ser Val Thr Gly
1355              1360              1365

Ser Met Ile Asn Gly Trp Gly Ser Ala Ser Glu Glu Asp Asn Ile
1370              1375              1380

Ser Ser Gly Arg Ser Ser Val Ser Ser Ser Asp Gly Ser Phe Phe
1385              1390              1395

-continued

```
Thr Asp Ala Asp Phe Ala Gln Ala Val Ala Ala Ala Glu Tyr
    1400                1405                1410

Ala Gly Leu Lys Val Ala Arg Arg Gln Met Gln Asp Ala Ala Gly
1415                1420                1425

Arg Arg His Phe His Ala Ser Gln Cys Pro Arg Pro Thr Ser Pro
    1430                1435                1440

Val Ser Thr Asp Ser Asn Met Ser Ala Ala Val Met Gln Lys Thr
    1445                1450                1455

Arg Pro Ala Lys Lys Leu Lys His Gln Pro Gly His Leu Arg Arg
    1460                1465                1470

Glu Thr Tyr Thr Asp Asp Leu Pro Pro Pro Val Pro Pro Pro
    1475                1480                1485

Ala Ile Lys Ser Pro Thr Ala Gln Ser Lys Thr Gln Leu Glu Val
    1490                1495                1500

Arg Pro Val Val Val Pro Lys Leu Pro Ser Met Asp Ala Arg Thr
    1505                1510                1515

Asp Arg Ser Ser Asp Arg Lys Gly Ser Ser Tyr Lys Gly Arg Glu
    1520                1525                1530

Val Leu Asp Gly Arg Gln Val Val Asp Met Arg Thr Asn Pro Gly
    1535                1540                1545

Asp Pro Arg Glu Ala Gln Glu Gln Gln Asn Asp Gly Lys Gly Arg
    1550                1555                1560

Gly Asn Lys Ala Ala Lys Arg Asp Leu Pro Pro Ala Lys Thr His
    1565                1570                1575

Leu Ile Gln Glu Asp Ile Leu Pro Tyr Cys Arg Pro Thr Phe Pro
    1580                1585                1590

Thr Ser Asn Asn Pro Arg Asp Pro Ser Ser Ser Ser Met Ser
    1595                1600                1605

Ser Arg Gly Ser Gly Ser Arg Gln Arg Glu Gln Ala Asn Val Gly
    1610                1615                1620

Arg Arg Asn Ile Ala Glu Met Gln Val Leu Gly Gly Tyr Glu Arg
    1625                1630                1635

Gly Glu Asp Asn Asn Glu Glu Leu Glu Glu Thr Glu Ser
    1640                1645                1650

<210> SEQ ID NO 3
<211> LENGTH: 1394
<212> TYPE: PRT
<213> ORGANISM: Artificial
<220> FEATURE:
<223> OTHER INFORMATION: Robo2 amino acid (NP_001122401.1)

<400> SEQUENCE: 3

Met Ala Arg Arg His Glu Arg Val Thr Arg Arg Met Trp Thr Trp Ala
1               5                   10                  15

Pro Gly Leu Leu Met Met Thr Val Val Phe Trp Gly His Gln Gly Asn
                20                  25                  30

Gly Gln Gly Gln Gly Ser Arg Leu Arg Gln Glu Asp Phe Pro Pro Arg
        35                  40                  45

Ile Val Glu His Pro Ser Asp Val Ile Val Ser Lys Gly Glu Pro Thr
    50                  55                  60

Thr Leu Asn Cys Lys Ala Glu Gly Arg Pro Thr Pro Thr Ile Glu Trp
65                  70                  75                  80

Tyr Lys Asp Gly Glu Arg Val Glu Thr Asp Lys Asp Asp Pro Arg Ser
                85                  90                  95
```

-continued

His Arg Met Leu Leu Pro Ser Gly Ser Leu Phe Phe Leu Arg Ile Val
            100                 105                 110

His Gly Arg Arg Ser Lys Pro Asp Glu Gly Ser Tyr Val Cys Val Ala
            115                 120                 125

Arg Asn Tyr Leu Gly Glu Ala Val Ser Arg Asn Ala Ser Leu Glu Val
        130                 135                 140

Ala Leu Leu Arg Asp Asp Phe Arg Gln Asn Pro Thr Asp Val Val Val
145                 150                 155                 160

Ala Ala Gly Glu Pro Ala Ile Leu Glu Cys Gln Pro Arg Gly His
            165                 170                 175

Pro Glu Pro Thr Ile Tyr Trp Lys Lys Asp Lys Val Arg Ile Asp Asp
            180                 185                 190

Lys Glu Glu Arg Ile Ser Ile Arg Gly Gly Lys Leu Met Ile Ser Asn
        195                 200                 205

Thr Arg Lys Ser Asp Ala Gly Met Tyr Thr Cys Val Gly Thr Asn Met
    210                 215                 220

Val Gly Glu Arg Asp Ser Asp Pro Ala Glu Leu Thr Val Phe Glu Arg
225                 230                 235                 240

Pro Thr Phe Leu Arg Arg Pro Ile Asn Gln Val Val Leu Glu Glu Glu
            245                 250                 255

Ala Val Glu Phe Arg Cys Gln Val Gln Gly Asp Pro Gln Pro Thr Val
            260                 265                 270

Arg Trp Lys Lys Asp Asp Ala Asp Leu Pro Arg Gly Arg Tyr Asp Ile
        275                 280                 285

Lys Asp Asp Tyr Thr Leu Arg Ile Lys Lys Thr Met Ser Thr Asp Glu
    290                 295                 300

Gly Thr Tyr Met Cys Ile Ala Glu Asn Arg Val Gly Lys Met Glu Ala
305                 310                 315                 320

Ser Ala Thr Leu Thr Val Arg Ala Pro Pro Gln Phe Val Val Arg Pro
            325                 330                 335

Arg Asp Gln Ile Val Ala Gln Gly Arg Thr Val Thr Phe Pro Cys Glu
            340                 345                 350

Thr Lys Gly Asn Pro Gln Pro Ala Val Phe Trp Gln Lys Glu Gly Ser
        355                 360                 365

Gln Asn Leu Leu Phe Pro Asn Gln Pro Gln Gln Pro Asn Ser Arg Cys
    370                 375                 380

Ser Val Ser Pro Thr Gly Asp Leu Thr Ile Thr Asn Ile Gln Arg Ser
385                 390                 395                 400

Asp Ala Gly Tyr Tyr Ile Cys Gln Ala Leu Thr Val Ala Gly Ser Ile
            405                 410                 415

Leu Ala Lys Ala Gln Leu Glu Val Thr Asp Val Leu Thr Asp Arg Pro
            420                 425                 430

Pro Pro Ile Ile Leu Gln Gly Pro Ala Asn Gln Thr Leu Ala Val Asp
        435                 440                 445

Gly Thr Ala Leu Leu Lys Cys Lys Ala Thr Gly Asp Pro Leu Pro Val
    450                 455                 460

Ile Ser Trp Leu Lys Glu Gly Phe Thr Phe Pro Gly Arg Asp Pro Arg
465                 470                 475                 480

Ala Thr Ile Gln Glu Gln Gly Thr Leu Gln Ile Lys Asn Leu Arg Ile
            485                 490                 495

Ser Asp Thr Gly Thr Tyr Thr Cys Val Ala Thr Ser Ser Ser Gly Glu
            500                 505                 510

Thr Ser Trp Ser Ala Val Leu Asp Val Thr Glu Ser Gly Ala Thr Ile

```
            515                 520                 525
Ser Lys Asn Tyr Asp Leu Ser Asp Leu Pro Gly Pro Pro Ser Lys Pro
            530                 535                 540

Gln Val Thr Asp Val Thr Lys Asn Ser Val Thr Leu Ser Trp Gln Pro
545                 550                 555                 560

Gly Thr Pro Gly Thr Leu Pro Ala Ser Ala Tyr Ile Ile Glu Ala Phe
                565                 570                 575

Ser Gln Ser Val Ser Asn Ser Trp Gln Thr Val Ala Asn His Val Lys
            580                 585                 590

Thr Thr Leu Tyr Thr Val Arg Gly Leu Arg Pro Asn Thr Ile Tyr Leu
            595                 600                 605

Phe Met Val Arg Ala Ile Asn Pro Gln Gly Leu Ser Asp Pro Ser Pro
            610                 615                 620

Met Ser Asp Pro Val Arg Thr Gln Asp Ile Ser Pro Ala Gln Gly
625                 630                 635                 640

Val Asp His Arg Gln Val Gln Lys Glu Leu Gly Asp Val Leu Val Arg
                645                 650                 655

Leu His Asn Pro Val Val Leu Thr Pro Thr Thr Val Gln Val Thr Trp
            660                 665                 670

Thr Val Asp Arg Gln Pro Gln Phe Ile Gln Gly Tyr Arg Val Met Tyr
            675                 680                 685

Arg Gln Thr Ser Gly Leu Gln Ala Thr Ser Ser Trp Gln Asn Leu Asp
            690                 695                 700

Ala Lys Val Pro Thr Glu Arg Ser Ala Val Leu Val Asn Leu Lys Lys
705                 710                 715                 720

Gly Val Thr Tyr Glu Ile Lys Val Arg Pro Tyr Phe Asn Glu Phe Gln
                725                 730                 735

Gly Met Asp Ser Glu Ser Lys Thr Val Arg Thr Thr Glu Glu Ala Pro
            740                 745                 750

Ser Ala Pro Pro Gln Ser Val Thr Val Leu Thr Val Gly Ser Tyr Asn
            755                 760                 765

Ser Thr Ser Ile Ser Val Ser Trp Asp Pro Pro Pro Pro Asp His Gln
            770                 775                 780

Asn Gly Ile Ile Gln Glu Tyr Lys Ile Trp Cys Leu Gly Asn Glu Thr
785                 790                 795                 800

Arg Phe His Ile Asn Lys Thr Val Asp Ala Ala Ile Arg Ser Val Ile
                805                 810                 815

Ile Gly Gly Leu Phe Pro Gly Ile Gln Tyr Arg Val Glu Val Ala Ala
            820                 825                 830

Ser Thr Ser Ala Gly Val Gly Val Lys Ser Glu Pro Gln Pro Ile Ile
            835                 840                 845

Ile Gly Arg Arg Asn Glu Val Val Ile Thr Glu Asn Asn Asn Ser Ile
            850                 855                 860

Thr Glu Gln Ile Thr Asp Val Val Lys Gln Pro Ala Phe Ile Ala Gly
865                 870                 875                 880

Ile Gly Gly Ala Cys Trp Val Ile Leu Met Gly Phe Ser Ile Trp Leu
                885                 890                 895

Tyr Trp Arg Arg Lys Lys Arg Lys Gly Leu Ser Asn Tyr Ala Val Thr
            900                 905                 910

Phe Gln Arg Gly Asp Gly Gly Leu Met Ser Asn Gly Ser Arg Pro Gly
            915                 920                 925

Leu Leu Asn Ala Gly Asp Pro Ser Tyr Pro Trp Leu Ala Asp Ser Trp
930                 935                 940
```

-continued

```
Pro Ala Thr Ser Leu Pro Val Asn Asn Ser Asn Ser Gly Pro Asn Glu
945                 950                 955                 960

Ile Gly Asn Phe Gly Arg Gly Asp Val Leu Pro Val Pro Gly Gln
            965                 970                 975

Gly Asp Lys Thr Ala Thr Met Leu Ser Asp Gly Ala Ile Tyr Ser Ser
            980                 985                 990

Ile Asp Phe Thr Thr Lys Thr Ser Tyr Asn Ser Ser Ser Gln Ile Thr
            995                 1000                1005

Gln Ala Thr Pro Tyr Ala Thr Thr Gln Ile Leu His Ser Asn Ser
    1010                1015                1020

Ile His Glu Leu Ala Val Asp Leu Pro Asp Pro Gln Trp Lys Ser
    1025                1030                1035

Ser Ile Gln Gln Lys Thr Asp Leu Met Gly Phe Gly Tyr Ser Leu
    1040                1045                1050

Pro Asp Gln Asn Lys Gly Asn Asn Gly Gly Lys Gly Gly Lys Lys
    1055                1060                1065

Lys Lys Asn Lys Asn Ser Ser Lys Pro Gln Lys Asn Asn Gly Ser
    1070                1075                1080

Thr Trp Ala Asn Val Pro Leu Pro Pro Pro Val Gln Pro Leu
    1085                1090                1095

Pro Gly Thr Glu Leu Glu His Tyr Ala Val Glu Gln Gln Glu Asn
    1100                1105                1110

Gly Tyr Asp Ser Asp Ser Trp Cys Pro Pro Leu Pro Val Gln Thr
    1115                1120                1125

Tyr Leu His Gln Gly Leu Glu Asp Glu Leu Glu Glu Asp Asp Asp
    1130                1135                1140

Arg Val Pro Thr Pro Pro Val Arg Gly Val Ala Ser Ser Pro Ala
    1145                1150                1155

Ile Ser Phe Gly Gln Gln Ser Thr Ala Thr Leu Thr Pro Ser Pro
    1160                1165                1170

Arg Glu Glu Met Gln Pro Met Leu Gln Ala His Leu Asp Glu Leu
    1175                1180                1185

Thr Arg Ala Tyr Gln Phe Asp Ile Ala Lys Gln Thr Trp His Ile
    1190                1195                1200

Gln Ser Asn Asn Gln Pro Pro Gln Pro Pro Val Pro Pro Leu Gly
    1205                1210                1215

Tyr Val Ser Gly Ala Leu Ile Ser Asp Leu Glu Thr Asp Val Ala
    1220                1225                1230

Asp Asp Asp Ala Asp Asp Glu Glu Ala Leu Glu Ile Pro Arg
    1235                1240                1245

Pro Leu Arg Ala Leu Asp Gln Thr Pro Gly Ser Ser Met Asp Asn
    1250                1255                1260

Leu Asp Ser Ser Val Thr Gly Lys Ala Phe Thr Ser Ser Gln Arg
    1265                1270                1275

Pro Arg Pro Thr Ser Pro Phe Ser Thr Asp Ser Asn Thr Ser Ala
    1280                1285                1290

Ala Leu Ser Gln Ser Gln Arg Pro Arg Pro Thr Lys Lys His Lys
    1295                1300                1305

Gly Gly Arg Met Asp Gln Gln Pro Ala Leu Pro His Arg Arg Glu
    1310                1315                1320

Gly Met Thr Asp Glu Glu Ala Leu Val Pro Tyr Ser Lys Pro Ser
    1325                1330                1335
```

-continued

```
Phe Pro Ser Pro Gly Gly His Ser Ser Ser Gly Thr Ala Ser Ser
    1340                1345                1350

Lys Gly Ser Thr Gly Pro Arg Lys Thr Glu Val Leu Arg Ala Gly
    1355                1360                1365

His Gln Arg Asn Ala Ser Asp Leu Leu Asp Ile Gly Tyr Met Gly
    1370                1375                1380

Ser Asn Ser Gln Gly Gln Phe Thr Gly Glu Leu
    1385                1390

<210> SEQ ID NO 4
<211> LENGTH: 130
<212> TYPE: PRT
<213> ORGANISM: Artificial
<220> FEATURE:
<223> OTHER INFORMATION: LRRD2 amino acid

<400> SEQUENCE: 4

Ile Val Glu Ile Arg Leu Glu Gln Asn Ser Ile Lys Ala Ile Pro Ala
1               5                   10                  15

Gly Ala Phe Thr Gln Tyr Lys Lys Leu Lys Arg Ile Asp Ile Ser Lys
            20                  25                  30

Asn Gln Ile Ser Asp Ile Ala Pro Asp Ala Phe Gln Gly Leu Lys Ser
        35                  40                  45

Leu Thr Ser Leu Val Leu Tyr Gly Asn Lys Ile Thr Glu Ile Ala Lys
    50                  55                  60

Gly Leu Phe Asp Gly Leu Val Ser Leu Gln Leu Leu Leu Asn Ala
65                  70                  75              80

Asn Lys Ile Asn Cys Leu Arg Val Asn Thr Phe Gln Asp Leu Gln Asn
                85                  90                  95

Leu Asn Leu Leu Ser Leu Tyr Asp Asn Lys Leu Gln Thr Ile Ser Lys
            100                 105                 110

Gly Leu Phe Ala Pro Leu Gln Ser Ile Gln Thr Leu His Leu Ala Gln
        115                 120                 125

Asn Pro
    130

<210> SEQ ID NO 5
<211> LENGTH: 4842
<212> TYPE: DNA
<213> ORGANISM: Artificial
<220> FEATURE:
<223> OTHER INFORMATION: slit3 gene(AY358884)

<400> SEQUENCE: 5
cgcgctcccc gcgcgcctcc tcgggctcca cgcgtcttgc cccgcagagg cagcctcctc      60
caggagcggg gccctgcaca ccatggcccc cgggtgggca gggtcggcg ccgccgtgcg     120 cgcccgcctg gcgctggcct tggcgctggc gagcgtcctg agtgggcctc cagccgtcgc     180
ctgccccacc aagtgtacct gctccgctgc cagcgtggac tgccacgggc tgggcctccg     240
cgcggttcct cggggcatcc ccgcaacgc tgagcgcctt gacctggaca gaaataatat     300
caccaggatc accaagatgg acttcgctgg gctcaagaac ctccgagtct tgcatctgga     360
agacaaccag gtcagcgtca tcgagagagg cgccttccag gacctgaagc agctagagcg     420
actgcgcctg aacaagaata agctgcaagt ccttccagaa ttgcttttcc agagcacgcc     480
gaagctcacc agactagatt tgagtgaaaa ccagatccag gggatcccga ggaaggcgtt     540
ccgcggcatc accgatgtga agaacctgca actggacaac aaccacatca gctgcattga     600
```

```
agatggagcc ttccgagcgc tgcgcgattt ggagatcctt accctcaaca acaacaacat    660
cagtcgcatc ctggtcacca gcttcaacca catgccgaag atccgaactc tgcgcctcca    720
ctccaaccac ctctactgcg actgccacct ggcctggctc tcggattggc tgcgacagcg    780
acggacagtt ggccagttca cactctgcat ggctcctgtg catttgaggg gcttcaacgt    840
ggcggatgtg cagaagaagg agtacgtgtg cccagccccc cactcggagc ccccatcctg    900
caatgccaac tccatctcct gcccttcgcc ctgcacgtgc agcaataaca tcgtggactg    960
tcgaggaaag ggcttgatgg agattcctgc caacttgccg gagggcatcg tcgaaatacg   1020
cctagaacag aactccatca aagccatccc tgcaggagcc ttcacccagt acaagaaact   1080
gaagcgaata gacatcagca agaatcagat atcggatatt gctccagatg ccttccaggg   1140
cctgaaatca ctcacatcgc tggtcctgta tgggaacaag atcaccgaga ttgccaaggg   1200
actgtttgat gggctggtgt ccctacagct gctcctcctc aatgccaaca agatcaactg   1260
cctgcgggtg aacacgtttc aggacctgca gaacctcaac ttgctctccc tgtatgacaa   1320
caagctgcag accatcagca aggggctctt cgccctctg cagtccatcc agacactcca   1380
cttagcccaa aacccatttg tgtgcgactg ccacttgaag tggctggccg actacctcca   1440
ggacaacccc atcgagacaa gcggggcccg ctgcagcagc ccgcgccgac tcgccaacaa   1500
gcgcatcagc cagatcaaga gcaagaagtt ccgctgctca ggctccgagg attaccgcag   1560
caggttcagc agcgagtgct tcatggacct cgtgtgcccc gagaagtgtc gctgtgaggg   1620
cacgattgtg gactgctcca accagaagct ggtccgcatc ccaagccacc tccctgaata   1680
tgtcaccgac ctgcgactga atgacaatga ggtatctgtt ctggaggcca ctggcatctt   1740
caagaagttg cccaacctgc ggaaaataaa tctgagtaac aataagatca aggaggtgcg   1800
agagggagct ttcgatggag cagccagcgt gcaggagctg atgctgacag gaaccagct   1860 ggagaccgtg cacgggcgcg tgttccgtgg cctcagtggc ctcaaaacct tgatgctgag   1920
gagtaacttg atcagctgtg tgagtaatga cacctttgcc ggcctgagtt cggtgagact   1980
gctgtccctc tatgacaatc ggatcaccac catcacccct ggggccttca ccacgcttgt   2040
ctccctgtcc accataaacc tcctgtccaa ccccttcaac tgcaactgcc acctggcctg   2100
gctcggcaag tggttgagga agaggcggat cgtcagtggg aacccctagg tgccagaagcc   2160 attttcctc aaggagattc ccatccagga tgtggccatc caggacttca cctgtgatgg   2220
caacgaggag agtagctgcc agctgagccc gcgctgcccg gagcagtgca cctgtatgga   2280
gacagtggtg cgatgcagca caagggggct ccgcgccctc cccagaggca tgcccaagga   2340
tgtgaccgag ctgtacctgg aaggaaacca cctaacagcc gtgcccagag agctgtccgc   2400
cctccgacac ctgacgctta ttgacctgag caacaacagc atcagcatgc tgaccaatta   2460
caccttcagt aacatgtctc acctctccac tctgatcctg agctacaacc ggctgaggtg   2520
catccccgtc cacgccttca acgggctgcg gtccctgcga gtgctaaccc tccatggcaa   2580
tgacatttcc agcgttcctg aaggctcctt caacgacctc acatctcttt cccatctggc   2640
gctgggaacc aacccactcc actgtgactg cagtcttcgg tggctgtcgg agtgggtgaa   2700
ggcggggtac aaggagcctg gcatcgcccg ctgcagtagc cctgagccca tggctgacag   2760
gctcctgctc accacccaa cccaccgctt ccagtgcaaa gggccagtgg acatcaacat   2820
tgtggccaaa tgcaatgcct gcctctccag cccgtgcaag aataacggga catgcacccca   2880 ggaccctgtg gagctgtacc gctgtgcctg cccctacagc tacaagggca aggactgcac   2940
tgtgcccatc aacacctgca tccagaaccc ctgtcagcat ggaggcacct gccacctgag   3000
```

```
tgacagccac aaggatgggt tcagctgctc ctgccctctg ggctttgagg ggcagcggtg   3060
tgagatcaac ccagatgact gtgaggacaa cgactgcgaa acaatgcca cctgcgtgga    3120 cgggatcaac aactacgtgt gtatctgtcc gcctaactac acaggtgagc tatgcgacga   3180
ggtgattgac cactgtgtgc ctgagctgaa cctctgtcag catgaggcca agtgcatccc   3240
cctggacaaa ggattcagct gcgagtgtgt ccctggctac agcgggaagc tctgtgagac   3300
agacaatgat gactgtgtgg cccacaagtg ccgccacggg gcccagtgcg tggacacaat   3360
caatggctac acatgcacct gccccaggg cttcagtgga cccttctgtg aacaccccc    3420 acccatggtc ctactgcaga ccagcccatg cgaccagtac gagtgccaga acggggccca   3480
gtgcatcgtg gtgcagcagg agcccacctg ccgctgccca ccaggcttcg ccggccccag   3540
atgcgagaag ctcatcactg tcaacttcgt gggcaaagac tcctacgtgg aactggcctc   3600
cgccaaggtc cgaccccagg ccaacatctc cctgcaggtg gccactgaca aggacaacgg   3660
catccttctc tacaaaggag acaatgaccc cctggcactg gagctgtacc agggccacgt   3720
gcggctggtc tatgacagcc tgagttcccc tccaaccaca gtgtacagtg tggagacagt   3780
gaatgatggg cagtttcaca gtgtggagct ggtgacgcta accagaccc tgaacctagt    3840 agtggacaaa ggaactccaa agagcctggg gaagctccag aagcagccag cagtgggcat   3900
caacagcccc ctctaccttg gaggcatccc cacctccacc ggcctctccg ccttgcgcca   3960
gggcacggac cggcctctag gcggcttcca cggatgcatc catgaggtgc gcatcaacaa   4020
cgagctgcag gacttcaagg ccctcccacc acagtccctg ggggtgtcac caggctgcaa   4080
gtcctgcacc gtgtgcaagc acggcctgtg ccgctccgtg gagaaggaca gcgtggtgtg   4140
cgagtgccgc ccaggctgga ccggcccact ctgcgaccag gaggcccggg acccctgcct   4200
cggccacaga tgccaccatg gaaatgtgt ggcaactggg acctcataca tgtgcaagtg    4260
tgccgagggc tatggagggg acttgtgtga caacaagaat gactctgcca atgcctgctc   4320
agccttcaag tgtcaccatg gcagtgccca catctcagac caaggggagc cctactgcct   4380
gtgccagccc ggctttagcg gcgagcactg ccaacaagag aatccgtgcc tgggacaagt   4440
agtccgagag gtgatccgcc gccagaaagg ttatgcatca tgtgccacag cctccaaggt   4500
gcccatcatg gaatgtcgtg ggggctgtgg gccccagtgc tgccagccca cccgcagcaa   4560
gcggcggaaa tacgtcttcc agtgcacgga cggctcctcg tttgtagaag aggtggagag   4620
acacttagag tgcggctgcc tcgcgtgttc ctaagcccct gcccgcctgc ctgccacctc   4680
tcggactcca gcttgatgga gttgggacag ccatgtggga cccctggtg attcagcatg    4740 aaggaaatga agctggagag gaaggtaaag aagaagagaa tattaagtat attgtaaaat   4800
aaacaaaaaa tagaacttaa aaaaaaaaaa aaaaaaaaa aa                       4842
```

<210> SEQ ID NO 6
<211> LENGTH: 4956
<212> TYPE: DNA
<213> ORGANISM: Artificial
<220> FEATURE:
<223> OTHER INFORMATION: Robo1 gene(AF040990)

<400> SEQUENCE: 6

```
atgaaatgga acatgttcc tttttggtc atgatatcac tcctcagctt atccccaaat     60
cacctgtttc tggcccagct tattccagac cctgaagatg tagagagggg gaacgaccac   120
gggacgccaa tccccacctc tgataacgat gacaattcgc tgggctatac aggctcccgt   180
```

```
cttcgtcagg aagattttcc acctcgcatt gttgaacacc cttcagacct gattgtctca      240
aaaggagaac ctgcaacttt gaactgcaaa gctgaaggcc gccccacacc cactattgaa      300
tggtacaaag ggggagagag agtggagaca gacaaagatg accctcgctc acaccgaatg      360
ttgctgccga gtggatcttt atttttctta cgtatagtac atggacggaa aagtagacct      420
gatgaaggag tctatgtctg tgtagcaagg aattaccttg gagaggctgt gagccacaat      480
gcatcgctgg aagtagccat acttcgggat gacttcagac aaaacccttc ggatgtcatg      540
gttgcagtag gagagcctgc agtaatggaa tgccaacctc cacgaggcca tcctgagccc      600
accatttcat ggaagaaaga tggctctcca ctggatgata aagatgaaag ataactata      660 cgaggaggaa agctcatgat cacttacacc cgtaaaagtg acgctggcaa atatgtttgt      720
gttggtacca atatggttgg ggaacgtgag agtgaagtag ccgagctgac tgtcttagag      780
agaccatcat ttgtgaagag acccagtaac ttggcagtaa ctgtggatga cagtgcagaa      840

tttaaatgtg aggcccgagg tgaccctgta cctacagtac gatggaggaa agatgatgga      900
gagctgccca atccagata tgaaatccga atgatcata ccttgaaaat taggaaggtg      960
acagctggtg acatgggttc atacacttgt gttgcagaaa atatggtggg caaagctgaa     1020
gcatctgcta ctctgactgt tcaagaacct ccacattttg ttgtgaaacc ccgtgaccag     1080
gttgttgctt gggacggac tgtaactttt cagtgtgaag caaccggaaa tcctcaacca     1140
gctattttct ggaggagaga agggagtcag aatctacttt tctcatatca accaccacag     1200

tcatccagcc gattttcagt ctcccagact ggcgacctca caattactaa tgtccagcga     1260

tctgatgttg ttattacat ctgccagact ttaaatgttg ctggaagcat catcacaaag     1320
gcatatttgg aagttacaga tgtgattgca gatcggcctc ccccagttat tcgacaaggt     1380
cctgtgaatc agactgtagc cgtggatggc actttcgtcc tcagctgtgt ggccacaggc     1440
agtccagtgc ccaccattct gtggagaaag gatggagtcc tcgtttcaac ccaagactct     1500
cgaatcaaac agttggagaa tggagtactg cagatccgat atgctaagct gggtgatact     1560
ggtcggtaca cctgcattgc atcaaccccc agtggtgaag caacatggag tgcttacatt     1620
gaagttcaag aatttggagt tccagttcag cctccaagac ctactgaccc aaatttaatc     1680
cctagtgccc catcaaaacc tgaagtgaca gatgtcagca gaaatacagt cacattatcg     1740

tggcaaccaa atttgaattc aggagcaact ccaacatctt atattataga agccttcagc     1800
catgcatctg gtagcagctg gcagaccgta gcagagaatg tgaaaacaga aacatctgcc     1860
attaaaggac tcaaacctaa tgcaatttac cttttccttg tgagggcagc taatgcatat     1920
ggaattagtg atccaagcca aatatcagat ccagtgaaaa cacaagatgt cctaccaaca     1980
agtcaggggg tggaccacaa gcaggtccag agagagctgg gaaatgctgt tctgcacctc     2040
cacaacccca ccgtcctttc ttcctcttcc atcgaagtgc actggacagt agatcaacag     2100

tctcagtata tacaaggata taaaattctc tatcggccat ctggagccaa ccacggagaa     2160

tcagactggt tagtttttga agtgaggacg ccagccaaaa acagtgtggt aatccctgat     2220
ctcagaaagg gagtcaacta tgaaattaag gctcgccctt tttttaatga atttcaagga     2280
gcagatagtg aaatcaagtt tgccaaaacc ctggaagaag cacccagtgc cccaccccaa     2340
ggtgtaactg tatccaagaa tgatggaaac ggaactgcaa ttctagttag ttggcagcca     2400 cctcagaag acactcaaaa tggaatggtc caagagtata aggttgtgtg tctgggcaat     2460
gaaactcgat accacatcaa caaaacagtg atggttccaa ccttttcagt ggtcattccc     2520

tttcttgttc ctggaatccg atacagtgtg gaagtggcag ccagcactgg ggctgggtct     2580
```

```
ggggtaaaga gtgagcctca gttcatccag ctggatgccc atggaaaccc tgtgtcacct    2640
gaggaccaag tcagcctcgc tcagcagatt tcagatgtgg tgaagcagcc ggccttcata    2700
gcaggtattg gagcagcctg ttggatcatc ctcatggtct tcagcatctg gctttatcga    2760
caccgcaaga agagaaacgg acttactagt acctacgcgg gtatcagaaa agtcccgtct    2820
tttaccttca caccaacagt aacttaccag agaggaggcg aagctgtcag cagtggaggg    2880
aggcctggac ttctcaacat cagtgaacct gccgcgcagc catggctggc agacacgtgg    2940
cctaatactg gcaacaacca caatgactgc tccatcagct gctgcacggc aggcaatgga    3000
aacagcgaca gcaacctcac tacctacagt cgcccagctg attgtatagc aaattataac    3060
aaccaactgg ataacaaaca acaaatctg atgctccctg agtcaactgt ttatggtgat     3120
gtggacctta gtaacaaaat caatgagatg aaaaccttca atagcccaaa tctgaaggat    3180
gggcgttttg tcaatccatc agggcagcct actccttacg ccaccactca gctcatccag    3240
tcaaacctca gcaacaacat gaacaatggc agcggggact ctggcgagaa gcactggaaa    3300
ccactgggac agcagaaaca agaagtggca ccagttcagt acaacatcgt ggagcaaaac    3360
aagctgaaca aagattatcg agcaaatgac acagttcctc caactatccc atacaaccaa    3420 tcatcgacc agaacacagg aggatcctac aacagctcag accggggcag tagtacatct     3480
gggagtcagg ggcacaagaa aggggcaaga acacccaagg taccaaaaca gggtggcatg    3540
aactgggcag acctgcttcc tcctccccca gcacatcctc ctccacacag caatagcgaa    3600
gagtacaaca tttctgtaga tgaaagctat gaccaagaaa tgccatgtcc cgtgccacca    3660
gcaaggatgt atttgcaaca agatgaatta gaagaggagg aagatgaacg aggccccact    3720 cccctgttc gggagcagc ttcttctcca gctgccgtgt cctatagcca tcagtccact      3780
gccactctga ctccctcccc acaggaagaa ctccagccca tgttacagga ttgtccagag    3840
gagactggcc acatgcagca ccagcccgac aggagacggc agcctgtgag tcctcctcca    3900
ccaccacggc cgatctcccc tccacatacc tatggctaca tttcaggacc cctggtctca    3960
gatatggata cggatgcgcc agaagaggaa gaagacgaag ccgacatgga ggtagccaag    4020 atgcaaaacca gaaggctttt gttacgtggg cttgagcaga cacctgcctc cagtgttggg    4080
gacctggaga gctctgtcac gggtccatg atcaacggct ggggctcagc ctcagaggag      4140
gacaacattt ccagcggacg ctccagtgtt agttcttcgg acggtccctt tttcactgat    4200
gctgactttg cccaggcagt cgcagcagcg gcagagtatg ctggtctgaa agtagcacga    4260
cggcaaatgc aggatgctgc tggccgtcga cattttcatg cgtctcagtg ccctaggccc    4320
acaagtcccg tgtctacaga cagcaacatg agtgccgccg taatgcagaa aaccagacca    4380
gccaagaaac tgaaacacca gccaggacat ctgcgcagag aaacctacac agatgatctt    4440
ccaccacctc ctgtgccgcc acctgctata aagtcaccta ctgcccaatc caagacacag    4500
ctggaagtac gacctgtagt ggtgccaaaa ctcccttcta tggatgcaag aacagacaga    4560
tcatcagaca gaaaaggaag cagttacaag gggagagaag tgttggatgg aagacaggtt    4620
gttgacatgc gaacaaatcc aggtgatccc agagaagcac aggaacagca aaatgacggg    4680
aaaggacgtg gaaacaaggc agcaaaacga gaccttccac cagcaaagac tcatctcatc    4740
caagaggata ttctacctta ttgtagacct acttttccaa catcaaataa tcccagagat    4800
cccagttcct caagctcaat gtcatcaaga ggatcaggaa gcagacaaag agaacaagca    4860
aatgtaggtc gaagaaatat tgcagaaatg caggtacttg gaggatatga agagggagaa    4920
```

```
gataataatg aagaattaga ggaaactgaa agctga                              4956
```

<210> SEQ ID NO 7
<211> LENGTH: 8393
<212> TYPE: DNA
<213> ORGANISM: Artificial
<220> FEATURE:
<223> OTHER INFORMATION: Robo2 gene (NM_001128929.3)

<400> SEQUENCE: 7

```
agtagcacgg gcagctcgcg cgctggagga gggaggcgga aggacagcgc tgcgccacca     60
cccggaggag ggagcgcggt agctgcaggc aggggaggga gaggaaagaa aaggaaggac    120
ggctcccaga cagagagtgg gagaaaccgg ggagcagcgg gagcagcagg tccgggggga    180
gctgttccgc tgcgctgccc tcgttattca cacggacgct gcggagcttc ccagggctgc    240
ttccctgtcc ccctgggtgg aggctgccgt ctaaacctga ctccagagtt taagatgcaa    300
tggccagaag acatgaacgt gtcactagaa ggatgtggac atgggctccg ggactgttga    360
tgatgactgt ggtgttttgg ggtcatcagg ggaatggaca aggccaagga tcgcgtcttc    420
gccaggagga ctttcccccg cggattgtgg agcatccttc cgatgtcatc gtctctaagg    480
gcgagcccac gactctgaac tgcaaggcg agggccggcc aacgcccacc attgagtggt    540
acaaagatgg ggagcgagtg gagactgaca aggacgatcc ccgtcccac aggatgcttc     600
tgcccagcgg atccttattc ttcttgcgca tcgtgcacgg gcgcaggagt aaacctgatg    660
aaggaagcta cgtttgtgtt gcgaggaact atcttggtga agcagtgagt cgaaatgcgt    720
ctctggaagt ggcattgtta cgagatgact ccgacaaaaa ccccacagat gttgtagtgg    780
cagctggaga gcctgcaatc ctggagtgcc agcctccccg gggacaccca gaacccacca    840
tctactggaa aaaagacaaa gttcgaattg atgacaagga agaagaata agtatccgtg    900
gtggaaaact gatgatctcc aataccagga aaagtgatgc agggatgtat acttgtgttg    960
gtaccaatat ggtgggagaa agggacagtg acccagcaga gctgactgtc tttgaacgac   1020
ccacatttct caggaggcca attaaccagg tggtactgga ggaagaagct gtagaatttc   1080
gttgtcaagt ccaaggagat cctcaaccaa ctgtgaggtg aaaaaggat gatgcagact    1140
tgccaagagg aaggtatgac atcaaagacg attacacact aagaattaaa aagaccatga   1200
gtacagatga aggcaccta t atgtgtattg ctgagaatcg ggttggaaaa atggaagcct   1260
ctgctacact caccgtccga gctccccac agtttgtggt tcggccaaga gatcagattg    1320
ttgctcaagg tcgaacagtg acatttccct gtgaaactaa aggaaaccca gcagcagctg   1380
tttttttggca gaaagaaggc agccagaacc tactttttcc aaaccaaccc cagcagccca   1440
acagtagatg ctcagtgtca ccaactggag acctcacaat caccaacatt caacgttccg   1500
acgcgggtta ctacatctgc caggctttaa ctgtggcagg aagcatttta gcaaaagctc   1560
aactggaggt tactgatgtt ttgacagata gacctccacc tataattcta caaggcccag   1620
ccaaccaaac gctggcagtg gatggtacag cgttactgaa atgtaaagcc actggtgatc   1680
ctcttcctgt aattagctgg ttaaaggagg gatttacttt tccgggtaga gatccaagag   1740
caacaattca agagcaaggc acactgcaga ttaagaattt acggatttct gatactggca   1800
cttatacttg tgtggctaca agttcaagtg agagacttc ctggagtgca gtgctggatg    1860
tgacagagtc tggagcaaca atcagtaaaa actatgattt aagtgacctg ccagggccac   1920
catccaaacc gcaggtcact gatgttacta agaacagtgt caccttgtcc tggcagccag   1980
gtaccccctgg aaccccttcca gcaagtgcat atatcattga ggctttcagc caatcagtga   2040
```

```
gcaacagctg gcagaccgtg gcaaaccatg taaagaccac cctctatact gtaagaggac    2100
tgcggcccaa tacaatctac ttattcatgg tcagagcgat caacccccaa ggtctcagtg    2160
acccaagtcc catgtcagat cctgtgcgca cacaagatat cagcccacca gcacaaggag    2220
tggaccacag gcaagtgcag aaagagctag agatgtcct tgtccgtctt cataatccag     2280
ttgtgctgac tcccaccacg gttcaggtca catggacggt tgatcgccaa ccccagttta    2340
tccaaggcta ccgagtgatg tatcgtcaga cttcaggtct gcaggcgaca tcttcgtggc    2400
agaatttaga tgccaaagtc ccgactgaac gaagtgctgt cttagtcaac ctgaaaaagg    2460
gggtgactta tgaaattaaa gtacggccat attttaatga gttccaagga atggatagtg    2520
aatctaaaac ggttcgtact actgaagaag ccccaagtgc cccaccacag tctgtcactg    2580
tactgacagt tggaagctac aatagcacaa gtattagtgt ttcctgggat cctcctcctc    2640
cagatcacca gaatggaatt atccaagaat acaagatctg gtgtctagga aatgaaacgc    2700
gattccatat caacaaaact gtggatgcag ccattcggtc cgtaataatt ggtggattat    2760
tcccaggtat tcaataccgg gtagaggttg cagctagtac cagtgcaggg gttggagtaa    2820
agagtgagcc acagccaata ataatcggga gacgcaatga agttgtcatt actgaaaaca    2880
ataacagcat aactgagcaa atcactgatg tggtgaagca accagccttt atagctggta    2940
ttggtggtgc ctgctgggta attctgatgg gttttagcat atggttgtat tggcgaagaa    3000
agaagaggaa gggactcagt aattatgctg ttacgtttca aagaggagat ggaggactaa    3060
tgagcaatgg aagccgtcca ggtcttctca atgctggtga tcccagctat ccatggcttg    3120
ctgattcttg gccagccacg agcttgccag taaataatag caacagtggc ccaaatgaga    3180
ttggaaattt tggccgtgga gatgtgctgc caccagttcc aggccaaggg gataaaacag    3240
caacgatgct ctcagatgga gccatttata gtagcattga cttcactacc aaaaccagtt    3300
acaacagttc cagccaaata acacaggcta ccccatatgc cacgacacag atcttgcatt    3360
ccaacagcat acatgaattg gctgtcgatc tgcctgatcc acaatggaaa agctcaattc    3420
agcaaaaaac agatctgatg ggatttggtt attctctacc tgatcagaac aaaggtaaca    3480
atggtgggaa aggtggaaaa agaagaaaaa taaaaactc ttctaaacca cagaaaaaca    3540
atggatccac ttgggccaat gtccctctac ctccccccc agtccagccc cttcctggca    3600
cggagctgga acactatgca gtggaacaac aagaaaatgg ctatgacagt gatagctggt    3660
gcccaccatt gccagtacaa acttacttac accaaggtct ggaagatgaa ctggaagaag    3720
atgatgatag ggtcccaaca cctcctgttc gaggcgtggc ttcttctcct gctatctcct    3780
ttggacagca gtccactgca actcttactc catccccacg ggaagagatg caacccatgc    3840
tgcaggctca cctggatgag ttgacaagag cctatcagtt tgatatagca aaacaaacat    3900
ggcacattca aagcaataat caacctccac agcctccagt tccaccgtta ggttatgtgt    3960
ctggagcctt gatttctgat ttggaaacga tgttgcaga tgatgatgcc gacgacgaag     4020
aggaagcttt agaaatcccc aggcccctga gcactggga ccagactcct ggatccagca     4080
tggacaatct agacagctct gtgacaggaa aagcctttac ctcctctcaa agacctcgac    4140
ctaccagccc attttctact gacagtaaca ccagtgcagc cctgagtcaa agtcagaggc    4200
ctcggcccac taaaaaacac aagggagggc ggatggacca acaaccagca ttgcctcatc    4260
gaagggaagg aatgacagat gaggaggcct tggtgcccta tagcaagccc agtttcccat    4320
ctccaggtgg ccacagctca tcaggaacag cttcttctaa gggatccact ggacctagga    4380
```

```
aaaccgaggt gttgagagca ggccaccagc gcaatgccag cgaccttctt gacataggat    4440
atatgggctc caacagtcaa ggacagttta caggtgaatt atagtaaatg agaggagaca    4500
tacaaagctg ctctgaagga ccatcaggtc cggactcatg gaagtgatga ctctaaacag    4560
tgcaatgaac aatttattta tgtactatta aagaactgt aaatgcaatg taaagacaca     4620
cagccacaca tatcccacag atattttcat tgtgttcttc tcttaagtac accacccacc    4680
ttaactcttt cttgtcagga gtatataaaa agaaagaaa acaaaactcg ccctacagga     4740
agaaaaggat tctcctctgt atataaattc ttttgtgcat tgctatgcaa gctcactctt    4800
tttagctctg ctcatattat tgtctgttct tattggtctg ttgtactata tgtgaattaa    4860
taggctgtgg tgccatatat taacttttaa ttgtgtaact tttatgttta aattttgcac    4920
tgcaatttta tttggtgata agcacaaatc tctactcctc atgacatgaa gaaaagact     4980 gaatgtgaag ggagtttctg tactgtaagc tagattggat aatgatggct gtaacaaatc    5040
atgttagatg gttttcagtt ggggtgtaga aataggaaga tgcaaaggaa caatggtgtt    5100
ggcaaagtct tctttgaata tcagggactg agtcaataaa aaaatagta gaaaggtggc     5160 ttttactatt gacaaaagcc ggggtcaaaa aaagtagttt aagtcttaag actgaatatg    5220
cattaaagta tgcaggtagc aaagatgtaa taaatttgct taaaaaaga aattaaagtt     5280 ttatttagaa tcaattttac ctgtcattgt aattgaccca tctgagaatt acaataagca    5340
agaggaaatt aaggtgtttt gcaagagctg tatttatatt acagttttt aaaaacattt     5400 tctgaattat cgtaattaag ctctccaact cgttaagtca gaatataata tgaagttccc    5460
caaggaaacg aacaaaatga actctagaat atctagcaaa tagttaaaga agcaatttat    5520
tattagggca tactcgggct gttt ccaaat ataaactcta ttgcaatatc ttatttcatc   5580
tttctaatac atgtacagtg cacactagag gatagagctg catcacttaa attcatgact    5640
taaaaaataa tacagtttat ataca acttg ttttttattt gattaagaag tgaagtttac   5700
gccacccaat gtatagccaa attgtacgtg cttaaaaaac agtgccgaga gtatgttcag    5760
ttcgcagtaa gtagatttat tggaataaat attctatggt acattctcag aaattggctt    5820
ccaactaaaa tacgtttgac ccattttgaa taaggaaatt gaaagaaaa atttaaaagg     5880 agaaaaaaat gcatgtttat aaacttttta aataaaacca gaccttgtaa gtggacatta    5940
ataattgtcc tgcctcattt gttttcacga ctttgacaac aagaagttcc tgaacattag    6000
tcatgtatgc tcagaataaa tgtgactttg aaatatatgt tagctactgt acatgtatag    6060
tcagtcaagt agaagaggac cttcctgaaa ttcccacttg tgacattttc ccatgggttt    6120
cctacacaat cttaaatttt atttctgtct atactttctc aaattttcc tatgataagt     6180 tcagttgttg gtactcttct aaaaatattc aacgtgatta ggatcagttc taaaatacgg    6240 gaccctttg agtgacaatt cgcactccat gcattattgg ctcagtagcc aattttgtc      6300 acgtcgttat aacaaggaga tgacataatt aaacatttcc atcctttcta ttccctgaga    6360
ctgcatcagc acaggcaagt atagaatgta atgttcttca tgggcccac cagcttttg      6420 gtgccatgta atttatttct tcgctgaaga gaaaagaat tctgagacac agttattaaa     6480 cccctttatca actttctacc atcagtgcct gaattctaat gcagtgtgat ttctctggga   6540
caaagagact gaggaagatg aaaagtttct tcaaagagtg aatacatact tattcacaac    6600
tctaggatgt gaggacttta aatatctctt tatgaagttc cctgcctaac ctctttctat    6660
ttaaaggcaa acaaatttcg aagaggtttt gtgttccctc tttatgtttc tctatgaccc    6720
agtttagtct aaaaccttag ttcattacat atacaacaca tagcctttga tccctggtaa    6780
```

```
ctggcaggtg ttggtgatta ataaaccaag gcttcaaagt gaagtatgtg tgtgcagatg    6840
acttttggaa taacgtgggc atagcatcat accttcctga ttgtcttcag catataaaaa    6900
ttaactgttg tagttaaaat tatgtcagtg cagagcttgt ggttacttgg aatgttcttt    6960
cagaatagtc catgttgcct attaaaccta gttttaaaca cattgggcag tcaatttatg    7020
cacccaaaat atcaccctca ggtagattga gggcaagata aaatgctgta tgtagctata    7080
caaaggaatt cagaaacatt actggaaagc aaagcctttg tcagcttgct actgacaaag    7140
tagtaaaaag ctactaatca gtgttgagtc agatgtcaac agaaaaatac aaataccta     7200 gagagccaca gcagtttctc gtttcatagc cgattcaatg aatatgatta gaaattcact    7260
gagctcactc ttgcaggttt aaatggaggc ctgcataagg actgcaagag gaaatctggg    7320
tgggagagaa tgtaatctga tcttgcactc ataggcaatg ctgcaatgca atcatgtcca    7380
atacaagcac agcttcattc ataacaggaa acgtcttctt tgggaaaata gctctattgg    7440
tgcccaaact caggtatgcc agtgtatgca ggtggagtcg ccctacccct cttccaaaca    7500
tgtcctgtga gattttttaaa ataagatggg atagtacagg ggcatgaaaa gaattgattc    7560
cttcacagga tttgaatcca gttcaaggga gaatgtagaa aattcaaaac caacatataa    7620
ggtatcacac aaccaagaaa agtaaaacca ttgcaagttt acttgcgttg agtacaaaac    7680
agatttaatg gtgttctatg tcatagttta atgctctggg tatttaaata tgttttcaac    7740
aggatttgag ttgaaagttt gtaatgtgct ttgatggaac acctctcaat ttctattcaa    7800
taaacttatg taattgtcca ttgacaatat aatgataaca gtaccattga actctaaact    7860
gtggtttatc ttcactactg ggaagcaact gtgcatcagt attaaagata tgcagaaaca    7920
taatattcac taatttgttc atctgcttct gtatattgtt tatggaatta catggcaaga    7980
actgttctaa agcaacatgt cttccacat tattttagag gtgaaattac ttttgttttg    8040
cttctctata atgtgtactt caaatgaaac accatacttt tttctaaaaa aagatgttca    8100
atttactaat tttttttaaat ctcataattt aaaaagcatt tgttgtgatt ttaaagtgtt    8160
gcaagaaaag ggattttgtg gccgtgggta gactttttat actttgtttt atagatggat    8220
tttttttaac tgtagtttgt ttaagtcacc aagcagcatc caaaatctta atgtgtttca    8280
tttgatgttg ttagatcaga gaagaaattg gcataaaatc ggttaatagt attgtcaaag    8340
aattgtgtat tgtgtactca ctgggaaaaa ataaaatata ttcacattc aaa            8393
```

<210> SEQ ID NO 8
<211> LENGTH: 390
<212> TYPE: DNA
<213> ORGANISM: Artificial
<220> FEATURE:
<223> OTHER INFORMATION: LRRD2 gene

<400> SEQUENCE: 8

```
atcgtcgaaa tacgcctaga acagaactcc atcaaagcca tccctgcagg agccttcacc      60
cagtacaaga aactgaagcg aatagacatc agcaagaatc agatatcgga tattgctcca     120
gatgccttcc agggcctgaa atcactcaca tcgctggtcc tgtatgggaa caagatcacc     180
gagattgcca agggactgtt tgatgggctg gtgtccctac agctgctcct cctcaatgcc     240
aacaagatca actgcctgcg ggtgaacacg tttcaggacc tgcagaacct caacttgctc     300
tccctgtatg acaacaagct gcagaccatc agcaaggggc tcttcgcccc tctgcagtcc     360
atccagacac tccacttagc ccaaaaccca                                     390
```

METHOD USING SLIT-ROBO SYSTEM TO TREAT SARCOPENIA

TECHNICAL FIELD

The present application claims priority to and the benefit of Korean Patent Application Nos. 10-2016-0071252 and 10-2017-0013799 filed in the Korean Intellectual Property Office on Jun. 8, 2016 and Jan. 31, 2017, respectively, the entire contents of which are reference documents of the present application.

The present invention relates to a composition using a SLIT-ROBO system for preventing or treating sarcopenia and, more specifically, to a composition comprising a gene selected from among slit1, slit2, slit3, robo1, robo2, and fragments thereof, or a protein expressed from the gene; and/or an activator thereof as an effective ingredient for preventing or treating a muscle disease or for improving muscular function.

BACKGROUND ART

A slit protein is a well-known protein that regulates the movement of neurons and axons during the developmental process of the nervous system. It was known that a Slit protein could interact with a Robo receptor to regulate physiological activity, and serves as a factor that regulates various intracellular processes in various tissues such as heart, lung, kidney, and breast tissues, and as it has been recently reported that a Slit protein plays an important role in the regulation of growth, adhesion ability, and migration ability of cells, it was reported that a Slit protein can participate in the migration in the differentiation of cells and the occurrence and metastasis of cancer. Specifically, it was reported that a Slit protein and a Robo protein are expressed at the embryonic development stage of a vertebrate, and the expression of Slit3, Robo1 and Robo2 proteins is increased in the muscle tissues. The report mentioned that the expression of a Slit3 protein was increased in the myoblasts of hind leg muscle tissues of an embryo, but the protein only might participate in the migration ability and might not be associated with the differentiation of myoblasts.

A human Robo protein is present in the four forms of Robo1, Robo2, Robo3, and Robo4. It was reported that Slit and Robo could play various roles depending on what subtypes bind to each other, but since the role may vary depending on the expressed cells, studies have been actively conducted until now. In this regard, Korean Patent No. 10-1617497 describes that a Slt3 protein can interact with Robo1 or Robo2 to exhibit activity, can induce the differentiation of osteoblasts through the activity, and can increase osteogenesis.

Sarcopenia refers to a condition in which the amount and function of skeletal muscles are reduced. Sarcopenia occurs for various reasons such as aging, hormonal disorders, malnutrition, insufficient physical activity, inflammation and degenerative diseases, and among them, it is known that aging and a lack of sex hormones may be the main reasons for sarcopenia, and as the average life expectancy is increasing globally due to the advancement in medical technology and the development of various therapeutic agents, the aging population is increasing, and accordingly, it is expected that the demand for treatment of sarcopenia will also be continuously increased.

In patients with sarcopenia, due to the disorder in recruitment, activity or proliferation of satellite cells, which are stem cells of myoblasts, the number of myoblasts is decreased and the proliferation and differentiation of myoblasts are decreased, and accordingly, for the muscles of patients with sarcopenia, the size and number of muscle fibers are decreased at the histological level, so that symptoms in which the muscular functions are decreased occur.

As studies on the mechanism of sarcopenia have been actively conducted mainly in the United States and Europe over the past ten years, interest in the clinical importance of sarcopenia has been rapidly increased. In the early studies, the results showed that general weakening, dysfunction and muscle weakness causing deterioration in quality of life accounted for the most part of sarcopenia, but studies recently released have reported that the risk of osteoporotic fracture may be notably increased in addition to the quality of life. Further, chronic diseases such as diabetes and metabolic syndrome, obesity, chronic renal failure, and chronic liver failure are caused in patients with sarcopenia, and ultimately, the mortality rate is also increased, so that sarcopenia has drawn attention as a disease to be appropriately treated.

In the United States, it has been recently reported that the possibility of physical disability in patients with sarcopenia is increased about 1.5 times to about 3.5 times, and as a result, a social cost of 18.5 billion USD per year is caused. According to the Korea National Health and Nutrition Examination Survey, the prevalence of sarcopenia is 42.0% and 42.7% in males and females over 60, respectively, so that sarcopenia is a very common disease, and in particular, it is certain that sacropenia will be an important social issue in the future because Korea has the highest aging rate in the world.

Currently, it is known that exercise, protein and calorie supplementation are useful for sarcopenia, but these therapies are not very useful for the elderly who account for the majority of patients with sarcopenia, so that there is an urgent need for a therapeutic agent against sarcopenia. However, with respect to therapeutic agents currently used against sarcopenia, drugs exhibiting a direct effect on amelioration of muscle loss and enhancement of muscle mass are still at the clinical trial stage, and currently, there is no medicine finally approved by the FDA. For this reason, efforts have been made to develop some of a selective androgen receptor, an activin receptor antagonist, a fast skeletal muscle troponin inhibitor, and the like as therapeutic agents for sarcopenia in order to treat sarcopenia, but the efforts are currently at the stage of initial clinical trials.

According to reports on trends in the therapeutic agent against sarcopenia, it was reported that the global market of the therapeutic agent against sarcopenia was about $10 million (US) in 2010 and would grow to the $20 million (US) scale in 2018 ("Sarcopenia Therapeutics—Pipeline Assessment and Market Forecasts to 2018", 2011 Nov. 17). Further, the Innovative Medicines Initiative which is a private conservation cooperative body under the EU in 2013 announced that the institute would invest about 50 million euros in the development of a therapeutic agent against elderly sarcopenia as one of the four major health research themes, and the investment project is underway.

Thus, the present inventors made intensive efforts to develop a therapeutic agent capable of directly exhibiting therapeutic effects on sarcopenia, and as a result, the present inventors confirmed that the muscle masses were decreased in Slit protein-deficient mice, a Slit protein binding to a Robo1 or Robo2 receptor, and as a result, the β-catenin binding to the M-cadherin of myoblasts was released via the Slit-Robo system to activate the β-catenin and increase the expression of myogenin, and subsequently, the formation of muscles could be promoted by inducing the differentiation of myoblasts. In addition, in particular, the present inventors confirmed that not only in the case of treatment of a full-length Slit protein, but also when a LRRD2 protein, which is an active fragment thereof, was treated, an increase in muscle mass could be induced by promoting the differentiation of myoblasts, and as a result, a Slit protein, a Robo protein, active fragments thereof, or genes encoding the same could be used as an effective ingredient of a composition for preventing and treating/alleviating sarcopenia, thereby completing the present invention.

PRIOR ART DOCUMENT (Patent Document 1) KR10-1617497 B1

DISCLOSURE

Technical Problem

As described above, the present inventors confirmed that a Slit protein binding to a Robo1 or Robo2 receptor, and as a result, the β-catenin binding to the M-cadherin of myoblasts was released via the Slit-Robo system to activate the β-catenin and increase the expression of myogenin, and subsequently, the formation of muscles could be promoted by inducing the differentiation of myoblasts. Furthermore, the present inventors confirmed that not only in the case of treatment of a full-length Slit protein, but also when an active fragment thereof was treated, an increase in muscle mass could be induced by promoting the differentiation of myoblasts, thereby completing the present invention.

Accordingly, an object of the present invention is to provide a pharmaceutical composition for preventing and treating a muscle disease.

Another object of the present invention is to provide a health functional food or feed additive for preventing and alleviating a muscle disease.

Still another object of the present invention is to provide a cosmetic composition for improving muscular function.

Yet another object of the present invention is to provide a method for detecting a protein for providing information on diagnosis of a muscle disease.

Still yet another object of the present invention is to provide a method for screening a therapeutic agent against a muscle disease.

Technical Solution

In order to achieve the objects, the present invention provides a pharmaceutical composition for preventing and treating a muscle disease, including one protein selected from the group consisting of Slit1, Slit2, Slit3, Robo1, Robo2, and fragments thereof, or a gene encoding the same; and an activator thereof, as an effective ingredient.

A preferred embodiment of the present invention provides a pharmaceutical composition for preventing and treating a muscle disease, including one protein selected from the group consisting of amino acid sequences of the following SEQ ID Nos. 1 to 4, or a gene encoding the same, as an effective ingredient:

a Slit3 protein consisting of an amino acid of SEQ ID No. 1;

a Robo1 protein consisting of an amino acid of SEQ ID No. 2;

a Robo2 protein consisting of an amino acid of SEQ ID No. 3; and a LRRD2 protein consisting of an amino acid of SEQ ID No. 4.

Further, the present invention provides a method for treating a muscle disease, the method including the steps of: administering one protein selected from the group consisting of Slit1, Slit2, Slit3, Robo1, Robo2, and fragments thereof, or a gene encoding the same to an individual in need thereof.

In addition, the present invention provides a method for treating a muscle disease, the method including the steps of: administering one protein selected from the group consisting of the amino acid sequences of SEQ ID Nos. 1 to 4, or a gene encoding the same to an individual in need thereof.

Furthermore, the present invention provides a method for treating a muscle disease, the method including the steps of: administering an activator of one protein selected from the group consisting of Slit and fragments thereof, or a gene encoding the same to an individual in need thereof.

Further, the present invention provides a method for treating a muscle disease, the method including the steps of: administering an activator of one protein selected from the group consisting of Robo and fragments thereof, or a gene encoding the same to an individual in need thereof.

In addition, the present invention provides a use of one protein selected from the group consisting of Slit1, Slit2, Slit3, Robo1, Robo2, and fragments thereof, or a gene encoding the same for a pharmaceutical composition for preventing and treating a muscle disease.

Furthermore, the present invention provides a use of one protein selected from the group consisting of the amino acid sequences of SEQ ID Nos. 1 to 4, or a gene encoding the same for a pharmaceutical composition for preventing and treating a muscle disease.

Further, the present invention provides a use of an activator of one protein selected from the group consisting of Slit and fragments thereof, or a gene encoding the same for a pharmaceutical composition for preventing and treating a muscle disease.

In addition, the present invention provides a use of an activator of one protein selected from the group consisting of Robo and fragments thereof, or a gene encoding the same for a pharmaceutical composition for preventing and treating a muscle disease.

Furthermore, the present invention provides a health functional food for preventing and alleviating a muscle disease, including one protein selected from the group consisting of Slit1, Slit2, Slit3, Robo1, Robo2, and fragments thereof, or a gene encoding the same; or an activator thereof, as an effective ingredient.

Further, the present invention provides a use of one protein selected from the group consisting of Slit1, Slit2, Slit3, Robo1, Robo2, and fragments thereof, or a gene encoding the same; or an activator thereof for a health functional food for preventing and alleviating a muscle disease.

In addition, the present invention provides a use of one protein selected from the group consisting of the amino acid sequences of SEQ ID Nos. 1 to 4, or a gene encoding the same for a health functional food for preventing and alleviating a muscle disease.

A preferred embodiment of the present invention provides a health functional food for preventing and alleviating a muscle disease, including one protein selected from the group consisting of the amino acid sequences of SEQ ID Nos. 1 to 4, or a gene encoding the same, as an effective ingredient.

Furthermore, the present invention provides a cosmetic composition for improving muscular function, including one protein selected from the group consisting of Slit1, Slit2, Slit3, Robo1, Robo2, and fragments thereof, or a gene encoding the same; or an activator thereof, as an effective ingredient.

Further, the present invention provides a use of one protein selected from the group consisting of Slit1, Slit2, Slit3, Robo1, Robo2, and fragments thereof, or a gene encoding the same; or an activator thereof for a cosmetic composition for improving muscular function.

In addition, the present invention provides a use of one protein selected from the group consisting of the amino acid sequences of SEQ ID Nos. 1 to 4, or a gene encoding the same for a cosmetic composition for improving muscular function.

A preferred embodiment of the present invention provides a cosmetic composition for improving muscular function, including one protein selected from the group consisting of the amino acid sequences of SEQ ID Nos. 1 to 4, or a gene encoding the same, as an effective ingredient.

Furthermore, the present invention provides a feed additive for improving muscular function, including one protein selected from the group consisting of Slit1, Slit2, Slit3, Robo1, Robo2, and fragments thereof, or a gene encoding the same; or an activator thereof, as an effective ingredient.

Further, the present invention provides a use of one protein selected from the group consisting of Slit1, Slit2, Slit3, Robo1, Robo2, and fragments thereof, or a gene encoding the same; or an activator thereof for a feed additive for improving muscular function.

In addition, the present invention provides a use of one protein selected from the group consisting of the amino acid sequences of SEQ ID Nos. 1 to 4, or a gene encoding the same for a feed additive for improving muscular function.

A preferred embodiment of the present invention provides a feed additive for improving muscular function, including one protein selected from the group consisting of the amino acid sequences of SEQ ID Nos. 1 to 4, or a gene encoding the same, as an effective ingredient.

According to a preferred embodiment of the present invention, the Slit3 protein may be expressed from a slit3 gene consisting of a base sequence of SEQ ID No. 5.

According to a preferred embodiment of the present invention, the Robo1 protein may be expressed from a robo1 gene consisting of a base sequence of SEQ ID No. 6.

According to a preferred embodiment of the present invention, the Robo2 protein may be expressed from a robo2 gene consisting of a base sequence of SEQ ID No. 7.

According to a preferred embodiment of the present invention, the LRRD2 protein may be expressed from a gene consisting of a base sequence of SEQ ID No. 8.

According to another preferred embodiment of the present invention, the muscle disease may be a muscle disease caused by muscular function deterioration, muscle wasting, or muscle degeneration, and the muscle degeneration may be one or more selected from the group consisting of atony, muscular atrophy, muscular dystrophy, muscle degeneration, myasthenia, cachexia, and sarcopenia.

In addition, the present application provides a method for detecting a protein for providing information on diagnosis of a muscle disease, the method including the steps of:
    i) measuring an expression level of a Slit3 protein consisting of an amino acid sequence of SEQ ID No. 1 from a subject-derived sample which is an experimental group;
    ii) comparing the expression level of the Slit3 protein measured in Step i) with an expression level of a Slit3 protein of a normal individual-derived sample which is a control group; and
    iii) determining the experimental group as a muscle disease when the expression level of the Slit3 protein of the experimental group compared in Step ii) is decreased as compared to that of the control group.

Furthermore, the present invention provides a method for screening a therapeutic agent against a muscle disease, the method including the steps of:
    i) treating a cell line expressing one or more selected from the group consisting of a Slit3 protein consisting of an amino acid sequence of SEQ ID No. 1, a Robo1 protein consisting of an amino acid sequence of SEQ ID No. 2, and a Robo2 protein consisting of an amino acid sequence of SEQ ID No. 3 with a subject compound or composition;
    ii) measuring an expression degree of the Slit3 protein or activity of the Robo1 protein or Robo2 protein in the cell line treated in Step i); and
    iii) selecting a subject compound or composition in which the expression degree of the Slit3 or the activity of the Robo1 protein or Robo2 protein in Step ii) is increased in comparison with that of the control group cell line which is not treated with the subject compound or composition.

Advantageous Effects

The present invention can provide a composition for preventing or treating sarcopenia, using a SLIT-ROBO system. In particular, the present invention can provide a composition for preventing and treating a muscle disease, or improving muscular function, containing a gene selected from slit1, slit2, slit3, robo1, robo2, and fragments thereof, or a protein expressing the same; or an activator thereof.

In particular, specifically, the Slit protein of the present invention can bind to a Robo1 or Robo2 receptor to release the β-catenin binding to the M-cadherin of myoblasts via the Slit-Robo system, thereby promoting the formation of muscles by activating the bound β-catenin and increasing the expression of myogenin to induce the differentiation of myoblasts. Further, not only in the case of treatment of a full-length Slit protein, but also when an active fragment thereof, particularly preferably, a LRRD2 protein is treated, an increase in muscle mass can be induced by promoting the differentiation of myoblasts, so that the Slit protein or Robo protein of the present invention, an active fragment thereof, or a gene encoding the same can be used as an effective ingredient of a pharmaceutical composition for preventing and treating sarcopenia, and thus is effective.

DESCRIPTION OF DRAWINGS

FIG. 11 is a set of views confirming the types and expression levels of cadherin proteins expressed in myoblasts:

FIG. 12 is a set of views confirming a myoblast differentiation-inducing effect of Slit3 by β-catenin activation.

FIG. 13 is a set of views confirming a Robo receptor subtype binding to Slit3 in myoblasts:

FIGS. 16A to 16E illustrate confirmation of effects of changes in body weight and increases in sarcopenic indices of Slit3 by LRRD2 at the in vivo level.

MODES OF THE INVENTION

Figure 1A:
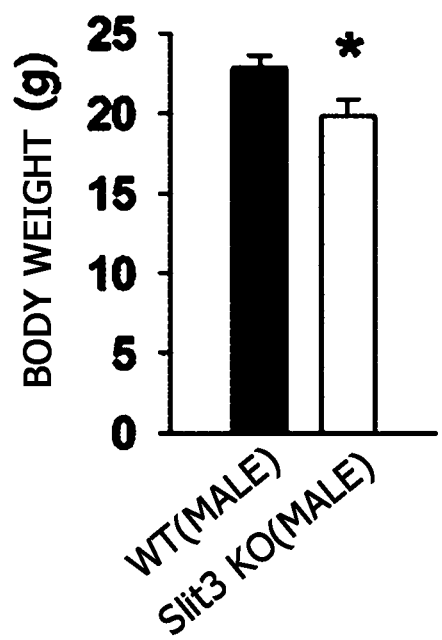
FIGS. 1A to 1E illustrate changes in body weight and sarcopenic indices in Slit3-deficient male mouse model groups.
Figure 1B:
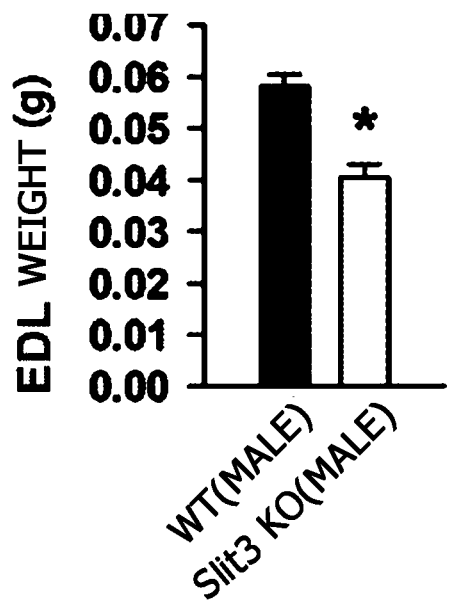
Figure 1C:
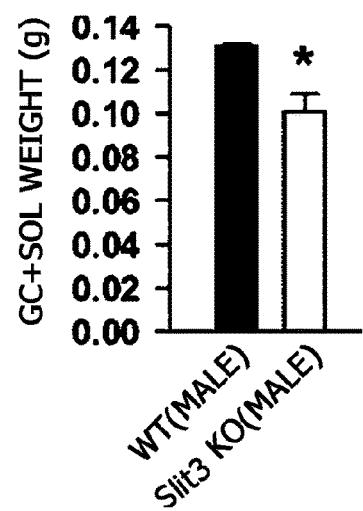
Figure 1D:
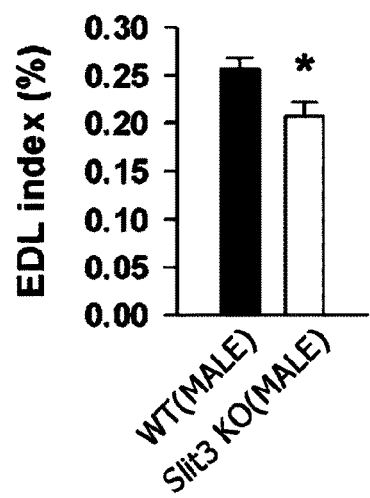
Figure 1E:
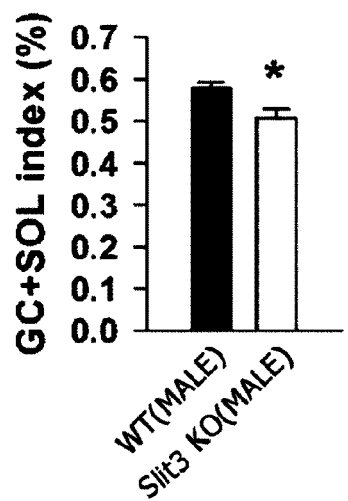
Figure 2A:
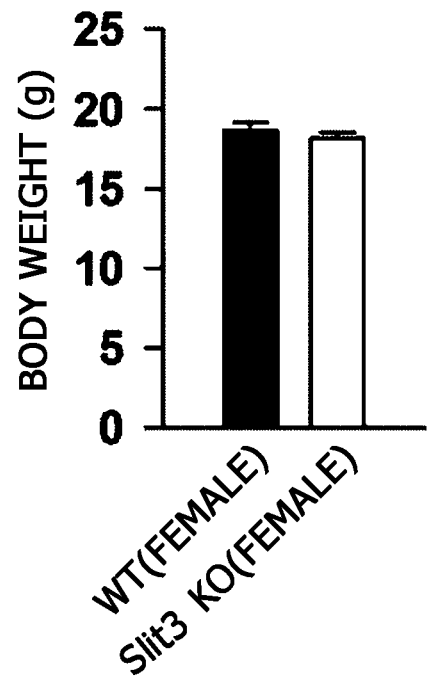
FIGS. 2A to 2E illustrate changes in body weight and sarcopenic indices in Slit3-deficient female mouse model groups.
Figure 2B:
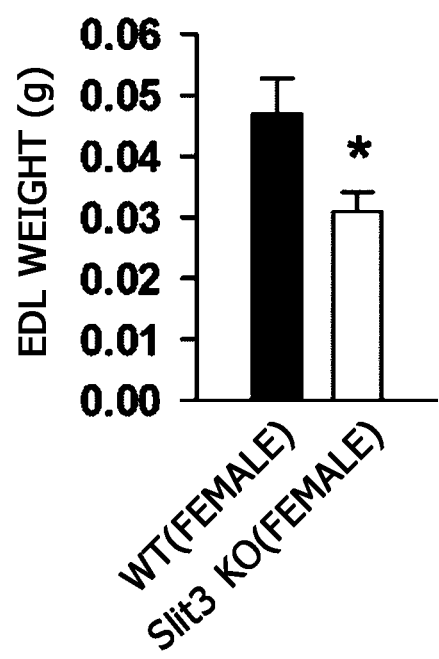
Figure 2C:
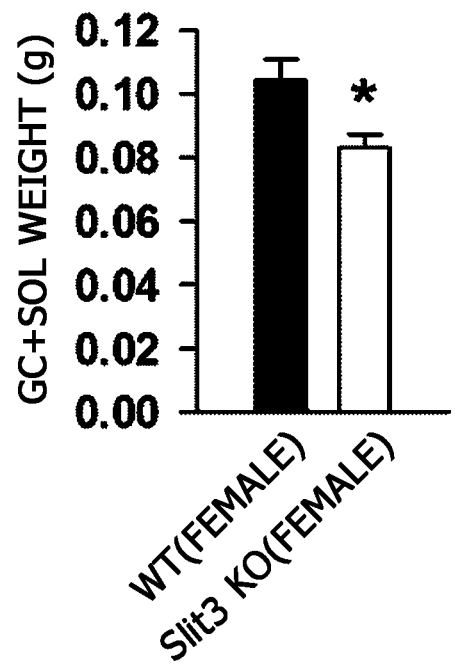
Figure 2D:
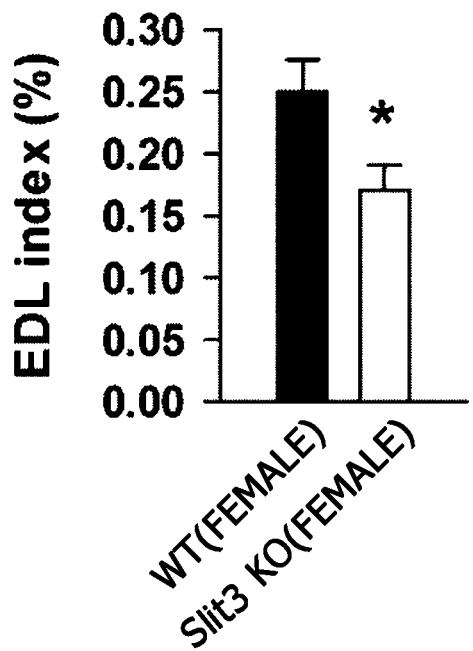
Figure 2E:
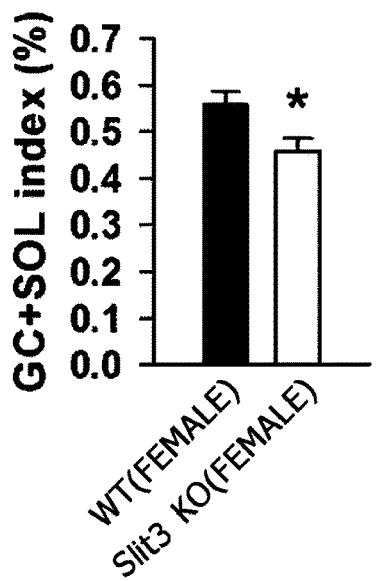
Figure 3A:
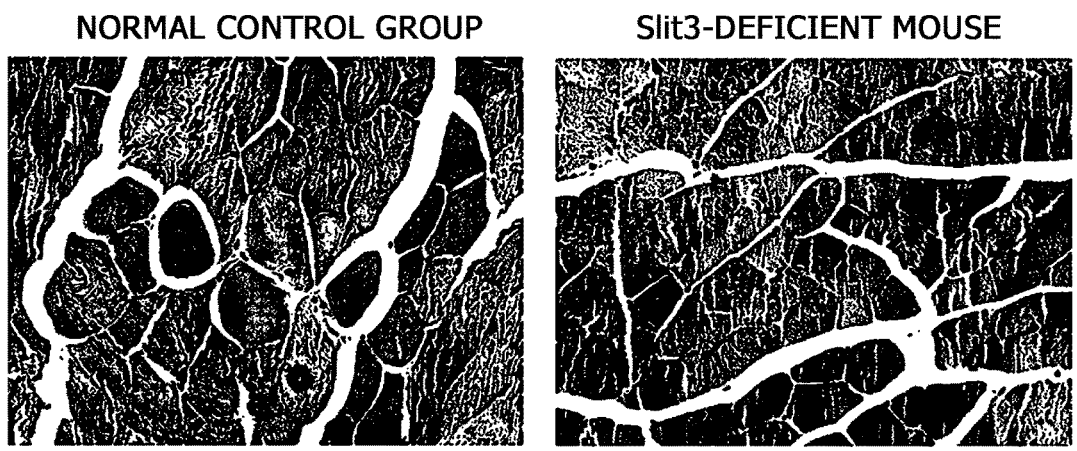
FIGS. 3A to 3D illustrate H&E staining results of EDL muscles of Slit3-deficient male mouse model groups.
Figure 3B:
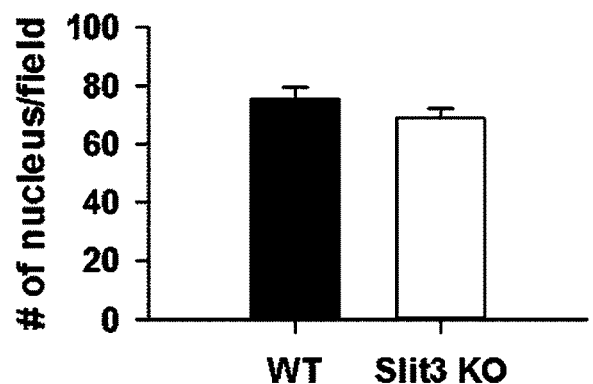
Figure 3C:
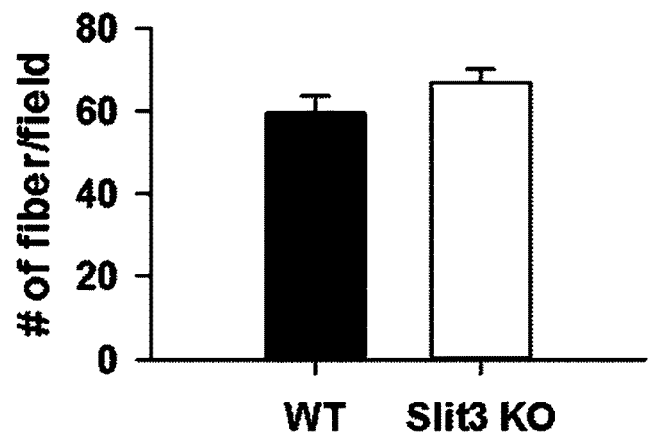
Figure 3D:
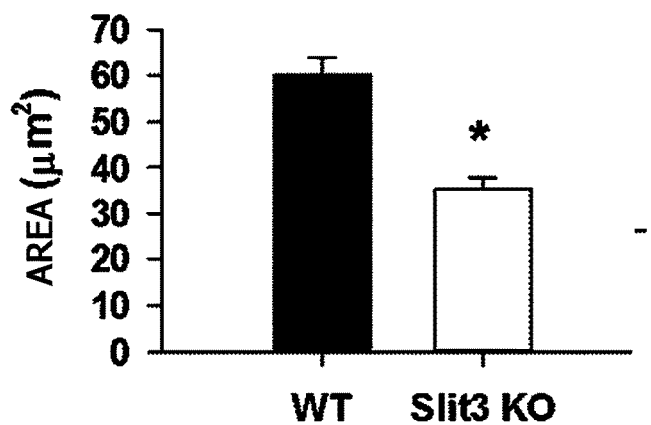
Figure 4A:
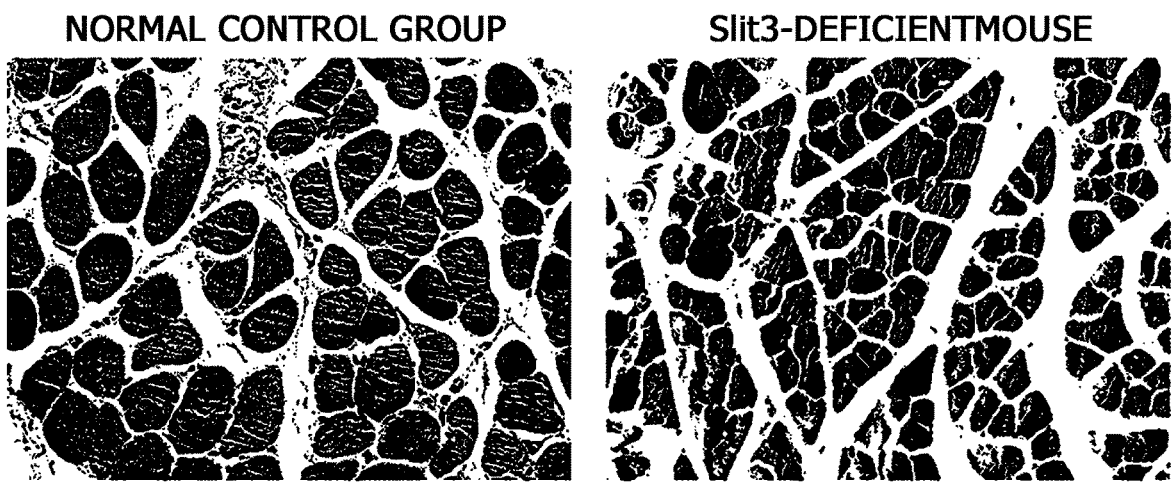
FIGS. 4A to 4D illustrate H&E staining results of GC muscles of Slit3-deficient male mouse model groups.
Figure 4B:
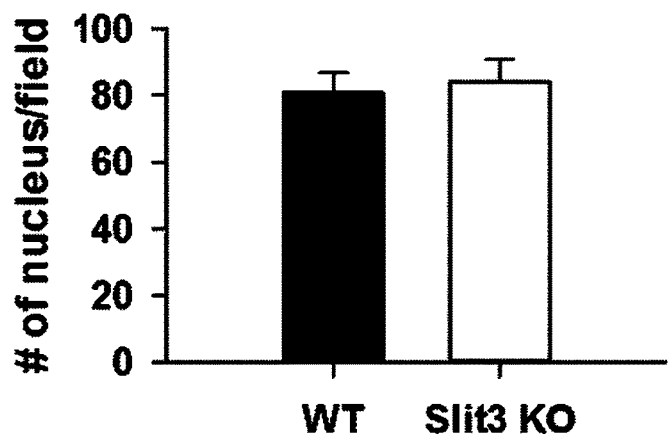
Figure 4C:
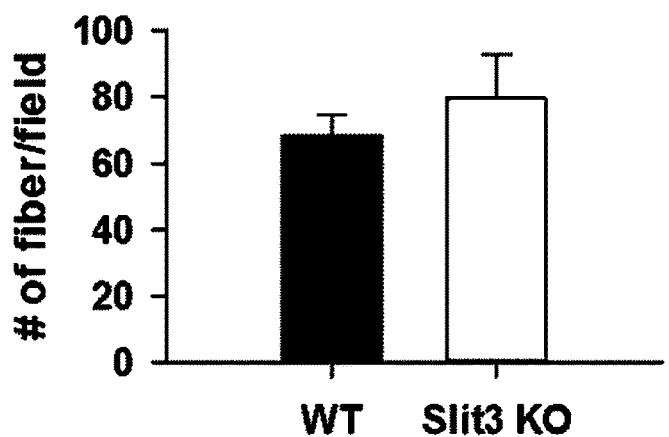
Figure 4D:
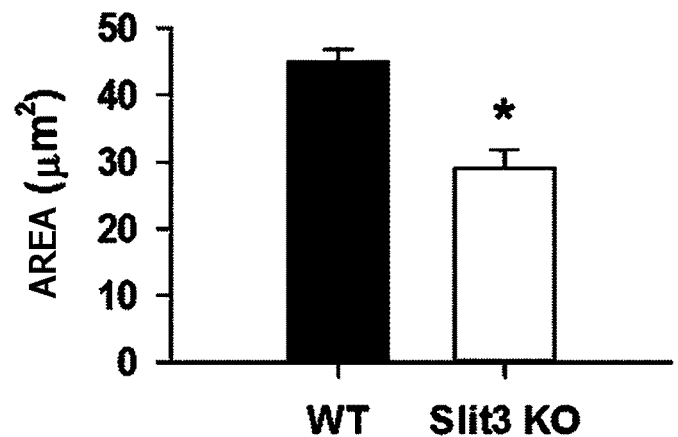
Figure 5A:
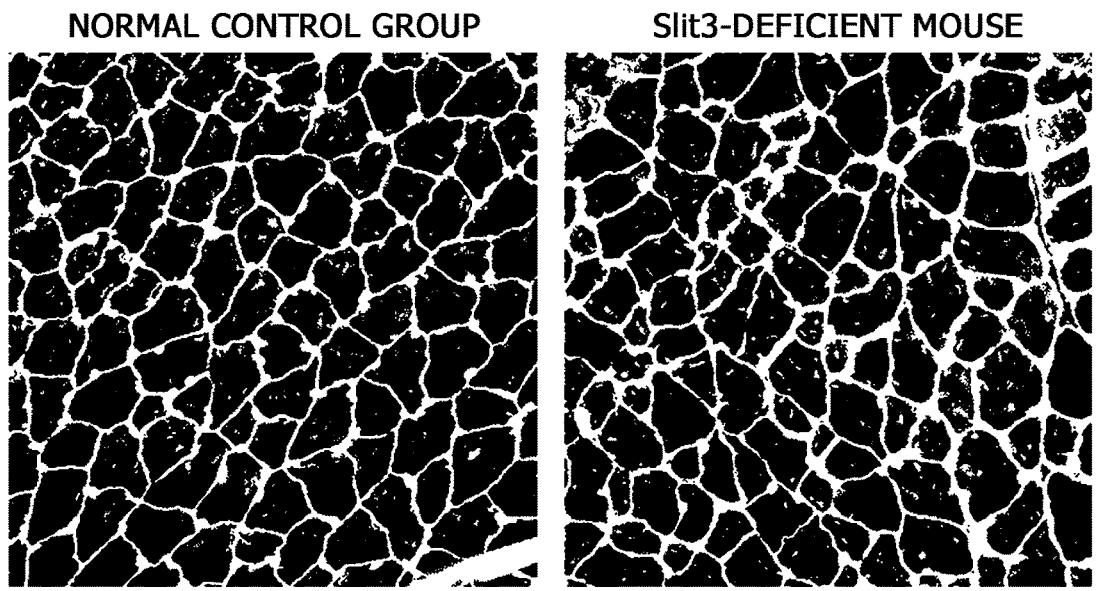
FIGS. 5A to 5D illustrate immunohistochemical staining results of GC muscles of Slit3-deficient male mouse model groups.
Figure 5B:
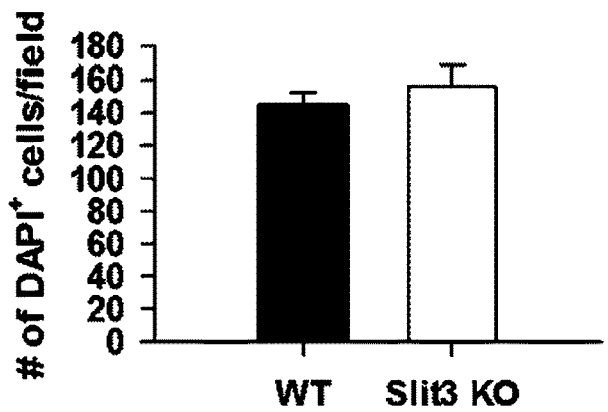
Figure 5C:
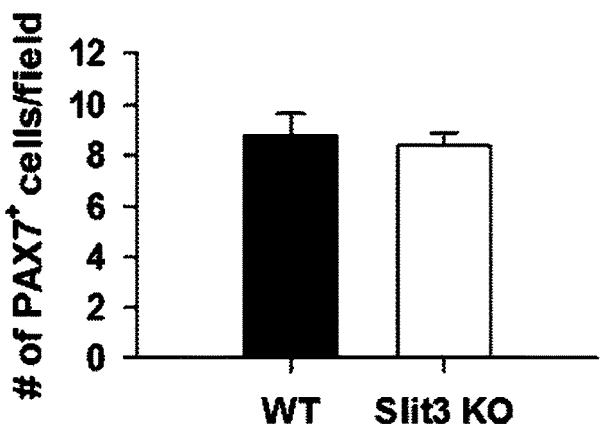
Figure 5D:
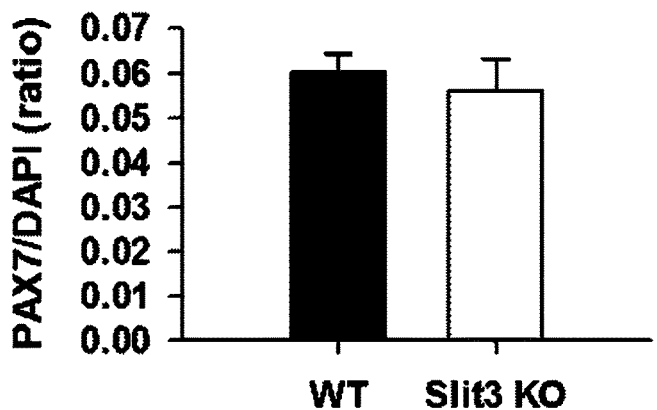

As described above, as the average life expectancy is globally increasing, the aging population is increasing, and accordingly, it is expected that the demand for treatment of sarcopenia will also be continuously increased, but no medicine at a level approved by the FDA as a therapeutic agent against sarcopenia has been reported yet.

In a specific embodiment of the present invention, it was confirmed that the Slit protein or the active fragment thereof can bind to a Robo1 or Robo2 receptor to release the β-catenin binding to the M-cadherin of myoblasts via the Slit-Robo system, and thus could promote the formation of muscles by activating the bound β-catenin and increasing the expression of myogenin to induce the differentiation of myoblasts, thereby directly exhibiting effects of treatment against sarcopenia.

Accordingly, the present invention provides a pharmaceutical composition for preventing and alleviating a muscle disease, including one protein selected from the group consisting of Slit1, Slit2, and Slit3 proteins, a Robo1 protein, a Robo2 protein, and a LRRD2 protein, or a gene encoding the same; or an activator thereof, as an effective ingredient.

It is preferred that the "Slit3 protein" of the present invention consists of an amino acid of SEQ ID No. 1, the "Robo1 protein" of the present invention consists of an amino acid of SEQ ID No. 2, the "Robo2 protein" of the present invention consists of an amino acid of SEQ ID No. 3, and the "LRRD2 protein" of the present invention consists of an amino acid of SEQ ID No. 4, and it is possible to include a functional equivalent of the protein or peptide.

The "functional equivalent" has a sequence homology of at least 70% or more, preferably 80% or more, more preferably 90% or more, and even more preferably 95% or more with the amino acid sequences of SEQ ID Nos. 1 to 4 by the addition, substitution, or deletion of amino acids of a protein or peptide, and refers to a protein or peptide exhibiting physiological activity substantially equivalent to that of a protein or peptide consisting of amino acid sequences of SEQ ID Nos. 1 to 4.

The "activator" of the present invention includes various compounds, proteins or peptides, base sequences, and the like capable of enhancing the expression of Slit1, Slit2, Slit3, Robo1, Robo2, and/or fragments thereof or activating an SLIT-ROBO system. Various metabolites, precursors, and pharmaceutical equivalents of the compound, the protein or peptide, and the base sequence are also included in the activator.

In the present invention, the "Slit3 protein" is preferably expressed from a slit3 gene consisting of a base sequence of SEQ ID No. 5, the "Robo1 protein" is preferably expressed from a robo1 gene consisting of a base sequence of SEQ ID No. 6, the "Robo2 protein" is preferably expressed from a robo2 gene consisting of a base sequence of SEQ ID No. 7, and the "LRRD2 protein" is preferably expressed from a gene consisting of a base sequence of SEQ ID No. 8, but are not limited thereto.

It is preferred that the muscle disease of the present invention is a muscle disease caused by muscular function deterioration, muscle wasting, or muscle degeneration and is a disease reported in the art, and specifically, it is more preferred that the muscle disease of the present invention is one or more selected from the group consisting of atony, muscular atrophy, muscular dystrophy, muscle degeneration, myasthenia, cachexia, and sarcopenia, but the muscle disease is not limited thereto.

The muscle wasting or degeneration occurs due to reasons such as congenital factors, acquired factors, and aging, and the muscle wasting is characterized by a gradual loss of muscle mass, and weakening and degeneration of a muscle, particularly, a skeletal muscle or a voluntary muscle and a cardiac muscle.

More specifically, the muscle comprehensively refers to a sinew, a muscle, and a tendon, and the muscular function or muscle function means an ability to exert a force by contraction of the muscle, and includes: muscular strength in which the muscle can exert the maximum contraction force in order to overcome resistance; muscular endurance strength which is an ability to exhibit how long or how many times the muscle can repeat the contraction and relaxation at a given weight; and explosiveness which is an ability to exert a strong force within a short period of time. The muscular function is proportional to muscle mass, and the term "improvement of muscular function" refers to the improvement of the muscular function in a more positive direction.

In preferred embodiments of the present invention, as a result of confirming the relationship between the expression of Slit3 and muscle mass, the present inventors confirmed that in Slit3-deficient mice, the skeletal muscle was decreased (FIG. 1, FIG. 2, and Tables 1 and 2), and the area of the muscle fiber was remarkably decreased, but the numbers of myoblasts and satellite cells thereof were not changed (FIGS. 3 to 5).

Figure 9A:
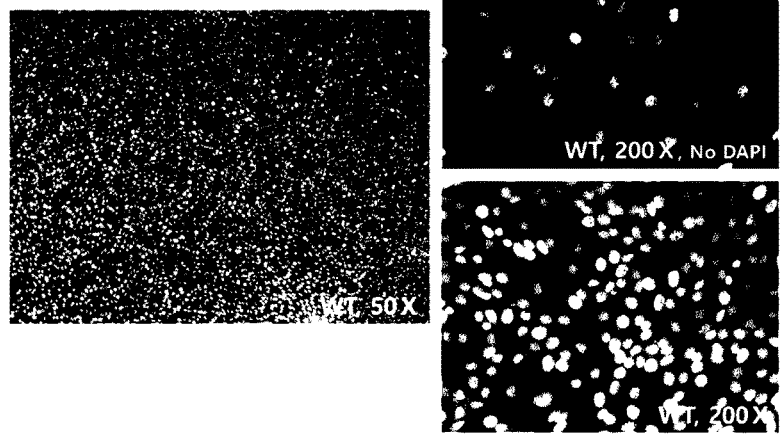
FIGS. 9A and 9B illustrate changes in protein expression levels of myogenin according to Slit3 treatment in the differentiation process of myoblasts.
Figure 9B:
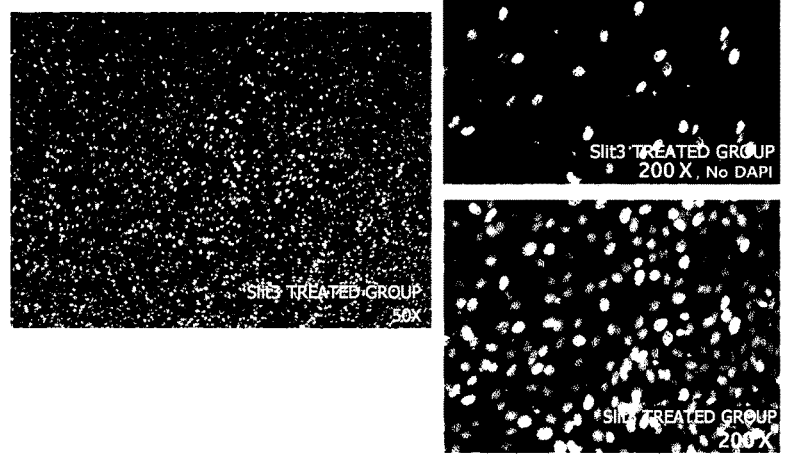
Figure 10:
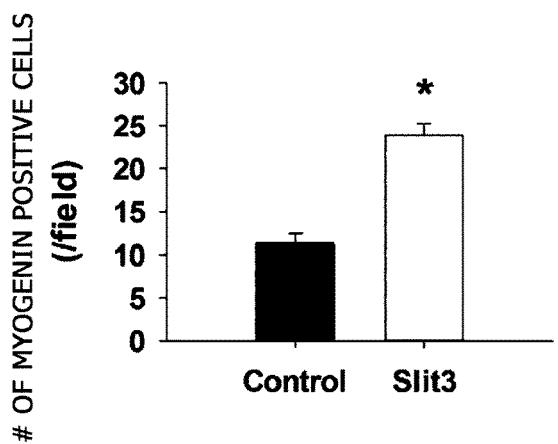
FIG. 10 illustrates the difference in number of myogenin positive cells according to Slit3 treatment in the differentiation process of myoblasts.

Further, as a result of confirming the myoblast differentiation-promoting effect of Slit3, the present inventors confirmed that Slit3 did not affect the viability of myoblasts and enabled myoblasts to be differentiated into myotubes (FIGS. 6 and 7), and confirmed that the expression of myogenin was increased by Slit3 among myogenic regulatory factors participating in the differentiation (FIGS. 8 to 10).

In addition, the present inventors confirmed that in the process in which myoblasts were differentiated into myotubes, the expression of M-cadherin expressed in myoblasts was more abundant than that of N-cadherin, and β-catenin binding to M-cadherin was released, and as a result, the activity of β-catenin was increased by Slit3 (FIGS. 11A, 11B, and 12B), and confirmed that in the differentiation process of myoblasts, the activity of Mβ-catenin could be increased via Slit3, and the expression of myogenin could be increased, thereby participating in the promotion of the formation of muscles by inducing the differentiation of myoblasts (FIGS. 12B, 12C to 12E, and 12F).

Figure 13A:
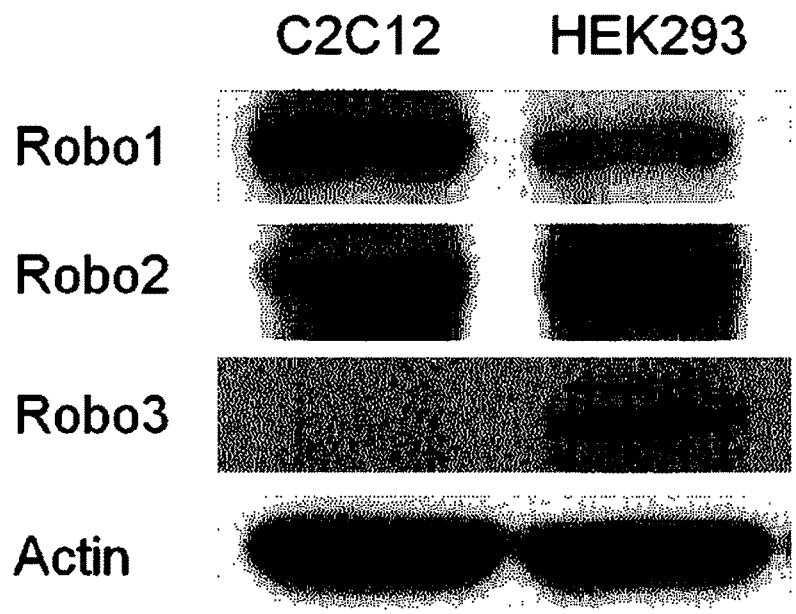
FIG. 13A illustrates subtypes of Robo receptors expressed in C2C12 cells which are myoblasts.
Figure 13A:
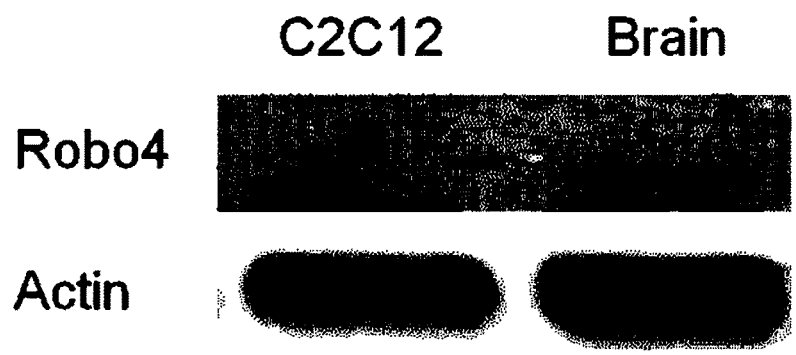
Figure 13B:
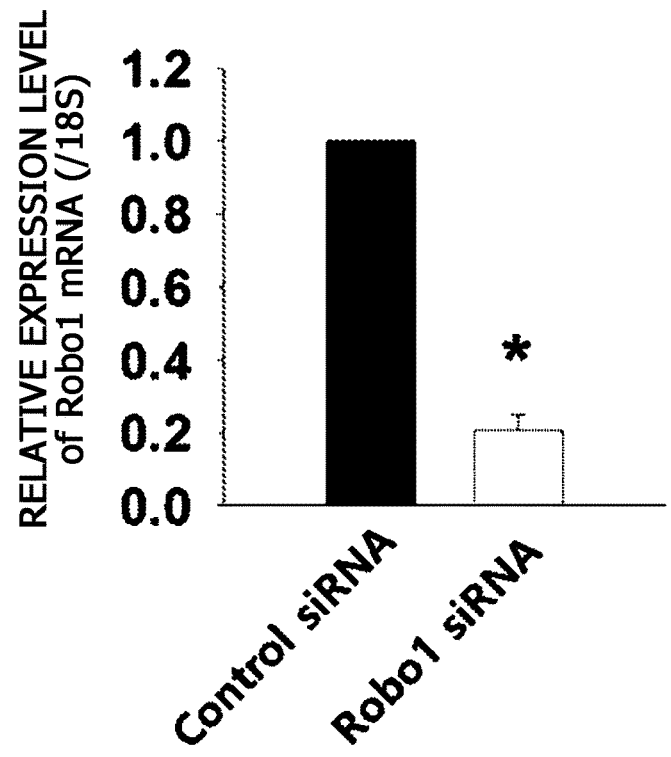
FIGS. 13B to 13D illustrate that a myogenin expression-increasing effect of Slit3 is not significantly increased according to Robo1 or Robo2 knockout in C2C12 cells.
Figure 13C:
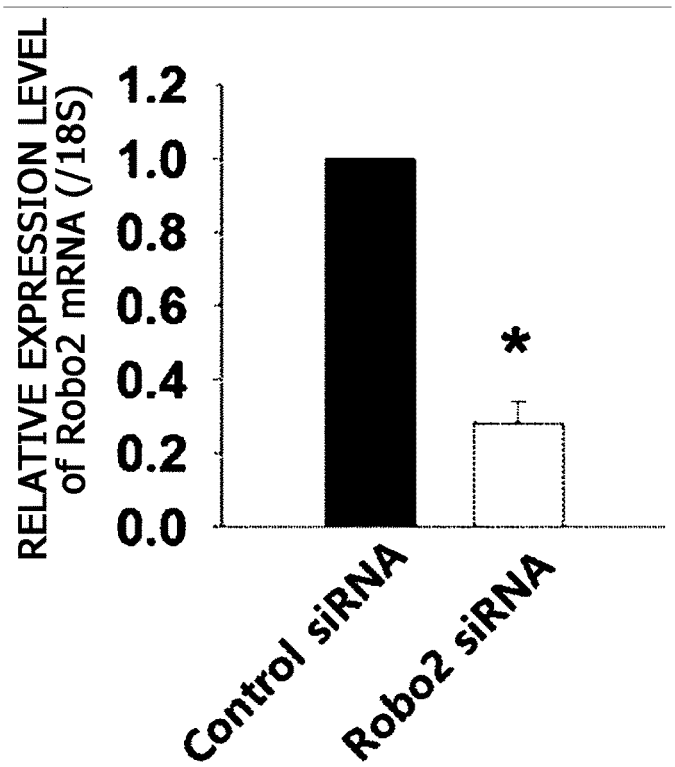

Further, as a result of confirming the Robo receptor subtype binding to Slit3 in myoblasts, the present inventors confirmed that Robo1 and Robo2 receptors were expressed on the surface of the myoblast, and as a result, the Robo1 and Robo2 receptors form a Slit-Robo system to exhibit the effects of Slit3 (FIGS. 13A, 13B, and 13C). In particular, since the case where Robo1 is deficient shows that muscle mass is decreased at the in vivo level, the present inventors confirmed that the effects of alleviating sarcopenia could be exhibited via a binding system of Slit3 and Robo1 or Robo2 (Table 3 and FIG. 14).

In addition, as a result of confirming the effects of Slit3 on myoblast differentiation and an increase in muscle mass by a LRRD2 domain, the present inventors confirmed that the effects of Slit3 on the differentiation of myoblasts by LRRD2 were increased at the in vitro level, and the body weight and sarcopenic indices of Slit3 were increased at the in vivo level in the sarcopenic model mice to which LRRD2 was administered (FIGS. 15 and 16 and Table 4).

Accordingly, the Slit protein of the present invention binds to a Robo1 or Robo2 receptor, and as a result, the β-catenin binding to the M-cadherin of myoblasts was released via the Slit-Robo system to activate the β-catenin and increase the expression of myogenin, and subsequently, the formation of muscles can be promoted by inducing the differentiation of myoblasts. Furthermore, not only in the case of treatment of a full-length Slit protein, but also when an active fragment thereof is treated, an increase in muscle mass can be induced by promoting the differentiation of myoblasts, so that particularly preferably, the Slit protein or the LRRD2 protein of Slit3 of the present invention, or a gene encoding the same can be used as an effective ingredient of a pharmaceutical composition for preventing and treating sarcopenia.

For the protein or peptide of the present invention, not only a protein or peptide having a wild-type amino acid sequence thereof, but also an amino acid sequence variant thereof may also be included in the scope of the present invention. The amino acid sequence variant refers to a protein or peptide in which a wild-type amino acid sequence of Slit1, Slit2, Slit3, Robo1, Robo2, or LRRD2 has a different sequence by deletion, insertion, non-conservative or conservative substitution of one or more amino acid residues, or a combination thereof.

Amino acid exchanges possible in proteins and peptides that do not wholly change the activities of the molecules are known in the art (H. Neurath, R. L. Hill, The Proteins, Academic Press, New York, 1979). The most typically occurring exchanges are exchanges between amino acid residues Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly. In some cases, amino acids may also be modified by phosphorylation, sulfation, acetylation, glycosylation, methylation, farnesylation, or the like.

The Slit1, Slit2, Slit3, Robo1, Robo2 proteins and the LRRD2 protein of the present invention, or variants thereof can be extracted from nature or synthesized (Merrifield, J. Amer. Chem. Soc. 85:2149-2156, 1963) or prepared by a gene recombinant method based on a DNA sequence (Sambrook et al., Molecular Cloning, Cold Spring Harbour Laboratory Press, New York, USA, 2d Ed., 1989).

The Slit1, Slit2, Slit3, Robo1, Robo2 proteins and the LRRD2 protein may be provided in the form of a protein or in the form of an expression vector capable of expressing a gene encoding Slit3, Robo1, Robo2 proteins, and the LRRD2 protein in the cells in order to be used for gene therapy or a vaccine, and the like.

As the expression vector, it is possible to use an expression vector capable of inserting a gene encoding the Slit1, Slit2, Slit3, Robo1, Robo2 proteins or the LRRD2 protein and expressing the protein, and for example, it is possible to use an expression vector such as pBK-CMV (Stratagene) or pCR3.1 (Invitrogen).

Further, a polynucleotide can be administered in a form in which a base sequence encoding the Slit1, Slit2, Slit3, Robo1, Robo2 proteins and the LRRD2 protein of the present invention, that is, a recombinant DNA molecule including the polynucleotide is operably linked to a nucleic acid sequence regulating expression, for example, in the form of an expression vector, such that the base sequence is expressed in a patient to be treated. It is preferred that the vector accordingly includes a suitable transcription regulatory signal including a promoter site capable of expressing a coding sequence, and the promoter being operable in a patient to be treated. Accordingly, for human gene therapy, the term "promoter" including not only a sequence required to deliver a RNA polymerase to a transcription initiation site, but also other operative sequences or regulatory sequences including an enhancer, if appropriate may be preferably a human promoter sequence from a human gene or generally a human promoter sequence from a gene expressed in a human, for example, a promoter from a human cytomegalovirus (CMV). From this viewpoint, among suitable known eukaryotic promoters, the CMVs, that is, a retrovirus LTR promoter such as an early promoter, a HSV thymidine kinase promoter, an early and late SV40 promoter, and promoters of a Rous sarcoma virus ("RSV"), and a metallothionein promoter such as a mouse metallothionein-1 promoter are suitable.

The polynucleotide sequence and the transcription regulatory sequence may be provided and cloned into a replicable plasmid vector, based on commercially available plasmids such as pBR322, or may also be constructed from available plasmids by the routine application of well-known published procedures.

The vector may also include a transcriptional regulatory sequence, located at 3' of the gene sequence, and a polyadenylation sequence, recognizable in a patient to be treated, such as the corresponding sequence from a virus such as the SV40 virus, when used for human therapy. Other transcription regulatory sequences are well known in the art, and thus can be used.

The expression vector may also include a selectable marker, such as antibiotic resistance, which enables the vector to be propagated.

Expression vectors capable of in situ synthesizing the protein or peptide may be introduced into a wound site directly by physical methods. Examples of these methods include topical application of a "naked" nucleic acid vector in a suitable vehicle, for example, in a solution in a pharmaceutically acceptable excipient such as phosphate buffered saline (PBS), or administration of a vector by physical methods such as particle bombardment, also known as "gene gun" technology, according to methods known in the art. As described in U.S. Pat. No. 5,371,015, the "gene gun" technology is a method in which inert particles, such as gold beads coated with a vector are accelerated at a speed sufficient to enable the particles to penetrate a wound site, for example, the surface of skin cells, by means of discharge under high pressure from a propelling device. In addition, other physical methods of administering DNA directly to a receptor include ultrasound, electrical stimulation, electroporation, microseeding, and the like.

The gene sequence may also be administered to the wound site by means of transformed host cells. Such cells include cells harvested from a patient, and the nucleic acid sequence may be introduced into the cells by gene transfer methods known in the art, followed by growth of the transformed cells in a culture solution and transplantation into the patient.

The expression construct as described above may be used in the treatment of the present invention by various methods. Accordingly, the expression constructs may be directly administered to a site of a patient to be treated.

Furthermore, the pharmaceutical composition of the present invention may include an activation factor for increasing the expression of the Slit1, Slit2, Slit3, Robo1, Robo2 protein or the LRRD2 protein as an effective ingredient.

The activation factor for increasing the expression of the Slit1, Slit2, Slit3, Robo1, Robo2 protein or the LRRD2 protein refers to a material that directly or indirectly acts on the slit1, slit2, slit3, robo1, robo2 gene or a gene encoding LRRD2 to improve, induce, stimulate, and increase the biological activity of the Slit1, Slit2, Slit3, Robo1, Robo2 protein or the LRRD2 protein. The material includes a single compound such as an organic or inorganic compound, a biopolymer compound such as a peptide, a protein, a nucleic acid, a carbohydrate, and a lipid, a complex of multiple compounds, and the like. The activation factor for increasing the expression of slit1, slit2, or slit3 may be used in prevention, alleviation, and treatment of a disease occurring due to a decrease in expression, activity, or function of slit1, slit2, or slit3.

A mechanism whereby the material activates the slit1, slit2, slit3, robo1, robo2 gene or a gene encoding LRRD2 is not particularly limited. For example, the material may increase the expression of a gene, such as transcription and translation, or may function as a mechanism that converts a non-active type into an active type. Preferably, the material activating the slit1, slit2, slit3, robo1, robo2 gene or a gene encoding LRRD2 is a biopolymer compound such as a peptide, a protein, a nucleic acid, a carbohydrate, and a lipid.

With respect to the slit1, slit2, and slit3, nucleic acid and protein sequences of which are already known, a single compound peptide such as an organic or inorganic compound which acts as an inducer or an activator, a biopolymer compound such as a peptide, a protein, a nucleic acid, a carbohydrate, and a lipid, a complex of multiple compounds, and the like may be prepared or screened by using technologies known in the art.

The composition of the present invention may be in the form of various oral or parenteral formulations. When the composition is formulated, the composition may be prepared by using a buffer (for example, a saline solution or PBS), an antioxidant, a bacteriostatic agent, a chelating agent (for example, EDTA or glutathione), a filler, an extender, a binder, an adjuvant (for example, aluminum hydroxide), a suspension agent, a thickener, a wetting agent, a disintegrant, or a surfactant, a diluent or an excipient.

Examples of a solid preparation for oral administration include a tablet, a pill, a powder, a granule, a capsule, and the like, and the solid preparation is prepared by mixing one or more compounds with one or more excipients, for example, starch (including corn starch, wheat starch, rice starch, potato starch, and the like), calcium carbonate, sucrose, lactose, dextrose, sorbitol, mannitol, xylitol, erythritol, maltitol, cellulose, methyl cellulose, sodium carboxymethylcellulose and hydroxypropymethyl-cellulose, gelatin, or the like. For example, a tablet or a sugar tablet may be obtained by blending an active ingredient with a solid excipient, pulverizing the resulting blend, adding a suitable auxiliary agent thereto, and then processing the resulting mixture into a granular mixture.

Further, in addition to a simple excipient, lubricants such as magnesium stearate and talc are also used. A liquid preparation for oral administration corresponds to a suspension agent, a liquid for internal use, an emulsion, a syrup, and the like, and the liquid preparation may include, in addition to water and liquid paraffin which are simple commonly used diluents, various excipients, for example, a wetting agent, a sweetener, an odorant, a preservative, and the like. In addition, in some cases, cross-linked polyvinyl pyrrolidone, agar, alginic acid, sodium alginate, or the like as a disintegrant may be added, and an anti-coagulant, a lubricant, a wetting agent, a fragrance, an emulsifier, an antiseptic, and the like may be additionally added.

Examples of a preparation for parenteral administration include an aqueous sterile solution, a non-aqueous solvent, a suspension solvent, an emulsion, a freeze-dried preparation, a suppository, or the like. As the non-aqueous solvent and the suspension solvent, it is possible to use propylene glycol, polyethylene glycol, a vegetable oil such as olive oil, an injectable ester such as ethyl oleate, and the like. As a base of the suppository, it is possible to use Witepsol, Macrogol, Tween 61, cacao butter, laurin fat, glycerol, gelatin, and the like.

The composition of the present invention may be administered orally or parenterally, and, when administered parenterally, may be formulated in the form of a preparation for external application to the skin; an injection administered intraperitoneally, rectally, intravenously, muscularly, subcutaneously, or intracerebroventricularly, or via cervical intrathecal injection; a percutaneous administration agent; or a nasal inhaler according to a method known in the art.

The injection must be sterilized and protected from contamination of microorganisms such as bacteria and fungi. Examples of a suitable carrier for the injection may be, but are not limited to, a solvent or a dispersion medium including water, ethanol, polyols (for example, glycerol, propylene glycol, liquid polyethylene glycol, and the like), mixtures thereof, and/or vegetable oils. More preferably, as a suitable carrier, it is possible to use an isotonic solution such as Hank's solution, Ringer's solution, triethanolamine-containing phosphate buffered saline (PBS) or sterile water for injection, 10% ethanol, 40% propylene glycol, and 5% dextrose, and the like. To protect the injection from microorganism contamination, various antimicrobial agents and antifungal agents such as paraben, chlorobutanol, phenol, sorbic acid, and thimerosal may be additionally included. Furthermore, in most cases, the injection may additionally include an isotonic agent such as sugar or sodium chloride.

Examples of the percutaneous administration agent include a form such as an ointment, a cream, a lotion, a gel, a solution for external use, a paste, a liniment, and an aerosol. The percutaneous administration as described above means that an effective amount of an active ingredient contained in a pharmaceutical composition is delivered into the skin via local administration thereof to the skin.

In the case of a preparation for inhalation, the compound used according to the present invention may be conveniently delivered in the form of an aerosol spray from a pressurized pack or a nebulizer by using a suitable propellant, for example, dichlorofluoromethane, trichlorofluoromethane, dichlorotetrafluoroethane, carbon dioxide, or other suitable gases. In the case of the pressurized aerosol, a dosage unit may be determined by providing a valve for transferring a weighed amount. For example, a gelatin capsule and a cartridge for use in an inhaler or insufflator may be formulated so as to contain a powder mixture of a compound and a suitable powder base such as lactose or starch. Formulations for parenteral administration are described in the document, which is a guidebook generally known in all pharmaceutical chemistry fields (Remington's Pharmaceutical Science, 15th Edition, 1975. Mack Publishing Company, Easton, Pa. 18042, Chapter 87: Blaug, Seymour).

The composition of the present invention is administered in a pharmaceutically effective amount. The term "pharmaceutically effective amount" as used herein refers to an amount sufficient to treat diseases at a reasonable benefit/risk ratio applicable to medical treatment, and an effective dosage level may be determined according to factors including type of diseases of patients, the severity of disease, the activity of drugs, sensitivity to drugs, administration time, administration routes, excretion rate, treatment periods, and simultaneously used drugs, and factors well known in other medical fields. The composition according to the present invention may be administered as an individual therapeutic agent or in combination with other therapeutic agents, may be administered sequentially or simultaneously with therapeutic agents in the related art, and may be administered in a single dose or multiple doses. That is, the total effective amount of the composition of the present invention may be administered to a patient in a single dose or may be administered by a fractionated treatment protocol, in which multiple doses are administered over a long period of time. It is important to administer the composition in a minimum amount that can obtain the maximum effect without any side effects, in consideration of all the aforementioned factors, and this may be easily determined by the person skilled in the art.

A dosage of the pharmaceutical composition of the present invention varies according to body weight, age, gender, and health status of a patient, diet, administration time, administration method, excretion rate, and the severity of a disease. A daily dosage thereof may be administered parenterally in an amount of preferably 0.01 mg to 50 mg, and more preferably 0.1 mg to 30 mg per kg of body weight a day based on the Slit1, Slit2, Slit3, Robo1, Robo2 protein or the LRRD2 protein, and a daily dosage thereof may be administered orally in a single dose or multiple doses in an amount of preferably 0.01 mg to 100 mg, and more preferably 0.01 mg to 10 mg per kg of body weight a day based on the Slit1, Slit2, Slit3, Robo1, Robo2 protein or the LRRD2 protein. However, since the dosage may be increased or decreased depending on the administration route, the severity of obesity, the gender, the body weight, the age, and the like, the dosage is not intended to limit the scope of the present invention in any way.

The composition of the present invention may be used either alone or in combination with surgery, radiation therapy, hormone therapy, chemotherapy, and methods using a biological response modifier.

The pharmaceutical composition of the present invention may also be provided in the form of a formulation for external use, including the Slit1, Slit2, Slit3, Robo1, Robo2 protein or the LRRD2 protein, or a base sequence encoding the same as an effective ingredient. When the pharmaceutical composition for preventing and treating a muscle disease according to the present invention is used as a preparation for external application to the skin, the pharmaceutical composition may additionally contain auxiliary agents typically used in the dermatology field, such as any other ingredients typically used in the preparation for external application to the skin, such as a fatty substance, an organic solvent, a solubilizing agent, a thickener and a gelling agent, a softener, an antioxidant, a suspending agent, a stabilizer, a foaming agent, an odorant, a surfactant, water, an ionic emulsifier, a non-ionic emulsifier, a filler, a metal ion blocking agent, a chelating agent, a preservative, a vitamin, a blocking agent, a wetting agent, an essential oil, a dye, a pigment, a hydrophilic active agent, a lipophilic active agent, or a lipid vesicle. In addition, the ingredients may be introduced in an amount generally used in the dermatology field.

When the pharmaceutical composition for preventing and treating a muscle disease according to the present invention is provided as a preparation for external application to the skin, the pharmaceutical composition may be in the form of a formulation such as an ointment, a patch, a gel, a cream, and an aerosol, but is not limited thereto.

Furthermore, the present invention provides a health functional food for preventing and alleviating a muscle disease, including one protein selected from the group consisting of a Slit1 protein, a Slit2 protein, a Slit3 protein, a Robo1 protein, a Robo2 protein, and a LRRD2 protein, or a gene encoding the same, as an effective ingredient.

It is preferred that the "Slit3 protein" of the present invention consists of an amino acid of SEQ ID No. 1, the "Robo1 protein" of the present invention consists of an amino acid of SEQ ID No. 2, the "Robo2 protein" of the present invention consists of an amino acid of SEQ ID No. 3, and the "LRRD2 protein" of the present invention consists of an amino acid of SEQ ID No. 4, and it is possible to include a functional equivalent of the protein or peptide.

The "functional equivalent" has a sequence homology of at least 70% or more, preferably 80% or more, more preferably 90% or more, and even more preferably 95% or more with the amino acid sequences of SEQ ID Nos. 1 to 4 by the addition, substitution, or deletion of amino acids of a protein or peptide, and refers to a protein or peptide exhibiting physiological activity substantially equivalent to that of a protein or peptide consisting of amino acid sequences of SEQ ID Nos. 1 to 4.

In the present invention, the "Slit3 protein" is preferably expressed from a slit3 gene consisting of a base sequence of SEQ ID No. 5, the "Robo1 protein" is preferably expressed from a robo1 gene consisting of a base sequence of SEQ ID No. 6, the "Robo2 protein" is preferably expressed from a robo2 gene consisting of a base sequence of SEQ ID No. 7, and the "LRRD2 protein" is preferably expressed from a gene consisting of a base sequence of SEQ ID No. 8, but are not limited thereto.

It is preferred that the muscle disease of the present invention is a muscle disease caused by muscular function deterioration, muscle wasting, or muscle degeneration and is a disease reported in the art, and specifically, it is more preferred that the muscle disease of the present invention is one or more selected from the group consisting of atony, muscular atrophy, muscular dystrophy, muscle degeneration, myasthenia, cachexia, and sarcopenia, but the muscle disease is not limited thereto.

The muscle wasting or degeneration occurs for reasons such as congenital factors, acquired factors, and aging, and the muscle wasting is characterized by a gradual loss of muscle mass, and weakening and degeneration of a muscle, particularly, a skeletal muscle or a voluntary muscle and a cardiac muscle.

More specifically, the muscle comprehensively refers to a sinew, a muscle, and a tendon, and the muscular function or muscle function means an ability to exert a force by contraction of the muscle, and includes: muscular strength in which the muscle can exert the maximum contraction force in order to overcome resistance; muscular endurance strength which is an ability to exhibit how long or how many times the muscle can repeat the contraction and relaxation at a given weight; and explosiveness which is an ability to exert a strong force within a short period of time. The muscular function is proportional to muscle mass, and the term "improvement of muscular function" refers to the improvement of the muscular function in a more positive direction.

The Slit protein of the present invention binds to a Robo1 or Robo2 receptor, and as a result, the β-catenin binding to the M-cadherin of myoblasts was released via the Slit-Robo system to activate the β-catenin and increase the expression of myogenin, and subsequently, the formation of muscles can be promoted by inducing the differentiation of myoblasts. Further, not only in the case of treatment of a full-length Slit protein, but also when an active fragment thereof, particularly preferably, a LRRD2 protein is treated, an increase in muscle mass can be induced by promoting the differentiation of myoblasts, so that the Slit protein of the present invention or an active fragment of Slit, or a gene encoding the same can be used as an effective ingredient of a health functional food for preventing and alleviating sarcopenia. Further, the Slit protein of the present invention or an active fragment of Slit, or a gene encoding the same can be used as an effective ingredient of a feed composition for preventing and alleviating sarcopenia.

The food composition according to the present invention can be prepared in various forms by typical methods known in the art. A general food can be prepared by adding the Slit1, Slit2, Slit3, Robo1, Robo2 protein or the LRRD2 protein of the present invention to, without being limited to, a beverage (including an alcoholic beverage), fruit and a processed food thereof (for example: canned fruit, bottled food, jam, marmalade, and the like), fish, meat and processed food thereof (for example: ham, sausage, corned beef, and the like), bread and noodles (for example: thick wheat noodles, buckwheat noodles, instant noodles, spaghetti, macaroni, and the like), fruit juices, various drinks, cookies, wheat-gluten, dairy products (for example: butter, cheese, and the like), edible vegetable oils, margarine, vegetable protein, retort foods, frozen food and various seasonings (for example: soybean paste, soy sauce, sauce, and the like), and the like. In addition, a nutrition supplement can be prepared by adding the Slit1, Slit2, Slit3, Robo1, Robo2 protein or the LRRD2 protein of the present invention to, without being limited to, a capsule, a tablet, a pill, and the like. Furthermore, for a health functional food, for example, the Slit1, Slit2, Slit3, Robo1, Robo2 protein or the LRRD2 protein of the present invention itself is prepared in the form of, without being limited to, tea, juice, and drink and can be taken by being processed into a liquid, a granule, a capsule, and a powder so as to be able to be drunk (health beverage). Further, the Slit1, Slit2, Slit3, Robo1, Robo2 protein or the LRRD2 protein of the present invention can be used and prepared in the form of a powder or a concentrated liquid so as to be used in the form of a food additive. In addition, the food composition of the present invention can be prepared in the form of a composition by mixing the Slit1, Slit2, Slit3, Robo1, Robo2 protein or the LRRD2 protein of the present invention with a known active ingredient known to have effects of preventing a muscle disease and improving muscular function.

When the Slit1, Slit2, Slit3, Robo1, Robo2 protein or the LRRD2 protein of the present invention is used as a health beverage, the health beverage composition can contain various flavoring agents or natural carbohydrates, and the like as additional ingredients, such as a typical beverage. The above-described natural carbohydrates may be monosaccharides such as glucose and fructose; disaccharides such as maltose and sucrose; polysaccharides such as dextrin and cyclodextrin; and sugar alcohols such as xylitol, sorbitol, and erythritol. As a sweetener, it is possible to use a natural sweetener such as thaumatin and a stevia extract; a synthetic sweetener such as saccharin and aspartame, and the like. The proportion of the natural carbohydrate is generally about 0.01 to 0.04 g, and preferably about 0.02 to 0.03 g per 100 mL of the composition of the present invention.

Furthermore, the Slit1, Slit2, Slit3, Robo1, Robo2 protein or the LRRD2 protein of the present invention may be contained as an effective ingredient of a food composition for preventing a muscle disease and improving muscular function, and the amount thereof is an amount effective to achieve an action for preventing a muscle disease and improving muscular function and is not particularly limited, but is preferably 0.01 to 100 wt % based on the total weight of the entire composition. Further, the food composition according of the present invention can be prepared by mixing the Slit1, Slit2, Slit3, Robo1, Robo2 protein or the LRRD2 protein with other active ingredients known to have effects of preventing a muscle disease and improving muscular function.

In addition to the aforementioned ingredients, the health food of the present invention may contain various nutrients, vitamins, electrolytes, flavoring agents, coloring agents, pectic acid, salts of pectic acid, alginic acid, salts of alginic acid, organic acids, protective colloidal thickeners, pH adjusting agents, stabilizers, preservatives, glycerin, alcohols, carbonating agents, and the like. Besides, the health food of the present invention may contain the flesh for preparing natural fruit juice, fruit juice beverage, or vegetable beverage. These ingredients may be used either alone or in mixtures thereof. The proportion of these additives is not significantly important, but is generally selected within a range of 0.01 to 0.1 part by weight per 100 parts by weight of the composition of the present invention.

In addition, the present invention provides a cosmetic composition for improving muscular function, including one protein selected from the group consisting of a Slit1 protein, a Slit2 protein, a Slit3 protein, a Robo1 protein, a Robo2 protein, and a LRRD2 protein, or a gene encoding the same, as an effective ingredient. The cosmetic composition is not particularly limited, but may be used for external application to the skin, or orally ingested.

It is preferred that the "Slit3 protein" of the present invention consists of an amino acid of SEQ ID No. 1, the "Robo1 protein" of the present invention consists of an amino acid of SEQ ID No. 2, the "Robo2 protein" of the present invention consists of an amino acid of SEQ ID No. 3, and the "LRRD2 protein" of the present invention consists of an amino acid of SEQ ID No. 4, and it is possible to include a functional equivalent of the protein or peptide.

The "functional equivalent" has a sequence homology of at least 70% or more, preferably 80% or more, more preferably 90% or more, and even more preferably 95% or more with the amino acid sequences of SEQ ID Nos. 1 to 4 by the addition, substitution, or deletion of amino acids of a protein or peptide, and refers to a protein or peptide exhibiting physiological activity substantially equivalent to that of a protein or peptide consisting of amino acid sequences of SEQ ID Nos. 1 to 4.

In the present invention, the "Slit3 protein" is preferably expressed from a slit3 gene consisting of a base sequence of SEQ ID No. 5, the "Robo1 protein" is preferably expressed from a robo1 gene consisting of a base sequence of SEQ ID No. 6, the "Robo2 protein" is preferably expressed from a robo2 gene consisting of a base sequence of SEQ ID No. 7, and the "LRRD2 protein" is preferably expressed from a gene consisting of a base sequence of SEQ ID No. 8, but are not limited thereto.

It is preferred that the muscle disease of the present invention is a muscle disease caused by muscular function deterioration, muscle wasting, or muscle degeneration and is a disease reported in the art, and specifically, it is more preferred that the muscle disease of the present invention is one or more selected from the group consisting of atony, muscular atrophy, muscular dystrophy, muscle degeneration, myasthenia, cachexia, and sarcopenia, but the muscle disease is not limited thereto.

The muscle wasting or degeneration occurs for reasons such as congenital factors, acquired factors, and aging, and the muscle wasting is characterized by a gradual loss of muscle mass, and weakening and degeneration of a muscle, particularly, a skeletal muscle or a voluntary muscle and a cardiac muscle.

More specifically, the muscle comprehensively refers to a sinew, a muscle, and a tendon, and the muscular function or muscle function means an ability to exert a force by contraction of the muscle, and includes: muscular strength in which the muscle can exert the maximum contraction force in order to overcome resistance; muscular endurance strength which is an ability to exhibit how long or how many times the muscle can repeat the contraction and relaxation at a given weight; and explosiveness which is an ability to exert a strong force within a short period of time. The muscular function is proportional to muscle mass, and the term "improvement of muscular function" refers to the improvement of the muscular function in a more positive direction.

The Slit protein of the present invention binds to a Robo1 or Robo2 receptor, and as a result, the β-catenin binding to the M-cadherin of myoblasts was released via the Slit-Robo system to activate the β-catenin and increase the expression of myogenin, and subsequently, the formation of muscles can be promoted by inducing the differentiation of myoblasts. Furthermore, not only in the treatment of a full-length Slit protein, but also when an active fragment thereof, particularly preferably, a LRRD2 protein is treated, an increase in muscle mass can be induced by promoting the differentiation of myoblasts, so that the Slit protein of the present invention or an active fragment of Slit, or a gene encoding the same can be used as an effective ingredient of a cosmetic composition for improving muscular function.

The composition for improving muscular function of the present invention may also be a cosmetic composition. The cosmetic composition of the present invention contains a Slit1 protein, a Slit2 protein, a Slit3 protein, a Robo1 protein, a Robo2 protein or a LRRD2 protein as an effective ingredient, and may be prepared in the form of a basic cosmetic composition (a lotion, a cream, an essence, a cleanser such as cleansing foam and cleansing water, a pack, and a body oil), a coloring cosmetic composition (a foundation, a lipstick, a mascara, and a make-up base), a hair product composition (a shampoo, a rinse, a hair conditioner, and a hair gel), a soap, and the like with dermatologically acceptable excipients.

The excipient may include, for example, but not limited thereto, a skin softener, a skin infiltration enhancer, a coloring agent, an aroma, an emulsifier, a thickener, and a solvent. Further, it is possible to additionally include a fragrance, a pigment, a disinfectant, an antioxidant, a preservative, a moisturizer and the like, and to include a thickening agent, inorganic salts, a synthetic polymer material, and the like for improving physical properties. For example, when a cleanser and a soap are prepared by using the cosmetic composition of the present invention, the cleanser and the soap may be easily prepared by adding the Slit1 protein, Slit2 protein, Slit3 protein, Robo1 protein, Robo2 protein, or LRRD2 protein to a typical cleanser and soap base. When a cream is prepared, the cream may be prepared by adding the Slit1 protein, Slit2 protein, Slit3 protein, Robo1 protein, Robo2 protein, or LRRD2 protein, or a base sequence encoding the same to a general oil-in-water (O/W) cream base. It is possible to further add a fragrance, a chelating agent, a pigment, an antioxidant, a preservative, and the like, and synthetic or natural materials such as proteins, minerals or vitamins for the purpose of improving physical properties.

The content of the Slit1 protein, Slit2 protein, Slit3 protein, Robo1 protein, Robo2 protein or the LRRD2 protein contained in the cosmetic composition of the present invention is, but not limited to, preferably 0.001 to 10 wt %, and more preferably 0.01 to 5 wt %, based on the total weight of the entire composition. When the content is less than 0.001 wt %, desired anti-aging or wrinkle-reducing effects cannot be expected, and when the content exceeds 10 wt %, it may be difficult to prepare the cosmetic composition of the present invention for reasons such as safety or formulation.

In addition, the present application provides a method for detecting a protein for providing information on diagnosis of a muscle disease, the method including the steps:

i) measuring an expression level of a Slit3 protein consisting of an amino acid sequence of SEQ ID No. 1 from a subject-derived sample which is an experimental group;

ii) comparing the expression level of the Slit3 protein measured in Step i) with an expression level of a Slit3 protein of a normal individual-derived sample which is a control group; and iii) determining the experimental group as a muscle disease when the expression level of the Slit3 protein of the experimental group compared in Step ii) is decreased as compared to that of the control group.

In the present invention, the "measuring the expression level of the protein" may be confirmed by measuring the expression level of mRNA or the protein.

Furthermore, the present invention provides a method for screening a therapeutic agent against a muscle disease, the method including the steps of:

i) treating a cell line expressing one or more selected from the group consisting of a Slit3 protein consisting of an amino acid sequence of SEQ ID No. 1, a Robo1 protein consisting of an amino acid sequence of SEQ ID No. 2, and a Robo2 protein consisting of an amino acid sequence of SEQ ID No. 3 with a subject compound or composition;

ii) measuring an expression degree of the Slit3 protein or activity of the Robo1 protein or Robo2 protein in the cell line treated in Step i); and iii) selecting a subject compound or composition in which the expression degree of the Slit3 or the activity of the Robo1 protein or Robo2 protein in Step ii) is increased in comparison with that of the control group cell line which is not treated with the subject compound or composition.

It is preferred that the muscle disease of the present invention is a muscle disease caused by muscular function deterioration, muscle wasting, or muscle degeneration and is a disease reported in the art, and specifically, it is more preferred that the muscle disease of the present invention is one or more selected from the group consisting of atony, muscular atrophy, muscular dystrophy, muscle degeneration, myasthenia, cachexia, and sarcopenia, but the muscle disease is not limited thereto.

The muscle wasting or degeneration occurs for reasons such as congenital factors, acquired factors, and aging, and the muscle wasting is characterized by a gradual loss of muscle mass, and weakening and degeneration of a muscle, particularly, a skeletal muscle or a voluntary muscle and a cardiac muscle.

More specifically, the muscle comprehensively refers to a sinew, a muscle, and a tendon, and the muscular function or muscle function means an ability to exert a force by contraction of the muscle, and includes: muscular strength in which the muscle can exert the maximum contraction force in order to overcome resistance; muscular endurance strength which is an ability to exhibit how long or how many times the muscle can repeat the contraction and relaxation at a given weight; and explosiveness which is an ability to exert a strong force within a short period of time. The muscular function is proportional to muscle mass, and the term "improvement of muscular function" refers to the improvement of the muscular function in a more positive direction.

The Slit protein of the present invention or a LRRD2 protein thereof binds to a Robo1 or Robo2 receptor, and as a result, the β-catenin binding to the M-cadherin of myoblasts was released via the Slit-Robo system to activate the β-catenin and increase the expression of myogenin, and subsequently, the formation of muscles can be promoted by inducing the differentiation of myoblasts. Accordingly, it is possible to determine the onset of sarcopenia before direct symptoms appear through the expression level of the Slit protein or the LRRD2 protein thereof. Further, it is possible to select a compound or composition capable of increasing the expression level of the Slit protein or the activity of the Robo receptor as a candidate material for a therapeutic agent against sarcopenia.

In the method of the present invention, in the measurement of the expression level of mRNA, the amount of mRNA is measured by a process of confirming the presence or absence and expression degree of mRNA encoding the SLIT3 protein or LRRD2 protein in a biological sample. As an analysis method for the same, a method known in the art may be used, and examples thereof include polymerase chain reaction (PCR), reverse transcription-polymerase chain reaction (RT-PCR), competitive RT-PCR, real time RT-PCR, RNase protection assay (RPA), Northern blotting, DNA chips, and the like, but are not limited thereto.

In the method of the present invention, the measurement of the expression level of a protein refers to the measurement of an amount of a protein through a process of confirming the presence or absence and expression degree of the SLIT3 protein or LRRD2 protein in a biological sample. Preferably, the amount of the protein may be confirmed by using an antibody specifically binding to the protein of the gene. As an analysis method for the same, a method known in the art may be used, and examples thereof include enzyme linked immunosorbent assay (ELISA), radioimmunoassay (RIA), an Ouchterlony immunodiffusion method, rocket immunoelectrophoresis, tissue immunostaining, an immunoprecipitation assay, a complement fixation assay, fluorescence activated cell sorter (FACS), a protein chip, and the like, but are not limited thereto.

In the method for detecting a protein for providing information on diagnosis of a muscle disease and the method for screening a therapeutic agent against a muscle disease, the Slit3 in a preferred embodiment is used and described, but Slit1, Slit2; or an active fragment of Slit1, Slit2, and Slit3 may be used.

BEST MODE

Hereinafter, the present invention will be described in more detail through Examples. These Examples are only for exemplifying the present invention, and it will be obvious to a person with ordinary skill in the art that the scope of the present invention is not to be interpreted as being limited by these Examples.

Example 1 Confirmation of Relationship Between Slit3 Expression and Muscle Mass

<1-1> Confirmation of Changes in Body Weight and Sarcopenic Indices in Slit3-Deficient Mouse Model In order to confirm whether Slit3 participated in the formation of skeletal muscles in vivo, a change in muscle mass in a mouse model was confirmed according to the presence or absence of Slit3 expression.

Specifically, embryos of slit3 knockout mice were purchased from Mutant Mouse Regional Resource Centers (Stock number 030759-MU; Columbia, Mo., USA), and a Slit3-deficient mouse model was prepared by breeding the male and female slit3+/−C57BL/6J mice. The Slit3-deficient mouse model was again divided into a male group and a female group to measure the body weight of the mouse model in which the Slit3 expression was deficient. When the mouse model became 7 weeks old, the male group and the female group were sacrificed, and the body weights thereof were measured by obtaining the muscles of each extensor digitorum longus (EDL) and gastrocnemius and soleus (GC+SOL). The sarcopenic index is shown by using the equation "sarcopenic index (%)=100×the weight of the muscle/the body weight" in order to denote muscle mass as a percentage of the body weight of a mouse.

As a result, as shown in FIG. 1, FIG. 2, and the following [Table 1] and [Table 2], it was confirmed that in the Slit3-deficient mouse model, the body weights of the male group and the female group were lower than those of the mice in the normal control group, the weights of the EDL and the weights of the GC+SOL in the male group and the female group were also lower than those in the normal control group, and the sarcopenic indices of the EDL and the sarcopenic indices of the GC+SOL were also significantly decreased as compared to those in the normal control group (FIG. 1, FIG. 2, Table 1, and Table 2). Through this, it was confirmed that when Slit3 was deficient in vivo regardless of gender and type of muscle, skeletal system muscle mass was also decreased.

TABLE 1

Comparison of Changes in Body Weight and Sarcopenic Indices in Slit-Deficient Male Mice

| Experimental group | Body weight (g) | Muscle weight (g) | | Sarcopenic index (%) | |
|---|---|---|---|---|---|
| | | EDL | GC + SOL | EDL | GC + SOL |
| Normal control group | 22.8 ± 0.7 | 0.058 ± 0.002 | 0.131 ± 0.001 | 0.257 ± 0.011 | 0.578 ± 0.015 |
| Slit3-deficient group | 19.8 ± 1.0 | 0.041 ± 0.003 | 0.101 ± 0.008 | 0.207 ± 0.014 | 0.507 ± 0.022 |

TABLE 2

Comparison of Changes in Body Weight and Sarcopenic Indices in Slit-Deficient Female Mice

| Experimental group | Body weight (g) | Muscle weight (g) | | Sarcopenic index (%) | |
|---|---|---|---|---|---|
| | | EDL | GC + SOL | EDL | GC + SOL |
| Normal control group | 18.6 ± 0.5 | 0.047 ± 0.006 | 0.104 ± 0.007 | 0.250 ± 0.026 | 0.558 ± 0.028 |
| Slit3-deficient group | 18.2 ± 0.4 | 0.031 ± 0.003 | 0.083 ± 0.004 | 0.171 ± 0.020 | 0.458 ± 0.028 |

<1-2> Confirmation of Changes in Muscle Area in Slit3-Deficient Mouse Model

Since it was confirmed that the skeletal muscles in the Slit3-deficient mice were decreased, muscle areas were compared by staining the muscles in order to confirm that the muscles were decreased.

Specifically, EDL and GC+SOL muscle tissues were obtained by sacrificing the 7 week-old female mouse model group in which Slit3 was deficient, and then fixed in 4% formaldehyde and embedded in an OCT compound. And then, the muscle tissues were stained through hematoxylin & eosin (H-E) staining by treatment with hematoxylin and eosin. By the stained muscle tissues and using the ImageJ software, the numbers of nuclei and fibrous portions of the muscle tissues were compared and the areas were confirmed.

Further, in order to more specifically compare the numbers of the cells, marker proteins for the sarcolemma, the nucleus, and the satellite cells that are stem cells of myoblasts were immunohistochemically stained. After a reaction was carried out according to the manufacturer's protocol by treating the cross-section of the GC muscle tissue with each of an anti-laminin antibody and an anti-PAX7 antibody as primary antibodies, the marker proteins for the sarcolemma and the satellite cells that are stem cells of myoblasts were stained by developing color with a secondary antibody, the nucleus was stained by treatment with 4'6-diamidino-2-phenylindole (DAPI), and then the proportion of the stem cells of myoblasts in cells in the GC muscle tissues was obtained by observing the GC muscle tissues with a fluorescence microscope.

As a result, as illustrated in FIGS. 3 to 5, it was confirmed that in the Slit3-deficient mouse model, the numbers of muscle fibers and nuclei in the EDL and GC muscles were similar to each other as compared to those in the normal control group mice (FIGS. 3 and 4). It was confirmed that when the cross-section of the GC tissue was immunohistochemically stained, the area of the muscle fibers in the Slit3-deficient mice was significantly decreased through laminin staining, whereas the number of total nuclei and the number of PAX7 positive cells in the tissue did not exhibit any significant difference through staining of the nucleus and PAX7 (FIG. 5). Through this, it was confirmed that when Slit3 was deficient at the in vivo level, the area of the muscle fiber was remarkably decreased, but the numbers of myoblasts and satellite cells thereof were not changed, and accordingly, the decrease in muscle mass caused by Slit3 deficiency is independent of the proliferation of myoblasts and the proliferation and recruitment of satellite cells thereof.

Example 2 Confirmation of Myoblast Differentiation-Promoting Effect of Slit3

<2-1> Confirmation of Change in Viability of Myoblasts by Slit3

Since it was confirmed that the amount of skeletal muscle was decreased according to Slit3 deficiency, it was confirmed what kind of role Slit3 played in increasing muscle mass. First, it was confirmed whether the role of Slit3 in increasing muscle mass is an effect of increasing the viability of muscle cells.

Specifically, a myoblast C2C12 cell line (purchased from ATCC, USA) was inoculated into a DMEM medium supplemented with 10% fetal bovine serum (FBS) and cultured while 5% $CO_2$ and 37° C. were maintained. After culturing for 24 hours, the cells were treated with recombinant Slit3 (manufactured by Abcam, Cambridge, Mass., USA; and R&D Systems Inc., Minneapolis, Minn., USA) at a concentration of 1 μg/ml or 3 μg/ml and additionally cultured for 24 hours. And then, the cells were washed twice with a PBS solution, treated with a MTT reagent, and then additionally cultured for 2 hours, and the absorbance was measured at 450 nm by an ELISA plate reader. As an untreated control group, a C2C12 cell line, which had not been treated with Slit3, was cultured under the same conditions, and as a positive control group, a C2C12 cell line treated with TNF-α was used.

Figure 6:
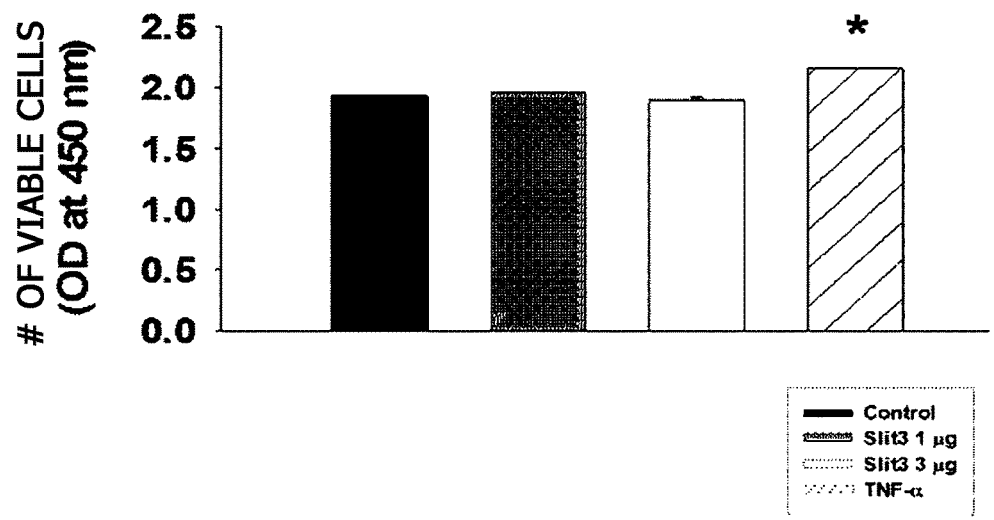
FIG. 6 illustrates the confirmation of changes in cell viability of a C2C12 cell line according to Slit3 treatment in order to confirm the effects of Slit3 on promotion of the differentiation of myoblasts.
Figure 7A:
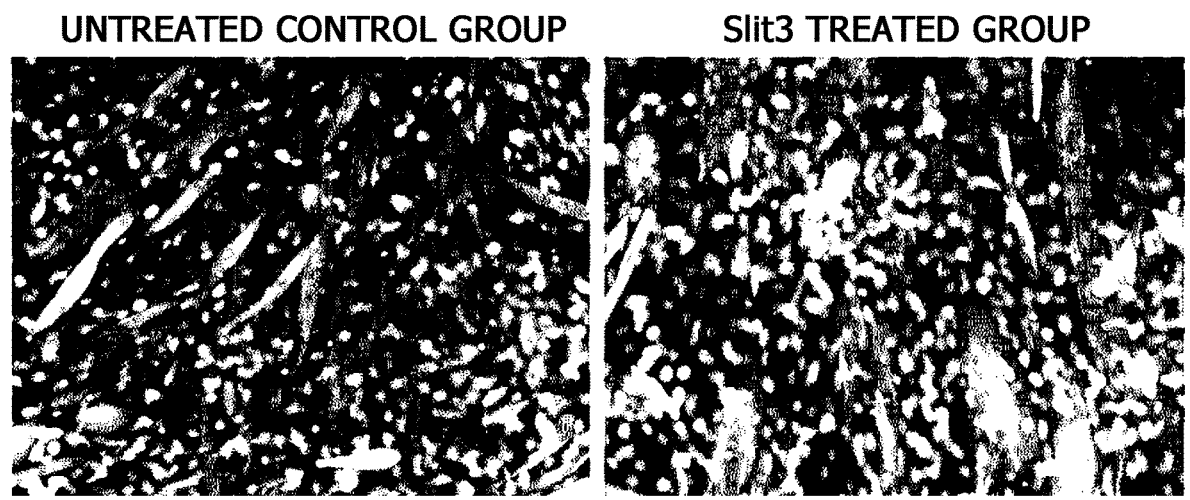
FIGS. 7A to 7E illustrate a differentiation-increasing effect of Slit3 in the differentiation from myoblasts into myotubes.
Figure 7B:
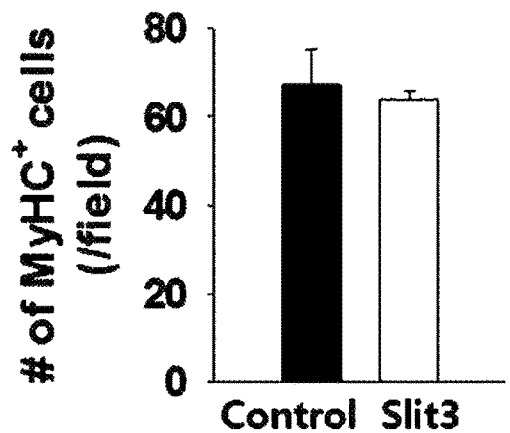
Figure 7C:
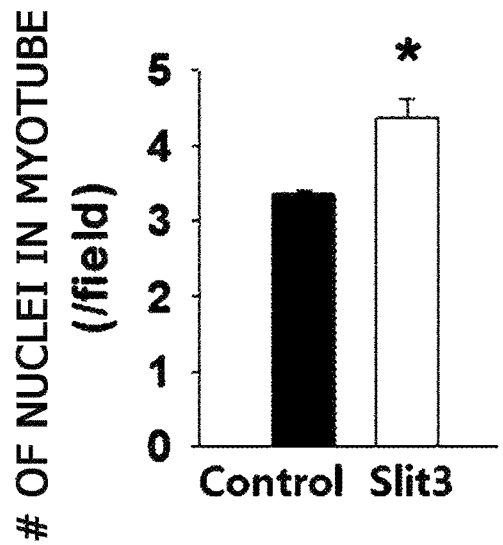
Figure 7D:
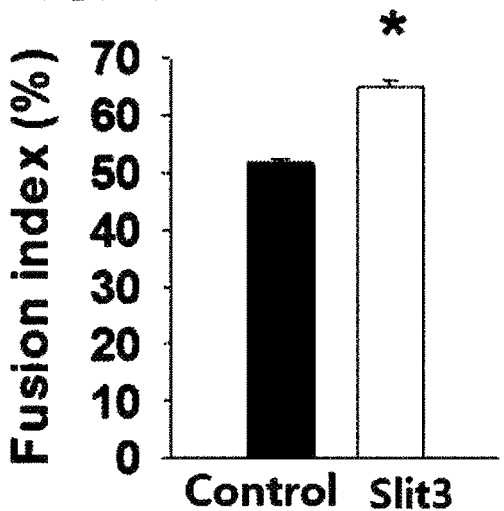
Figure 7E:
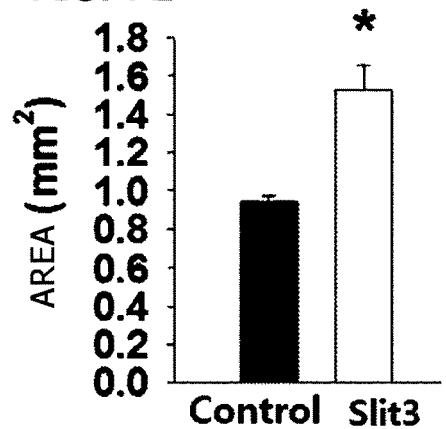
Figure 8A:
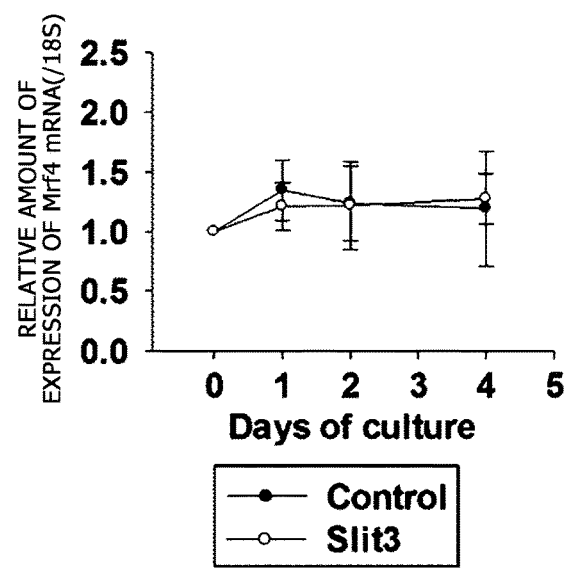
FIGS. 8A to 8F illustrate the changes in mRNA expression levels of various myogenic regulatory factors according to Slit3 treatment in the differentiation process of myoblasts.
Figure 8B:
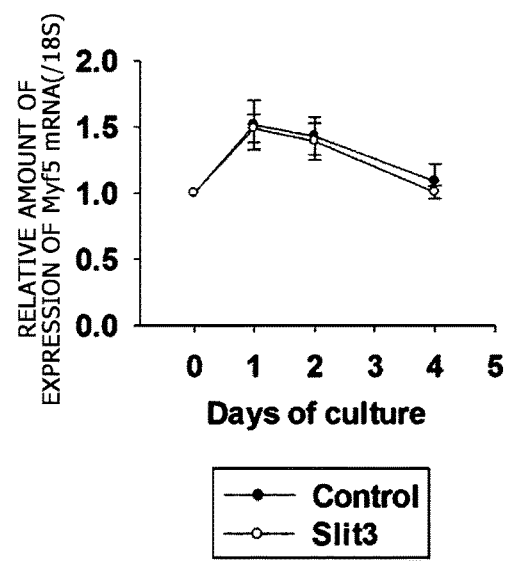
Figure 8C:
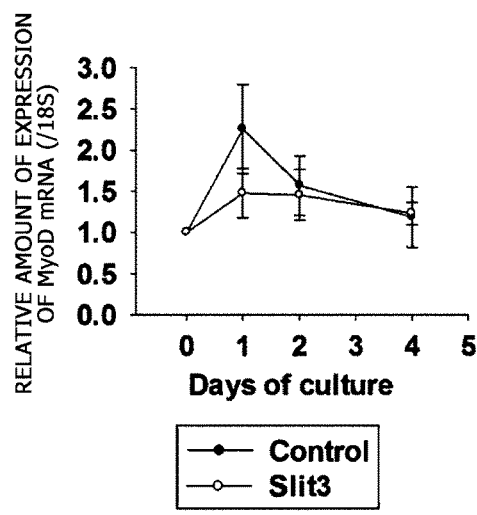
Figure 8D:
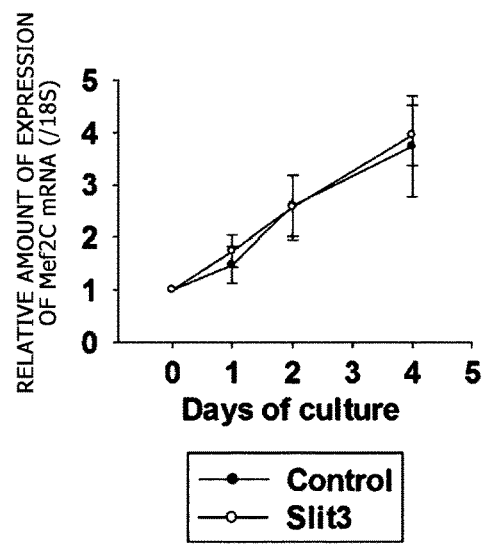
Figure 8E:
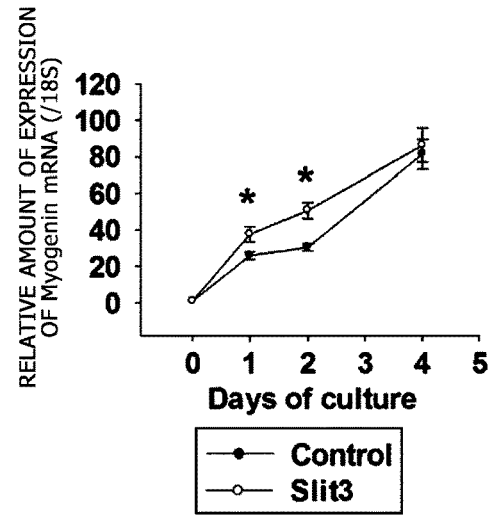
Figure 8F:
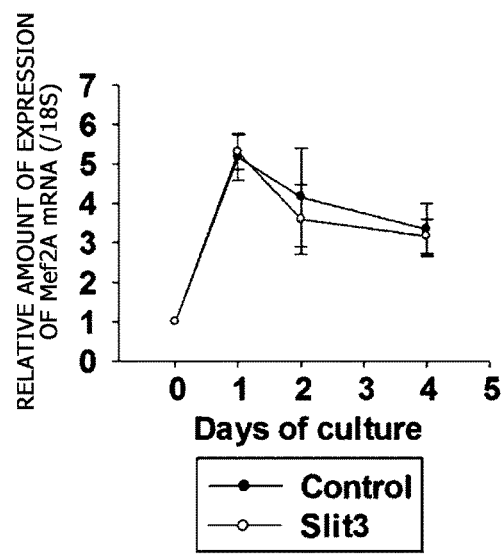

As a result, as illustrated in FIG. 6, it was confirmed that in the positive control group treated with TNF-α, the cell viability was significantly increased as compared to that of the untreated control group, whereas in the experimental group treated with Slit3, the cell viability was not significantly changed.

<2-2> Confirmation of Differentiation-Increasing Effect of Slit3 in Differentiation from Myoblasts into Myotubes Since it was confirmed that the amount of skeletal muscle was decreased according to Slit3 deficiency, it was confirmed what kind of role Slit3 played in increasing muscle mass. Since there was no significant change in the survival of myoblasts by Slit3, the effects of Slit3 on the differentiation process of myoblasts into myotubes were confirmed.

Specifically, C2C12 cells were inoculated into a DMEM medium supplemented with 10% FBS and cultured until 100% confluence. And then, the C2C12 cells were induced so as to be differentiated into myotubes by exchanging the culture medium with a DMEM medium including 1 μg/ml Slit3 recombinant protein and 2% horse serum. After the induction, the differentiated cells were obtained, treated with phosphate buffered saline (PBS), fixed at room temperature for 15 minutes, and treated with 0.1% Triton X-100 to impart permeability to the cell membrane. And then, the treated cells were blocked at room temperature for 1 hour by adding 4% normal donkey serum to the treated cells, and then treated with an anti-myosin heavy chain (MyHC) antibody as a primary antibody and cultured at 4° C. overnight, and washed several times with PBST that is a PBS including 0.1% Tween-20. After the washing, the cells were treated with a secondary antibody to which Alexa Fluor 594 bound and cultured for 1 hour, and MyHC was subjected to immunocytochemistry (ICC) staining. And then, the nuclei of the cells were stained by treating the cells with DAPI, and the stained nuclei were observed with a fluorescence microscope.

As a result, as illustrated in FIG. 7, it was confirmed that in the experimental group differentiated under the treatment of Slit3, the number of cells was not changed as compared to the untreated control group to which a Slit3 recombinant protein had not been added, but the area of the muscle fiber was significantly increased, and the fusion index was remarkably increased (FIG. 7).

Example 3 Confirmation of Slit3 Associated Factors in Differentiation Process of Myoblasts Since it is known that various myogenic regulatory factors (MRFs) such as Myf5, Mrf4, MyoD, myogenin, Mef2A, and Mef2c cause differentiation of myoblasts in the process in which myoblasts are differentiated into myotubes, it was confirmed whether Slit3 induced differentiation of myoblasts by inducing the expression of these regulatory factors.

Specifically, after the C2C12 cells were inoculated into a DMEM supplemented with 10% FBS and cultured until 100% confluence, the C2C12 cells was induced so as to be differentiated into myotubes by exchanging the culture medium with a DMEM medium including 1 μg/ml Slit3 recombinant protein and 2% horse serum and culturing the cells for a total of 5 days. The cells were obtained every 24 hours while being cultured, and suspended in a TRIzol (Invitrogen, USA) reagent, and the total RNA of the differentiated myotubes was extracted according to the manufacturer's protocol and reverse-transcribed by employing 1 μg of RNA as a template and using the corresponding primer and superscript III kit (manufactured by Invitrogen, Inc., USA) to synthesize each of cDNAs of Myf5, Mrf4, MyoD, myogenin, Mef2A, and Mef2c. The amplification conditions for synthesis consisted of 30 cycles of denaturation at 95° C. for 30 seconds, annealing at 60° C. for 30 seconds, and extension at 72° C. for 30 seconds. For the synthesized cDNAs, it was confirmed that the expression level of myogenic regulatory factors was changed according to the presence or absence of treatment of Slit3 in myoblasts induced into differentiation by using a Light Cycler 480 SYBR Green I Master Mix (Roche) and carrying out real-time PCR in a Light Cycler 480 (Roche) apparatus under the conditions of an entire reaction at 95° C. for 10 minutes and 45 cycles of an amplification reaction which is a set of 95° C. for 10 seconds, 55° C. for 15 seconds, and 72° C. for 20 seconds.

Furthermore, the C2C12 cells induced into differentiation for 2 days were obtained, and the expression was confirmed at the protein level by subjecting myogenin induced into an increase in expression by Slit3 to fluorescence immunostaining in the cells induced into differentiation by using an anti-myogenin antibody in the same manner as in Example <2-2>.

As a result, as illustrated in FIGS. 8 to 10, it was confirmed that Slit3 did not exhibit a significant change in the expression of Myf5, Mrf4, MyoD, Mef2A, Mef2c, and the like, but the expression level of mRNA of myogenin was remarkably increased in the experimental group treated with Slit3, and exhibited a level increased about 1.8 times as compared to the expression level of myogenin mRNA in the untreated control group. Further, when the expression level of the myogenin protein was confirmed by fluorescence immunostaining, it was shown that in the experimental group treated with Slit3, the number of myogenin-positive cells were remarkably increased as compared to that in the untreated control group (FIGS. 9 and 10), so that it was confirmed that Slit3 could cause muscles to be formed by increasing the expression of myogenin to promote the differentiation of myoblasts.

Example 4 Confirmation of Myoblast Differentiation-Inducing Effect of Slit3 by β-Catenin Activation

<4-1> Confirmation of Types and Expression Levels of Cadherin Proteins in Myoblasts A receptor of a Slit protein is well known as a Robo protein which is a cell membrane protein. The Robo protein is present in the form of binding to a cadherin in the cell membrane, and it is known that when Slit binds to Robo, the binding between Robo and the cadherin becomes wider, and as a result, β-catenin binding to the cadherin migrates into the cells and is activated. Since the cadherins expressed in myoblasts are N-cadherin and M-cadherin, it was confirmed what type of cadherin could be affected by Slit3 by being associated with a Robo protein in myoblasts.

Specifically, a C2C12 cell line and a HEK297 cell line (kidney cell line) were inoculated into a DMEM medium supplemented with 10% FBS and cultured while 5% $CO_2$ and 37° C. were maintained. After culturing for 24 hours, each cell and brain tissue were obtained, and the expression levels of mRNAs of M-cadherin and N-cadherin were confirmed in the C2C12 cells and the HEK293 cells or brain tissues by carrying out real-time PCR in the same manner as in <Example 3>.

Further, a lysis buffer (20 mM Tris [pH 7.5], 150 mM NaCl, 1 mM EDTA, 1% Triton X-100, 2.5 mM sodium pyrophosphate, 1 mM glycerophosphate, 1 mM $Na_3VO_4$, 1 mM NaF, and a protease-inhibitor mixture) was mixed with each of the cells obtained above, a cell lysate was prepared by reacting the resulting mixture at 4° C. for 20 minutes, and the concentration of the protein in the lysate was confirmed by using a BCA protein analysis kit (Pierce Chemical Co., Rockford, Ill., USA). The cell lysate sample including 10 to 20 μg of the protein was isolated by a 10% gel SDS-PAGE, and then was transferred to a nitrocellulose membrane (Amersham Biosciences, Buckinghamshire, UK). And then, after the cells on the membrane were treated with a TBST buffer solution (500 mM Tris-HCL [pH 7.4], 1.5 M NaCl, 0.1% Tween-20) including 5% skimmed milk and blocked at room temperature for 1 hour, the cells were treated with an anti-M-cadherin antibody or an anti-N-cadherin antibody as a primary antibody and cultured at 4° C. overnight, washed with TBST, treated with TBST including 1% bovine serum albumin (BSA) by using a goose anti-mouse IgG antibody as a secondary antibody, and cultured for 1 hour to carry out a Western blot.

Figure 11A:
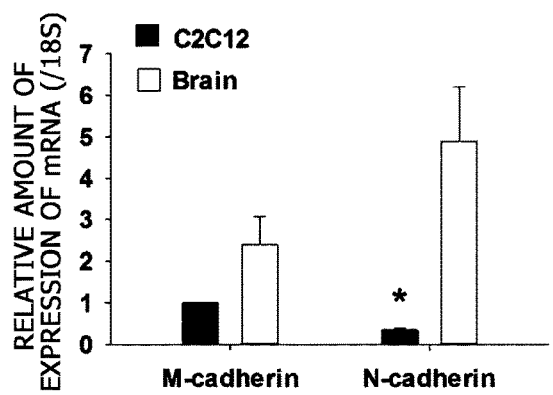
FIG. 11A illustrates mRNA expression levels of M-cadherin and N-cadherin in myoblasts.
Figure 11B:
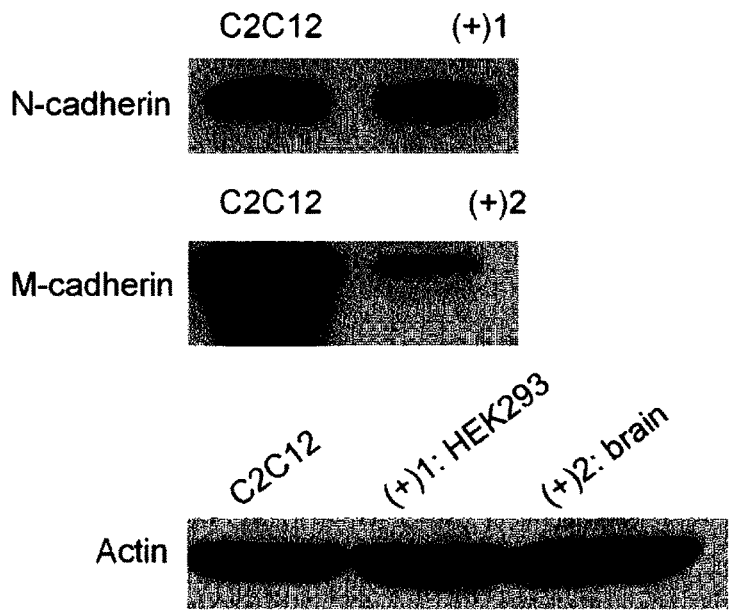
FIG. 11B illustrates protein expression levels of M-cadherin and N-cadherin in myoblasts.

As a result, as illustrated in FIGS. 11A and 11B, it was confirmed that in the C2C12 cells, the expression level of mRNA of M-cadherin was significantly higher than that of N-cadherin (FIG. 11A), and it was confirmed that even in the expression level of proteins, the expression of the protein of M-cadherin is remarkably higher than that of N-cadherin (FIG. 11B).

<4-2> Confirmation of β-Catenin Activity in Myoblasts According to Addition of Slit3

Since it is known that Slit proteins activate β-catenin and β-catenin also binds to a promoter site of myogenin to promote the differentiation of myoblasts by increasing the expression of myogenin, in the present invention, it was also confirmed whether the β-catenin activity of myoblasts is changed by Slit3.

Specifically, the C2C12 cells were transfected with a β-catenin expression vector including a β-catenin-luciferase (luc) reporter gene. And then, after the transfected C2C12 cells were inoculated into a DMEM medium supplemented with 10% FBS and cultured until 100% confluence, the culture medium was exchanged with a DMEM medium including 1 μg/ml Slit3 recombinant protein and 2% horse serum, and a cell protein was extracted by suspending the cultured C2C12 cells in a reporter lysis buffer. The activity of the β-catenin-luciferase was confirmed by mixing a luciferase substrate (manufactured by Promega Corporation, USA) with 10 μl of the extracted cell protein and measuring luminescence with a luminometer.

Figure 12A:
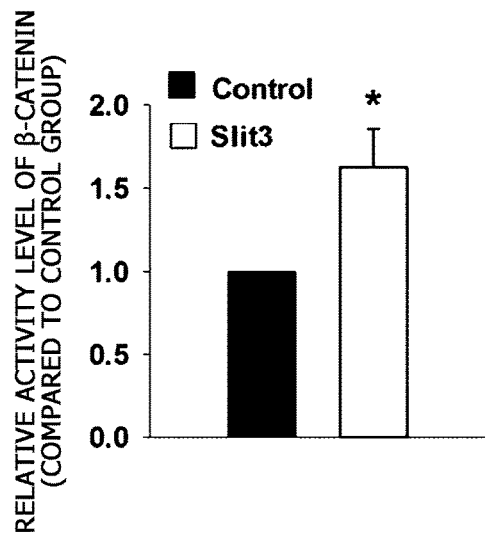
FIG. 12A illustrates confirmation of β-catenin activity according to the addition of Slit3 in myoblasts.

As a result, as illustrated in FIG. 12A, it was confirmed that Slit3 increased the activity of the β-catenin-luciferase in myoblasts to a level of about 1.5 times as compared to the untreated control group (FIG. 12A).

<4-3> Confirmation of Changes in Binding Levels of M-Cadherin and β-Catenin According to Slit3 Treatment Through the fact that the activity of β-catenin is high when C2C12 cells are treated with Slit3, since it was confirmed that Slit3 might bind to a Robo receptor to increase the activity of β-catenin and in the C2C12 cells, the expression level of M-cadherin was higher than the expression level of N-cadherin, it was confirmed by co-immunoprecipitation whether the binding between M-cadherin and β-catenin was changed according to the Slit3 treatment.

Specifically, a human cDNA of a GFP-tagged M-cadherin was purchased, the C2C12 cells were transformed with Lipofectamine 2000 (Gibco, Grand Island, N.Y., USA), and then treated with 1 μg/ml recombinant Slit3 to culture the cells. And then, the cultured cells were obtained and lysed with a TNE buffer (25 mM Tris-HCl, pH 7.4, 150 mM NaCl, 1% Triton X-100, 1 mM EDTA) including a protease inhibitor cocktail (Sigma-Aldrich, St. Louis, Mo., USA) and phosphatase inhibitors (1 mM $Na_3VO_4$, 1 mM NaF). The lysate was immunoprecipitated with an M-cadherin antibody and IgG at 4° C. for 30 minutes, and a Western blot was carried out by using an anti-β-catenin antibody in the same manner as in Example <4-1>.

Figure 12B:
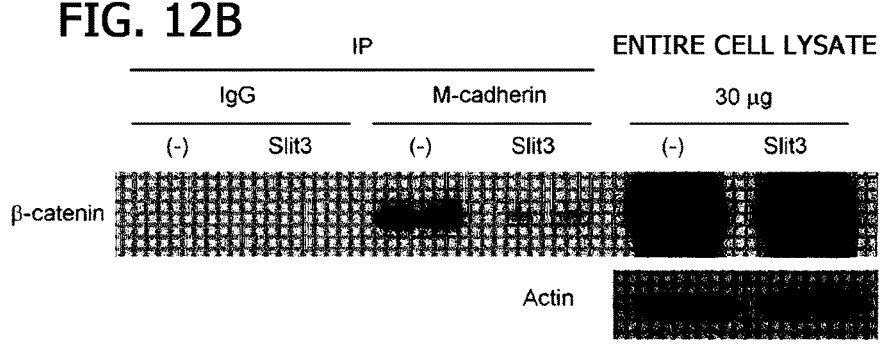
FIG. 12B illustrates a result of confirming the changes in binding levels of M-cadherin and β-catenin according to Slit3 treatment by co-immunoprecipitation.
Figure 12C:
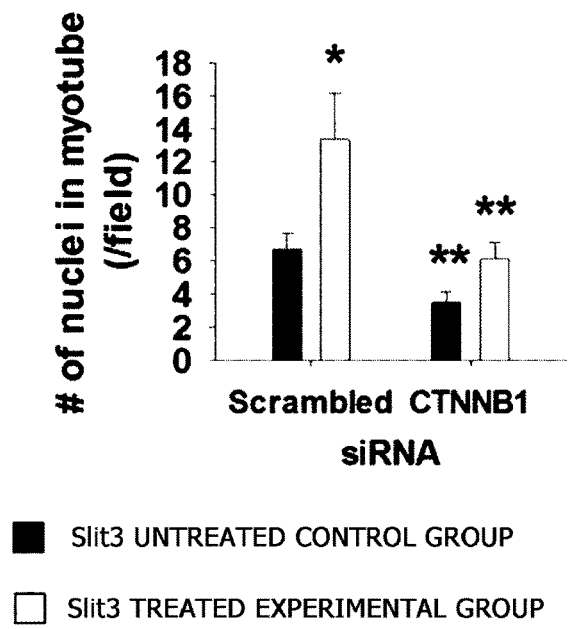
FIGS. 12C to 12E illustrate confirmation of myoblast differentiation yield of Slit3 according to the expression inhibition of β-catenin.
Figure 12D:
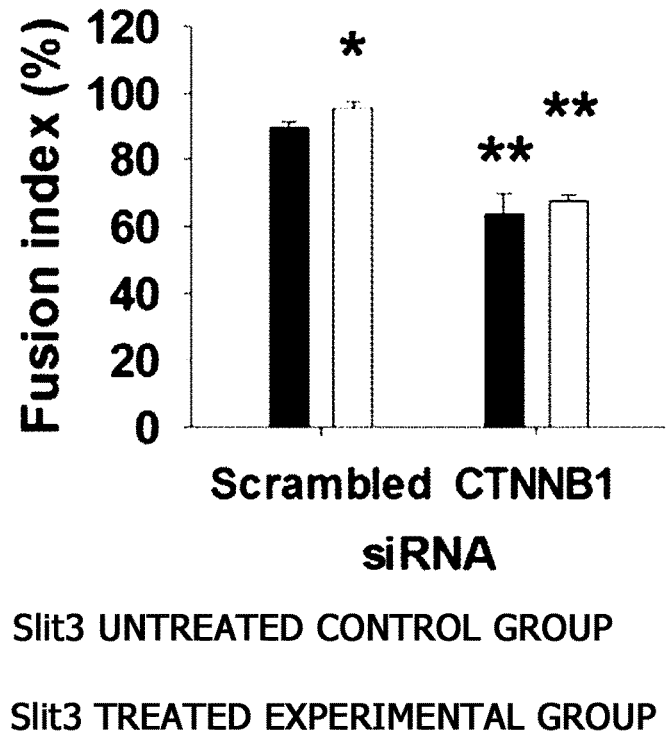
Figure 12E:
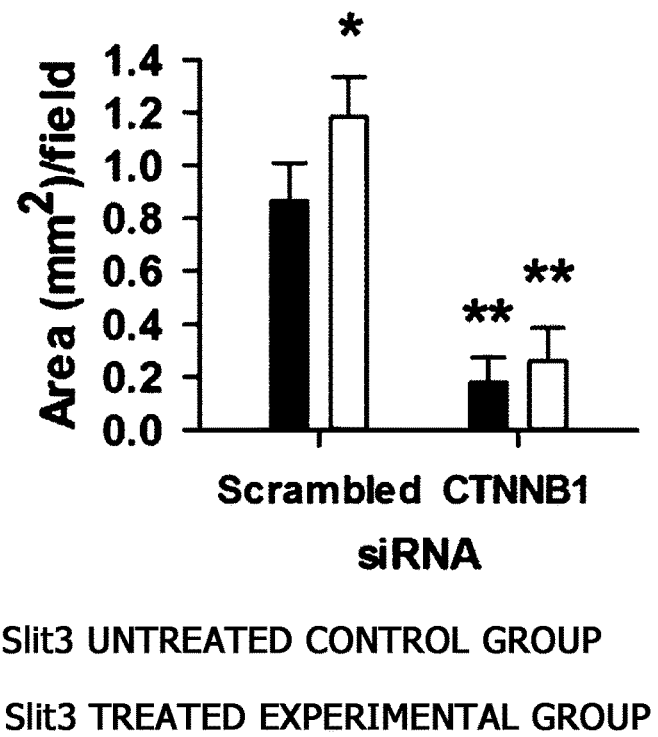
Figure 12F:
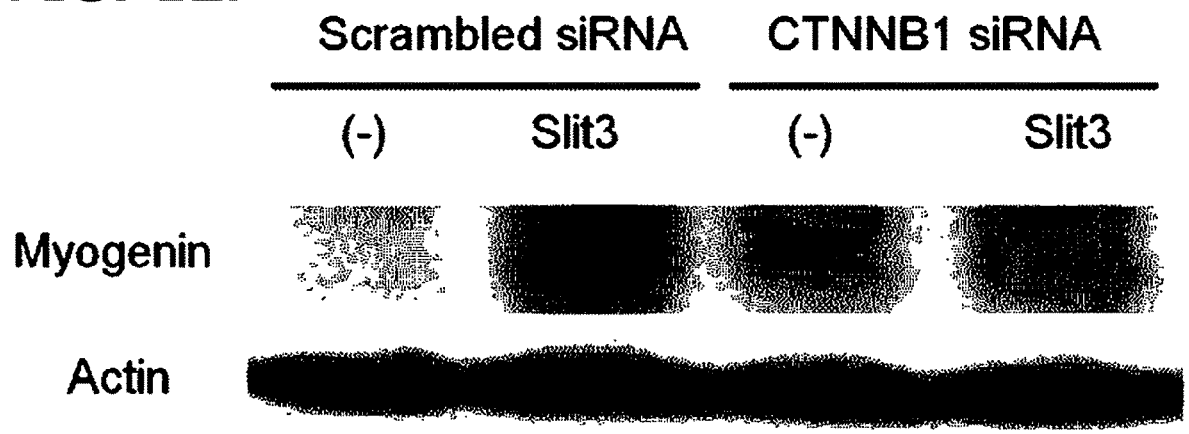
FIG. 12F illustrates changes in expression levels of myogenin in myoblasts treated with Slit3 according to the expression inhibition of β-catenin.

As a result, as illustrated in FIG. 12B, it was confirmed that in the experimental group treated with Slit3, the level of β-catenin binding to M-cadherin was remarkably decreased, so that through Slit3, the binding between M-cadherin and a Robo protein became wider, and as a result, it was confirmed that β-catenin could also be released from M-cadherin to increase its activity (FIG. 12B).

<4-4> Confirmation of Difference in Effect of Slit3 in Promotion of Differentiation of Myoblasts According to Presence or Absence of Expression of β-Catenin Since it was confirmed that β-catenin participated in the process in which Slit3 promoted the differentiation of myoblasts, it was confirmed whether the difference in effects of forming muscles occurred according to the presence or absence of expression of β-catenin when Slit3 was treated.

Specifically, after C2C12 cells were cultured in a DMEM including 10% FBS, a Lipofectamine 200 (Invitrogen) mixture including siRNA (CTNNB1 siRNA) of β-catenin was added thereto, and then the C2C12 cells were further cultured for additional 6 hours. After the culturing, the culture medium was exchanged with a fresh DMEM medium, and C2C12 cells in which β-catenin was knocked out were prepared by additionally culturing the cultured cells for 2 days. In order to be used as a normal control group expressing β-catenin, normal control group cells were prepared by transforming scrambled SiRNA instead of CTNNB1 siRNA.

And then, the prepared β-catenin knockout C2C12 cells or normal control group cells were inoculated into a DMEM medium supplemented with 10% FBS and cultured until 100% confluence, and then cultured by exchanging the culture medium with a DMEM medium including 1 μg/ml Slit3 recombinant protein and 2% horse serum. After the culture, cells were obtained and subjected to immunocytochemistry (ICC) staining in the same manner as in Example <2-2> by using an anti-MyHC antibody as a primary antibody. And then, the nuclei of the cells were stained by treating the cells with DAPI, and the number of cells was quantified as a fluorescence value by observing the stained nuclei with a fluorescence microscope. Fusion index (%) was denoted as a percentage of the number of nuclei of MyHC-expressing myotubes relative to the number of nuclei of the overall MyHC-expressing cells. Further, after the culture, the obtained cells were subjected to Western blot in the same manner as in Example <4-1> by using an anti-myogenin antibody.

As a result, as illustrated in FIGS. 12C to 12E and FIG. 12F, it was confirmed that in the experimental group in which the expression of β-catenin was suppressed by β-catenin siRNA, the hypertrophy of muscle fibers promoted by Slit3 and fusion index were remarkably suppressed, and it was confirmed that the expression of myogenin was also remarkably decreased (FIGS. 12C to 12E and FIG. 12F). Through this, it was confirmed that Slit3 released β-catenin binding to M-cadherin to activate β-catenin of myoblasts and increase the expression of myogenin, and could participate in promotion of the formation of muscles by inducing the differentiation of myoblasts.

Example 5 Confirmation of Robo Receptor Subtype Binding to Slit3 in Myoblasts

<5-1> Confirmation of Robo Receptor Subtype Expressed in Myoblasts

It was confirmed that in the differentiation process of myoblasts, Slit3 could increase the activity of β-catenin and the expression of myogenin, and it was confirmed that the increase in activity of β-catenin and expression of myogenin could be induced through Slit3-Robo receptor binding. The receptor of the Slit protein is a Robo protein, and it has been known until now that four subtypes of Robo1 to Robo4 are present, so that the Robo receptor expressed in myoblasts was confirmed in order to confirm the subtype of Robo receptor associated with Slit3 in myoblasts.

Specifically, a C2C12 cell line and a HEK297 cell line (kidney cell line) were inoculated into a DMEM medium supplemented with 10% FBS and cultured while 5% $CO_2$ and 37° C. were maintained. After culturing for 24 hours, each cell was obtained, and the expression levels of proteins of Robo1, Robo2, Robo3, and Robo4 were confirmed in the C2C12 cells and the HEK293 cells or brain tissues by carrying out Western blot using an anti-Robo1 antibody, an anti-Robo2 antibody, an anti-Robo3 antibody, and an anti-Robo4 antibody in the same manner as in <Example 4>.

As a result, as illustrated in FIG. 13A, it was confirmed that in the C2C12 cells, Robo1 and Robo2 proteins were expressed at a significant level, but Robo3 and Robo4 proteins were not expressed (FIG. 13A).

<5-2> Confirmation of Binding of Slit3-Robo1 and Slit3-Robo2 in Myoblasts

Since it was confirmed that Robo1 and Robo2 proteins were expressed in myoblasts, it was determined whether the receptors of Slit3 protein could be Robo1 and Robo2. In order to confirm that the receptors of Slit3 protein are Robo1 and Robo2, it was confirmed whether the action of Slit3 was lost when the expression of Robo1 and Robo2 was suppressed.

Specifically, C2C12 cells in which Robo1 or Robo2 was knocked out were prepared by carrying out the same method as in Example <4-4> to transform the cells with each of siRNA of Robo1 or Robo2, the C2C12 cells were inoculated into a DMEM medium supplemented with 10% FBS and cultured until 100% confluence, and then cultured by exchanging the culture medium with a DMEM medium including 1 μg/ml Slit3 recombinant protein and 2% horse serum. After the culture, the cells were obtained, and when the expression of Robo1 and Robo2 was expressed, the mRNA expression levels of Robo1, Robo2, and myogenin were confirmed by carrying real-time PCR in the same manner as in <Example 3>.

Figure 13D:
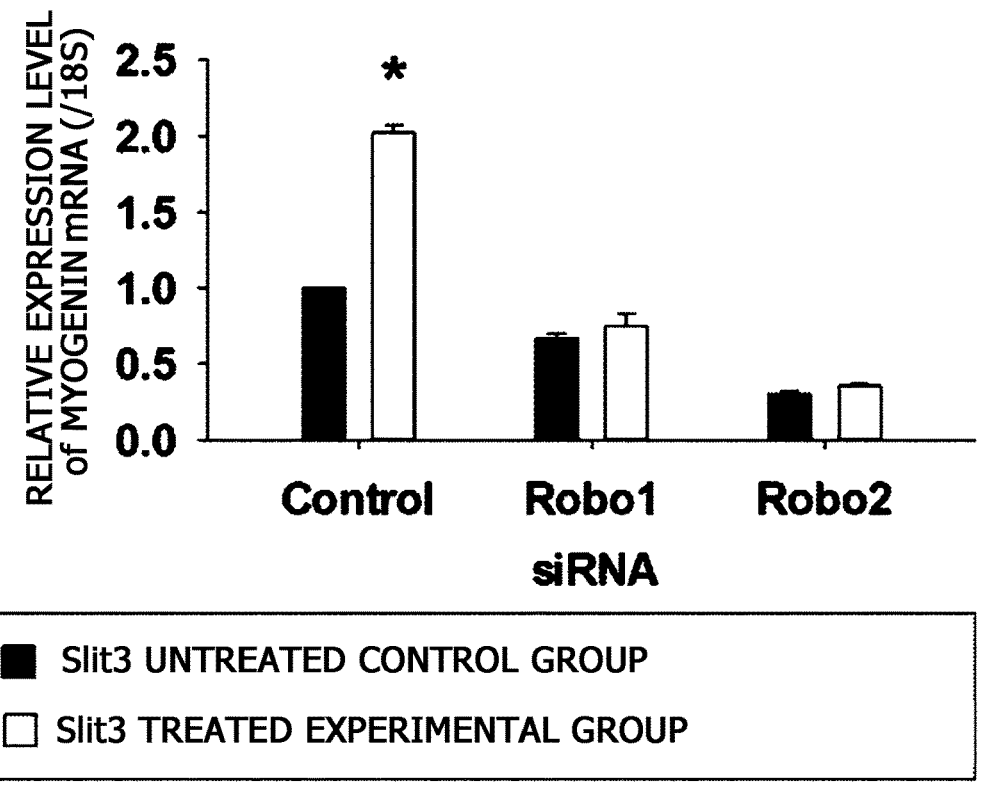
Figure 14A:
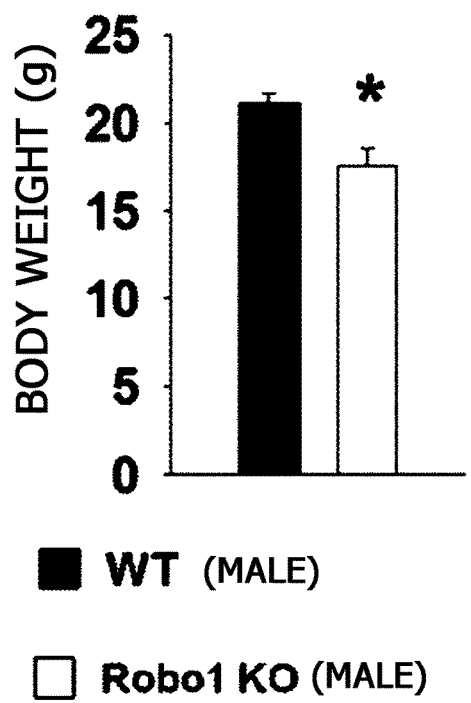
FIGS. 14A to 14E illustrate confirmation of changes in body weight and sarcopenic indices in Robo receptor-deficient mouse models.
Figure 14B:
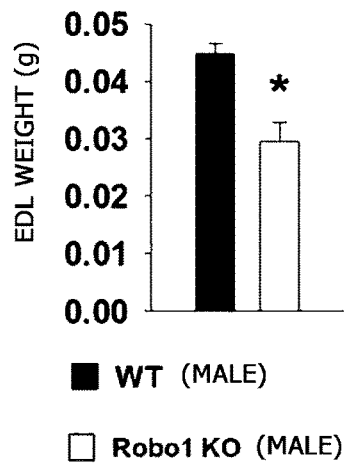
Figure 14C:
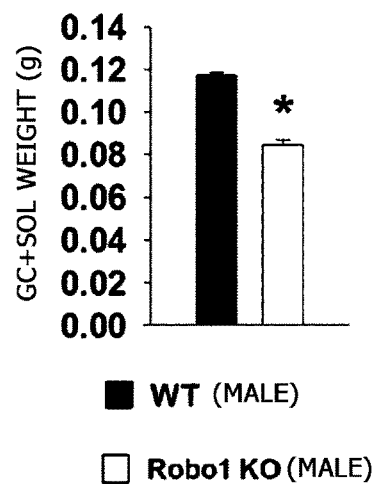
Figure 14D:
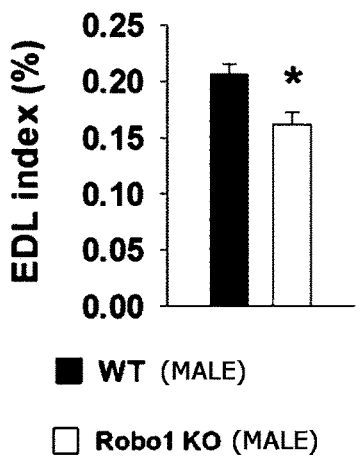
Figure 14E:
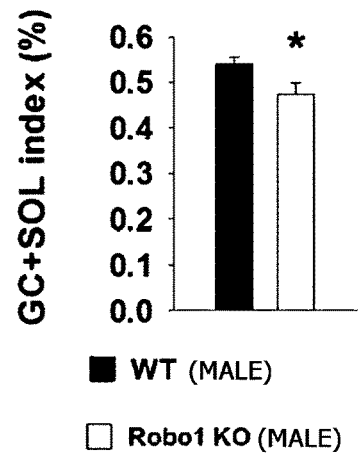
Figure 15A:
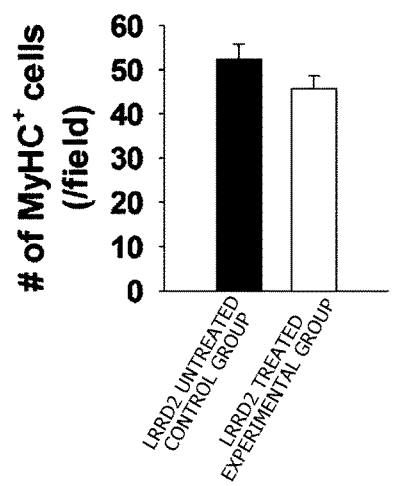
FIGS. 15A to 15D illustrate a myoblast differentiation effect of LRRD2 of Slit3 at the in vitro level.
Figure 15B:
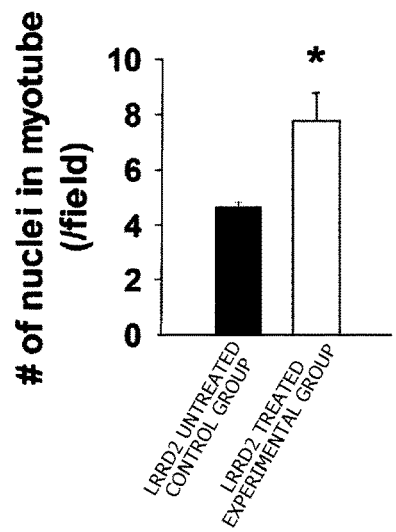
Figure 15C:
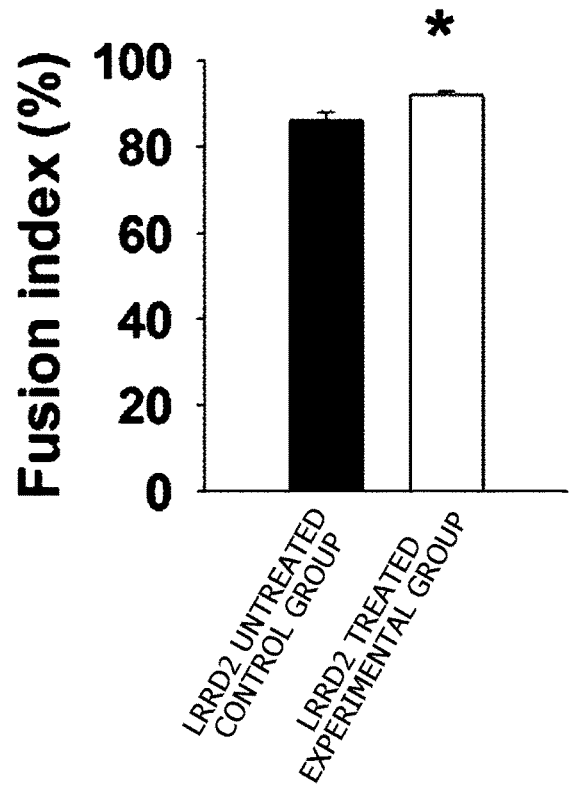
Figure 15D:
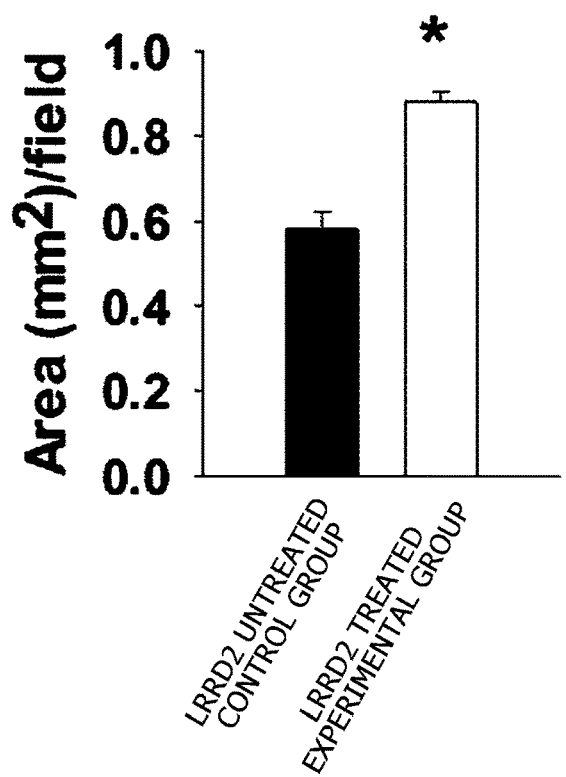
Figure 16A:
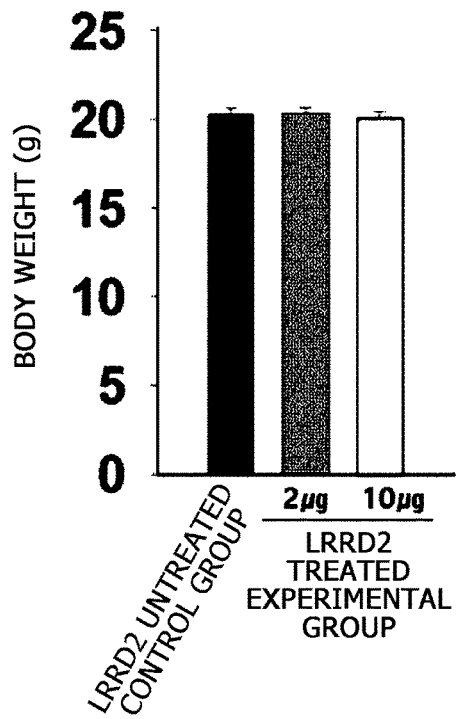
Figure 16B:
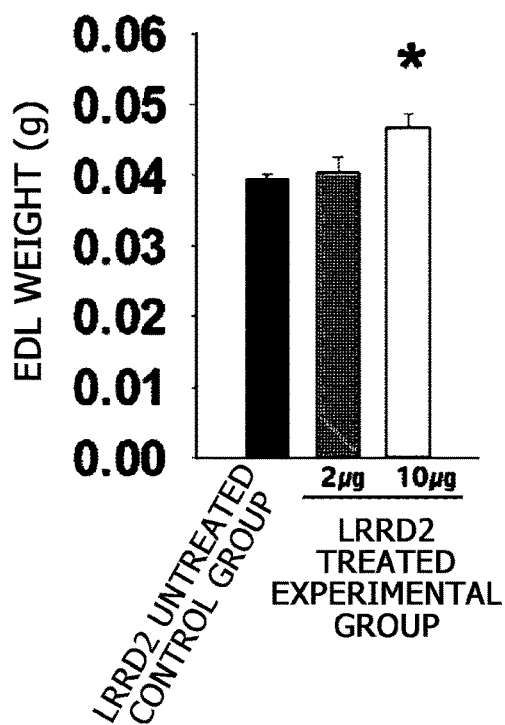
Figure 16C:
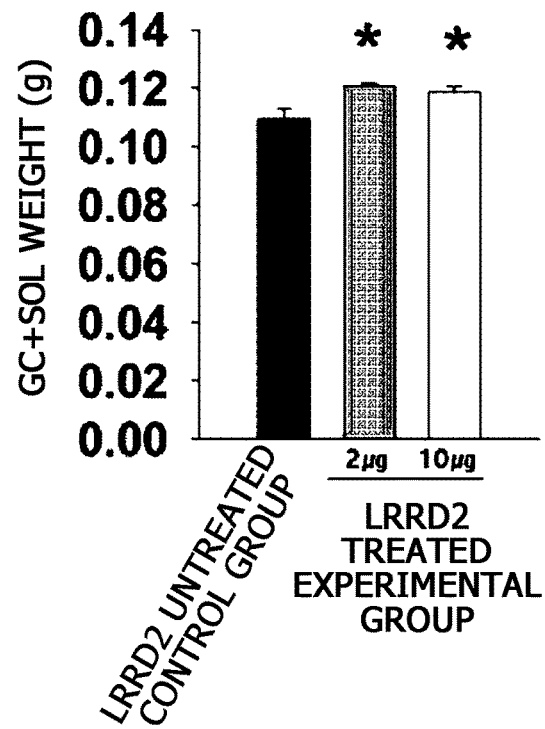
Figure 16D:
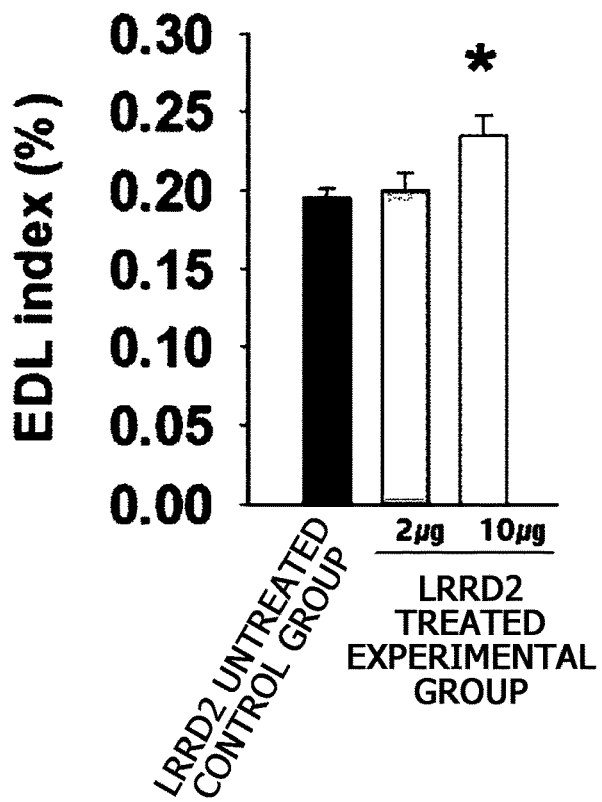

As a result, as illustrated in FIGS. 13B and 13C, it was confirmed that for myogenin of which the expression was increased by Slit3, the expression of myogenin was significantly suppressed as the expressions of Robo1 and Robo2 are suppressed, and as a result, myogenin was expressed at a level similar to that of the control group which was not treated with Slit3 (FIGS. 13B, 13C, and 13D).

Example 6 Confirmation of Role of Robo Receptor in In Vivo Muscle Formation-Promoting Effect by Slit3

In order to specifically confirm the result confirmed in the present invention in vivo, a change in muscle mass was confirmed in a Robo receptor-deficient mouse model.

Specifically, embryos of Robo1 or Robo2 knockout mice were purchased from Mutant Mouse Regional Resource Centers (Stock number 030759-MU; Columbia, Mo., USA), and a Robo1 or Robo2 knockout mouse model was each prepared by breeding the male and female slit3+/−C57BL/6J mice. By selecting male mice as an experimental group among the mice, the body weights, muscle weights and sarcopenic indices of the 7 week-old mouse model were confirmed in the same manner as in Example <1-1>. The Robo2-deficient group did not survive until week 7 and could not be used as an experimental group, and the experiment was carried out only on the Robo1-deficient group, and the Robo1-deficient group was compared with the normal control group.

As a result, as illustrated in the following [Table 3] and FIG. 14, it was confirmed that in the Robo1-deficient mouse model, the body weights were lower and the weights of EDL and the weights of GC+SOL were also lower than those in the normal control group mice, and sarcopenic indices of EDL and sarcopenic indices of GC+SOL were significantly decreased as compared to those in the normal control group (FIG. 14 and Table 3). Through this, it was confirmed that the receptors of myoblasts participating in the formation of the skeletal muscle are Robo1 and Robo2, and Slit3 exhibits a decrease in muscle mass at the in vivo level, particularly when Robo1 is deficient, and accordingly, effects of alleviating sarcopenia could be exhibited through a binding system of Slit3 and Robo1 or Robo2.

TABLE 3

Comparison of Changes in Body Weight and Sarcopenic Indices in Robo1-Deficient Male Mice

| Experimental group | Body weight (g) | Muscle weight (g) | | Sarcopenic index (%) | |
| --- | --- | --- | --- | --- | --- |
| | | EDL | GC + SOL | EDL | GC + SOL |
| Normal control group | 21.1 ± 0.6 | 0.048 ± 0.002 | 0.117 ± 0.001 | 0.206 ± 0.009 | 0.541 ± 0.014 |
| Robo1-deficient group | 17.6 ± 0.9 | 0.029 ± 0.003 | 0.085 ± 0.002 | 0.162 ± 0.011 | 0.474 ± 0.024 |

Example 7 Confirmation of Effects of Slit3 on Differentiation of Myoblasts and Increase in Muscle Mass by LRRD2 Domain Since a human Slit3 protein consists of 1,523 amino acids, and thus is a material having a very large molecular weight of about 170 kDa, it is determined that a medicine using a full-length Slit3 protein is not highly practical, so that it was intended to select only a domain fragment which was determined to exhibit effects of differentiation of myoblasts and an increase in muscle mass among the full-length Slit3. The Slit3 protein includes four Leucine-rich domains, and among the domains, Leucine-rich domain 2 (LRRD2) consisting of 130 amino acids is a portion which binds to the receptor, and through this, it was determined that various cellular actions could be performed, so that it was confirmed whether LRRD2 could exhibit the effects of the full length Slit3 even in effects of promoting differentiation of myoblasts of the present invention and increasing muscle mass.

<7-1> Confirmation of Effects of Slit3 on Differentiation of Myoblasts by LRRD2 at In Vitro Level Specifically, after C2C12 cells were inoculated into a DMEM medium supplemented with 10% FBS and cultured until 100% confluence, the cells were cultured by exchanging the culture medium with a DMEM medium including 10 nM recombinant LRRD2 (Patent Document 1) and 2% horse serum. After the culture, cells were obtained and subjected to immunocytochemistry (ICC) staining in the same manner as in Example <2-2> by using an anti-MyHC antibody as a primary antibody. And then, the nuclei of the cells were stained by treating the cells with DAPI, and the number of cells was quantified as a fluorescence value by observing the stained nuclei with a fluorescence microscope. Fusion index (%) was denoted as a percentage of the number of nuclei of MyHC-expressing myotubes relative to the number of nuclei of the overall MyHC-expressing cells.

As a result, as illustrated in FIG. 15, it was confirmed that in the experimental group treated with the recombinant LRRD2 protein, the area of myotubes and fusion index levels were remarkably increased as compared to the untreated control group, which exhibited a level similar to that of the case where the full-length Slit3 protein was treated (FIG. 15).

<7-2> Confirmation of Effects of Slit3 on Increases in Body Weight and Sarcopenic Index by LRRD2

Specifically, a sarcopenia mouse model in which sex hormones were induced to be deficient was prepared by cutting the abdomens of 8 week-old female C57BL/6 mice open and excising the ovaries, and the recombinant LRRD2 domain was administered at a dosage of 2 μg or 10 μg and a frequency of once a day or five times a week intravenously to the sarcopenia mouse model. After 4 weeks, the body weights, muscle weights and sarcopenic indices of the 13 week-old mouse model were confirmed in the same manner as in Example <1-1>.

As a result, as shown in the following [Table 4] and FIG. 16, it was confirmed that the body weights of the mouse model to which LRRD2 was administered did not exhibit a significant change as compared to the control group to which LRRD2 was not administered, but with respect to muscle mass and sarcopenic index, in the mouse model to which LRRD2 was administered, the weights of EDL and the weights of GC+SOL were significantly increased as compared to the control group to which LRRD2 was not administered, and the sarcopenic indices of EDL and the sarcopenic indices of GC+SOL were also significantly increased as compared to the control group to which LRRD2 was not administered (FIG. 16 and Table 4).

TABLE 4

Comparison of Sarcopenic Indices by LRRD2 in Ovary-Excised Female Mice

| Experimental group | | Muscle weight (g) | | Sarcopenic index (%) | |
|---|---|---|---|---|---|
| | | EDL | GC + SOL | EDL | GC + SOL |
| Normal control group | | 0.040 ± 0.001 | 0.109 ± 0.003 | 0.196 ± 0.006 | 0.540 ± 0.017 |
| LRRD2 treatment group | 2 μg | 0.041 ± 0.005 | 0.121 ± 0.001 | 0.200 ± 0.010 | 0.596 ± 0.011 |
| | 10 μg | 0.047 ± 0.002 | 0.119 ± 0.002 | 0.235 ± 0.013 | 0.594 ± 0.015 |

The invention claimed is:

1. A method for treating a muscle disease caused by decrease in differentiation of myoblast into myotube, muscle wasting or muscle degeneration, the method comprising the steps of: administering one protein selected from a group consisting of amino acid sequences of the following SEQ ID Nos. 1 and 4, or a gene encoding the same to an individual in need thereof:
   a Slit3 protein consisting of an amino acid of SEQ ID No. 1; and
   a LRRD2 protein domain consisting of an amino acid of SEQ ID No. 4.

2. A method for improving muscular function in a muscle disease caused by decrease in differentiation of myoblast into myotube, muscle wasting or muscle degeneration, the method comprising the steps of: administering one protein selected from a group consisting of amino acid sequences of the following SEQ ID Nos. 1 and 4, or a gene encoding the same to an individual in need thereof:
   a Slit3 protein consisting of an amino acid of SEQ ID No. 1; and
   a LRRD2 protein domain consisting of an amino acid of SEQ ID No. 4.

3. A method for treating a muscle disease caused by Robo1 or Robo2 deficiency, the method comprising the steps of: administering a gene encoding one protein selected from a group consisting of amino acid sequences of the following SEQ ID Nos. 2 and 3 to an individual in need thereof:
   a Robo1 protein consisting of an amino acid of SEQ ID No. 2; and
   a Robo2 protein consisting of an amino acid of SEQ ID No. 3.

4. A method for improving muscular function in a muscle disease caused by Robo1 or Robo2 deficiency, the method comprising the steps of: administering a gene encoding one protein selected from a group consisting of amino acid sequences of the following SEQ ID Nos. 2 and 3 to an individual in need thereof:
   a Robo1 protein consisting of an amino acid of SEQ ID No. 2; and
   a Robo2 protein consisting of an amino acid of SEQ ID No. 3.

* * * * *